United States Patent
Padidam

(10) Patent No.: US 9,034,650 B2
(45) Date of Patent: May 19, 2015

(54) SITE-SPECIFIC SERINE RECOMBINASES AND METHODS OF THEIR USE

(75) Inventor: Malla Padidam, Chalfont, PA (US)

(73) Assignee: Intrexon Corporation, Blacksburg, VA (US)

( * ) Notice: Subject to any disclaimer, the term of this patent is extended or adjusted under 35 U.S.C. 154(b) by 818 days.

(21) Appl. No.: 11/049,552

(22) Filed: Feb. 2, 2005

(65) Prior Publication Data
US 2006/0172377 A1 Aug. 3, 2006

(51) Int. Cl.
C12N 15/87 (2006.01)
C12N 9/00 (2006.01)

(52) U.S. Cl.
CPC ........................................ C12N 9/00 (2013.01)

(58) Field of Classification Search
None
See application file for complete search history.

(56) References Cited

U.S. PATENT DOCUMENTS

| | | | |
|---|---|---|---|
| 4,945,050 | A | 7/1990 | Sanford et al. |
| 5,175,384 | A | 12/1992 | Krimpenfort et al. |
| 5,175,385 | A | 12/1992 | Wagner et al. |
| 5,750,376 | A | 5/1998 | Weiss et al. |
| 5,849,287 | A | 12/1998 | Greenberger et al. |
| 5,919,653 | A | 7/1999 | Albert et al. |
| 6,114,600 | A | 9/2000 | Ow et al. |
| 6,746,870 | B1 | 6/2004 | Ow et al. |
| 6,808,925 | B2 | 10/2004 | Calos |
| 6,632,672 | B2 | 8/2005 | Ow |
| 7,141,426 | B2 | 11/2006 | Calos |
| 2002/0094516 | A1 | 7/2002 | Calos et al. |
| 2002/0123145 | A1 | 9/2002 | Ow |
| 2003/0050258 | A1 | 3/2003 | Calos |
| 2005/0003540 | A1 | 1/2005 | Calos |
| 2005/0009182 | A1 | 1/2005 | Ow |
| 2005/0034186 | A1* | 2/2005 | Harvey ........................... 800/19 |
| 2005/0054106 | A1 | 3/2005 | Ow et al. |
| 2005/0208021 | A1 | 9/2005 | Calos |
| 2006/0046294 | A1 | 3/2006 | Ow et al. |
| 2006/0128020 | A1 | 6/2006 | Calos |
| 2007/0059835 | A1 | 3/2007 | Chalberg, Jr. et al. |
| 2007/0077589 | A1 | 4/2007 | Calos |
| 2008/0020465 | A1 | 1/2008 | Padidam |

FOREIGN PATENT DOCUMENTS

| | | |
|---|---|---|
| WO | WO 02/08409 A2 | 1/2002 |
| WO | WO 02/38613 A2 | 5/2002 |
| WO | WO 03/093306 A2 | 11/2003 |
| WO | WO 2004/080162 A2 | 9/2004 |
| WO | WO 2005/084430 A1 | 9/2005 |
| WO | WO 02/42214 A1 | 4/2006 |
| WO | WO 2006/083253 A1 | 8/2006 |

OTHER PUBLICATIONS

Groth et al., J. Mol. Biol., 335, 667-678, 2004.*

Groth et al., Proc. Natl. Acad. Sci. USA, 97, 11, 5995-6000, 2000.*
Paul Sadowski., "Site-Specific Recombinases: Changing Partners and Doing the Twist", Journal of Bacteriology, 1986, 165: 341-347.
Paul J. Sadowski et al.,"Site-Specific Recombinases: hops, flips, and flops", Faseb Journal, 1993, 7: 760-767.
David I. Friedman.,"Integration Host Factor: A Protein for All Reasons", Cell, 1988, 55: 545-554.
S. Finkel et al.,"The Fis protein: it's not just for DNA inversion anymore", Molecular Microbiology, 1992 6: 3257-3265.
E. P. Brandon et al.,"Targeting the mouse genome: a compendium of knockouts (part 1)", Current Biology, 1995, 5: 625-634.
E. P. Brandon et al., "Targeting the mouse genome: a compendium of knockouts (part 2)", Current Biology, 1995, 5: 758-765.
Nigel J. Kilby et al., "Site-specific recombinases: tools for genome engineering", Trends Genet, 1993, 9: 413-421.
Brian Sauer., "Manipulation of Transgenes by Site-Specific Recombination: Use of Cre Recombinase", Methods in Enzymology., 1993, 225: 890-900.
Susan M. Dymecki., "Flp recombinase promotes site-specific DNA recombination in embryonic stem cells and transgenic mice", Proc Nat'l Acad. Sci., USA, 1996, 93: 6191-6196.
Ken Abremski et al., "Bacteriophage P1 Site-specific Recombination", Journal of Biological Chemistry, 1984, 259: 1509-1514.
Bhaskar Thyagarajan et al., "Site-Specific Genomic Integration in mammalian cells mediated by phage oC31 integase", Molecular Cell Biology, 2001, 21: 3926-3934.
Brian Sauer et al., "Targeted Insertion of Exogenous DNA into the Eukaryotic Genome by the Cre Recombinase", The New Biologist, 1990, 2: 441-449.
S. Fukushige et al.,"Genomic Targeting with a Positive-Selection lox Integration Vector Allows Highly Reproducible Gene Expression in Mammalian Cells", Proc. Nat'l. Acad., Sci. USA., 1992, 89: 7905-7909.

(Continued)

*Primary Examiner* — Nancy T Vogel
(74) *Attorney, Agent, or Firm* — Sterne, Kessler, Goldstein & Fox P.L.L.C.

(57) ABSTRACT

The present invention provides a method for obtaining site-specific recombination in a eukaryotic cell, the method comprising providing a eukaryotic cell that comprises a first recombination attachment site and a second recombination attachment site; contacting the first and second recombination attachment sites with a prokaryotic recombinase polypeptide, resulting in recombination between the recombination attachment sites, wherein the recombinase polypeptide can mediate recombination between the first and second recombination attachment sites, the first recombination attachment site is a phage genomic recombination attachment site (attP) or a bacterial genomic recombination attachment site (attB), the second recombination site is attB or attP, and the recombinase is selected from the group consisting of a *Listeria monocytogenes* phage recombinase, a *Streptococcus pyogenes* phage recombinase, a *Bacillus subtilis* phage recombinase, a *Mycobacterium tuberculosis* phage recombinase and a *Mycobacterium smegmatis* phage recombinase, provided that when the first recombination attachment site is attB, the second recombination attachment site is attP and when the first recombination attachment site is attP, the second recombination attachment site is attB. The invention also describes compositions, vectors, and methods of use thereof, for the generation of transgenic cells, tissues, plants, and animals. The compositions, vectors and methods of the present invention are also useful in gene therapy applications.

24 Claims, 14 Drawing Sheets

(56) References Cited

OTHER PUBLICATIONS

J. P. DiSanto et al.,"Lymphoid Development in Mice with a Targeted Deletion of the Interleukin 2 Receptor (gamma) Chain", Proc., Nat'l Acad. Science USA., 1995, 92: 377-38.

Hua Gu et al., "Deletion of a DNA Polymerase B Gene Segment in T Cells Using Cell Type-Specific Gene Targeting", 1994, 265: 103-106.

Ralf Kuhn et al., "Inducible Gene Targeting in Mice", Science, 1995, 269: 1427-1429.

P. C. Orban et al., "Tissue-and Site-Specific DNA Recombination in Transgenic Mice", Proc. Nat'l. Acad. Science USA., 1992, 89: 6861-6865.

J. van Deursen et al.,"Cre-Mediated Site-Specific Translocation between Nonhomologous Mouse Chromosomes", Proc. Nat'l. Acad. Science USA., 1995, 92: 7376-7380.

Scott L. Medberry et al., "Intra-chromosomal rearrangements generated by Cre-lox site-specific recombination", Nucleic Acids Research, 1995, 23: 485-490.

Brian I. Osborne et al., "A system for insertional mutagenesis and chromosomal rearrangement using the Ds transposon and Cre-lox", The Plant Journal., 1995 7: 687-701.

Jose G. Pichel et al., "Timing of SV40 oncogene activation by site-specific recombination determines subsequent tumor progression during murine lens development", Oncogene, 1993 8: 3333-3342.

L.A. Bibb, et al., "Integration and excision of the Mycobacterium tuberculosis prophage-like element", phivRv1. Mol. Microbiol., 2002, 45:1515-1526.

Amy C. Groth et al., "Phage Integrases: Biology and Applications", J. Mol. Biol., 2004 335: 667-678.

T. Nagata et al., "Tobacco BY-2 cell line as the Hela cell in the cell biology of higher plants", Intl, Rev. Cytol., 1992 132: 1-30.

B. Verdaguer et al., "Functional organization of the cassava vein mosaic virus (CsVMV) promoter", Plant Mol. Biol., 1998, 37: 1055-1067.

M. Loessner et al., "Complete nucleotide sequence, molecular analysis and genome structure of bacteriophage A118 of *Listeria monocytogenes*: implications for phage evolution", Mol. Microbiol., 2000, 35: 324-340.

J. Mediavilla et al., "Genome organization and characterization of mycobactariophage Bxb1", Mol. Microbiol., 2000, 38: 955-970.

C. Canchaya et al., "Genome analysis of an inducible prophage and prophage remnants integrated in the *Streptococcus pyogenes* strain SF370", Virology, 2002, 302: 245-258.

V, Lazarevic et al., "Nucleotide sequence of the *Bacillus subtilis* temperate bacteriophage SPBc2", Microbiology, 1999, 145: 1055-1067.

Masafumi Onodera et al., "Successful Peripheral T-Lymphocyte-Directed Gene Transfer for a Patient With Severe Combined Immune Deficiency Caused by Adenosine Deaminase Deficiency", Blood, 1998, 91: 30-36.

Richard D. Palmiter et al., "Transgenic Mice", Cell, 1985, 41: 343.

M. C. Smith et al., "2000 Diversity in the serine recombinases", Mol. Microbiol., 44: 299-307.

Lucy Cherbas et al., "Identification of endyscone response elements by analysis of the *Drosophila* Eip28/29 gene," Genes & Development, 1991, 5:120-131.

Pier Paolo D'Avino et al., "The moulting hormone ecdysone is able to recognize target elements composed of direct repeats," Molecular and Cellular Endocrinology, 1995, 113:1-9.

Christophe Antoniewski et al., "The Ecdysone Response Enhance to the Fbp1 Gene of *Drosophilla melanogaster* is a direct target for the EcR/USP Nuclar Receptor," Molecular and Cellular Biolgy, 1994, 14, 4465-4474.

International Preliminary Report on Patentability for PCT/US2005/003851, dated Aug. 16, 2007.

Ghosh, P., et al., "The Orientation of Mycobacteriophage Bxb1 Integration Is Solely Dependent on the Central Dinucleotide of *attP* and *attB*," Mol. Cell 12:1101-1111, Cell Press (2003).

Barletta, R.G., et al., "Identification of expression signals of the mycobacteriophages Bxb1, L1 and TM4 using the *Escherichia-Mycobacterium* shuttle plasmids pYUB75 and pYUB76 designed to create translational fusions to the *lacZ* gene," J. Gen. Microbiol. 138:23-30, Society for General Microbiology (1992).

Bibb, L.A., et al., "Integration and excision by the large serine recombinase ΦRv1 integrase," Mol. Microbiol. 55:1896-1910, Blackwell Publishing (Mar. 2005).

Bujnicki, J.M. and Radlinska, M., "Cloning and Characterization of M.Lmo A118I, a Novel DNA:m$^4$C methyltransferase from the *Listeria monocytogenes* Phage A118, a Close Homolog of M.NgoMXV," Acta Microbiol. Pol. 50:155-160, Polish Society of Microbiologists (2001).

Canchaya, C., et al., "Genome Analysis of an Inducible Prophage and Prophage Remnants Integrated in the *Streptococcus pyogenes* Strain SF370," Virology 302:245-258, Academic Press (2002).

Desiere, F., et al., "Comparative Genomics of the Late Gene Cluster from *Lactobacillus* Phages," Virology 275:294-305, Academic Press (2000).

Desiere, F., et al., "Comparative Genomics Reveals Close Genetic Relationships Between Phages from Dairy Bacteria and Pathogenic *Streptococci*: Evolutionary Implications for Prophage-Host Interactions," Virology 288:325-341, Academic Press (2001).

Ghosh, P., et al., "Synapsis in Phage Bxb1 Integration: Selection Mechanism for the Correct Pair of Recombination Sites," J. Mol. Biol. 349:331-348, Academic Press (Jun. 2005).

Ghosh, P., et al., "The Orientation of Mycobacteriophage Bxb1 Integration Is Solely Dependent on the Central Dinucleotide of attP and attB," Mol. Cell. 12:1101-1111, Cell Press (2003).

Hendrix, R.W., et al., "Evolutionary relationships among diverse bacteriophages and prophages: All the world's a phage," Proc. Natl. Acad. Sci. U.S.A. 96:2192-2197, National Academy of Sciences (1999).

Jain, S. and Hatfull, G.F., "Transcriptional regulation and immunity in mycobacteriophage Bxb1," Mol. Microbiol. 38:971-985, Blackwell Publishing (2000).

Kim, A.I., et al., "Mycobacteriophage Bxb1 integrates into the *Mycobacterium smegmatis* groEL1 gene," Mol. Microbiol. 50:463-473, Blackwell Publishing (2003).

Lauth, M., "The Family is Growing: Old and New Members of the Family of Site-Specific Recombinases and Their Application to Genome Engineering," Curr. Pharmacogen. 2:267-276, Bentham Science Publishers (Sep. 2004).

Lazarevic, V., et al., "Nucleotide sequence of the *Bacillus subtilis* temperate bacteriophage SPβc2," Microbiology 145:1055-1067, Kluwer Academic/Plenum Publishers (1999).

Loessner, M.J., et al., "A New Procedure for Efficient Recovery of DNA, RNA, and Proteins from *Listeria* Cells by Rapid Lysis with a Recombinant Bacteriophage Endolysin," Appl. Environ. Microbiol. 61:1150-1152, American Society for Microbiology (1995).

Loessner, M.J., et al., "Heterogeneous endolysins in *Listeria monocytogenes* bacteriophages: a new class of enzymes and evidence for conserved holing genes within the siphoviral lysis cassettes," Mol. Microbiol. 16:1231-1241, Blackwell Publishing (1995).

Wendlinger, G., et al., "Bacteriophage receptors on *Listeria monocytogenes* cells are the N-acetylglucosamine and rhamnose substituents of teichoic acids or the peptidoglycan itself," Microbiology 142:985-992, Kluwer Academic/Plenum Publishers (1996).

Office Action mailed Jul. 7, 2010 in U.S. Appl. No. 11/841,426, filed Aug. 20, 2007.

Gustafsson, C. et al., "Codon bias and heterologous protein expression," TRENDS in Biotechnology 22: 346-353, Elsevier Ltd. (2004).

Stoll, S.M., et al., "Phage TP901-1 Site-Specific Integrase Functions in Human Cells," J. Bacterial. 184:3657-3663, American Society for Microbiology (2002).

Chang, C. et al., Accession No. M81760, "Identification of the attachment site for the *Bacillus subtilis* Bacteriophage SPB," (1994) (1 page), entry downloaded from http://www.ncbi.nlm.nih.gov/nuccore/ 143286 on Jan. 11, 2011.

Camus, J.C. et al., sequence NC_00962 for "Mycobacterium tuberculosis H37Rv, complete genome," published in Microbiology

(56) References Cited

OTHER PUBLICATIONS (*Reading, Engl.*) 148 (PT 10): 2967-2973 (2002), entry downloaded from http://www.ncbi.nlm.nih.gov/nuccore/57116681 on Dec. 13, 2010 (2 pages).

Mediavilla, J. et al., sequence NC_002656 for "Mycobacterium phage Bxb1, complete genome," published in *Mol. Microbiol.* 38: 955-970 (2000), entry downloaded from http://www.ncbi.nlm.nih.gov/nuccore/NC_002656?report=genbank&from=29491&to=30 on Dec. 13, 2010 (2 pages).

Chang, C. et al., Accession No. M81761.1, "*B. subtilis* phage SPB ATTB site," (1994), 1 page, entry downloaded from ncbi.nlm.nih.gov/nuccore/ M18761 on Oct. 3, 2011.

Cole, S.T. et al., Accession No. CAB09083, "Probable phiRv1 integrase [*Mycobacterium* tuberculosis H37Rv]," (1998), 2 pages, entry downloaded from ncbi.nlm.nih.gov/protein/CAB09083 on Oct. 3, 2011.

Ferretti, J.J. et al., Accession No. AAK33618, "putative integrase; bacteriophage 370.1 [*Streptococcus pyogenes* M1 GAS]," (2001), 2 pages, entry downloaded from ncbi.nlm.nih.gov/protein/AAK33618 on Oct. 3, 2011.

Lazarevic, V. et al., Accession No. AAC12974, "site-specific recombinase [*Bacillus* phage SPbeta]," (1998), 1 page, entry downloaded from ncbi.nlm.nih.gov/protein/AAC12974 on Oct. 3, 2011.

Mahairas, G.G., Accession No. MBU35021, "*Mycobacterium bovis* BCG DNA flanking deletion region 3," (1996), 1 page, entry downloaded from ncbi.nlm.nih.gov/nuccore/1049243 on Oct. 3, 2011.

Nakagawa, I. et al., Accession No. BA000034, "*Streptococcus pyogenes* SSI-1 DNA, complete genome," (2003), 730 pages, entry downloaded from ncbi.nlm.nih.gov/nuccore/BA000034 on Oct. 3, 2011.

Beres, S.B. et al., Accession No. NC_003485, "*Streptococcus pyogenes* MGAS8232 chromosome, complete genome," (2002) 460 pages, entry downloaded from ncbi.nlm.nih.gov on Nov. 17, 2011.

Lazarevic, V. et al., Accession No. NC_001884, "*Bacillus* phage SPBc2, complete genome," (2000), 94 pages, entry downloaded from ncbi.nlm.nih.gov on Nov. 17, 2011.

Ferretti, J.J. et al., "Complete genome sequence of an M1 strain of *Streptococcus pyogenes*," *PNAS* 98(8):4658-4663, National Academy of Sciences, United States (2001).

Sciochetti, S.A., et al., "The ripX Locus of *Bacillus subtilis* Encodes a Site-Specific Recombinase Involved in Proper Chromosome Partitioning," *Journal of Bacteriology* 181(19):6053-6062, American Society for Microbiology, United States (1999).

Office Action mailed Jan. 29, 2014 in U.S. Appl. No. 11/841,426, filed Aug. 20, 2007, inventors T. Reed et al.

Ferretti, J.J. et al., "*Streptococcus pyogenes* SF370 chromosome, complete genome," entry downloaded from ncbi.nlm.nih.gov/nuccore/ NC_002737 on Mar. 18, 2014.

Mcdiavilla, J. et al., "*Mycobacterium* Bxb1, complete sequence," GenBank Database Accession No. AF271693.1 (2001), downloaded on Apr. 29, 2014 from ncbi.nlm.nih.gov/nuccore/af271693.

Yu, S. and W.R. Jacobs, "*Mycobacterium bovis* BCG"putative adenosylmethionine-8-amino-7-oxononanoate aminotransferase (bioA), putative 8-amino-7-oxononanoate synthase (bioF), putative dethiobiotin synthetase (bioD), and biotin synthetase (bioB) genes, complete cds, GenBank Database Accession No. AF041819.1 (1998), downloaded on Apr. 29, 2014 from ncbi.nlm.nih.gov/nuccore/af041819.

Office Action mailed May 6, 2014 in U.S. Appl. No. 11/841,426, filed Aug. 20, 2007, inventor Malla Padidam.

\* cited by examiner

SF370.1 attP site, (SEQ ID No: 14), 99 bp
ACGAAAGGAGGTCGTGAAATGGATAAAAAAATACAGCGTTTTTCATGTACAACTATACTAGTTGTAGTGCCTAAATAATGCTTTTAAAACTTAAAAATA
                                            X
GTTTTGGAAAAACTCTAGGCAGTTTCCCTGAATCCCAAGCAGGCTTGTTCAGGCTTACTATTTAGAGAAAATGGGTCTGACCTGGAGAGTCAGTATTTA
Pseudo attB site on human chromosome 10 (SEQ ID No: 22)

↓ Recombinase

ACGAAAGGAGGTCGTGAAATGGATAAAAAAATACAGCGTTTTTCATGTACAACTATACTATTTAGAGAAAATGGGTCTGACCTGGAGAGTCAGTATTTA
Pseudo attR site after integration of target plasmid (SEQ ID No: 23)

SPβc2 attP site, (SEQ ID No: 11), 99 bp
ACGGCAGAGTAAGCTTCTTTTTTTCGTTAGATATGTAGTAAGTATCTTAATATACAGCTTTATCTGTTTTTTAAGATACTTACTACTTTTCTTAGTGGA
                                            X
ATAAGCACAGGAACAAACTCATAAGAGCCTGCAATGAGATCATCAGTGTCAAGCACTCATTATAGTGCTTGGCATACACCAAATGTTCAGGAGAGATCT
Pseudo attB site on human chromosome 15 (SEQ ID No: 24)

↓ Recombinase

ACGGCAGAGTAAGCTTCTTTTTTTCGTTAGATATGTAGTAAGTATCTTAATATACAGCTTTATAGTGCTTGGCATACACCAAATGTTCAGGAGAGATCT
Pseudo attR site after integration of target plasmid (SEQ ID No: 25)

Figure 14

SITE-SPECIFIC SERINE RECOMBINASES AND METHODS OF THEIR USE

STATEMENT REGARDING FEDERALLY SPONSORED RESEARCH

This invention was made with government support under Grant No. 70NANB1H3062, awarded by National Institute of Standards and Technology, Advance Technology Program. The Government may have certain rights in the invention.

REFERENCE TO SEQUENCE LISTING SUBMITTED ELECTRONICALLY VIA EFS-WEB

This application includes a "Sequence_Listing.ST25.txt," 37,920 bytes, created on Oct. 28, 2009, and modified on Apr. 8, 2010, and submitted electronically via EFS-Web, which is hereby incorporated by reference in its entirety.

FIELD OF THE INVENTION

The present invention relates to the field of genetic engineering. Specifically the invention relates to compositions and methods for site-specifically integrating, deleting, inverting, exchanging, and translocating a polynucleotide into the genome of a cell. The invention also relates to enzyme, polynucleotides, polypeptides, and vector constructs.

BACKGROUND OF THE INVENTION

Many bacteriophage and integrative plasmids encode site-specific recombination systems that enable the stable incorporation of their genome into those of their hosts and excision of the genome from the host genome. In these systems, the minimal requirements for the recombination reaction are a recombinase enzyme, which catalyzes the recombination event, and two recombination sites (Sadowski (1986) J. Bacteriol. 165: 341-347; Sadowski (1993) FASEB J. 7: 760-767). For phage integration systems, these are referred to as attachment (att) sites, with an attP element from phage DNA and the attB element present in the bacterial genome. The two attachment sites can share as little sequence identity as a few base pairs. The recombinase protein binds to both att sites and catalyzes a conservative and reciprocal exchange of DNA strands that result in integration of the circular phage or plasmid DNA into host DNA. Additional phage or host factors, such as the DNA bending protein IHF, integration host factor, may be required for an efficient reaction (Friedman (1988) Cell 55:545-554; Finkel & Johnson (1992) Mol. Microbiol. 6: 3257-3265). Phage integrases, in association with other host and/or phage factors, also excise the phage genome from the bacterial genome during the lytic phase of bacteriophages growth cycle. Several methods have been developed allowing the manipulation of mammalian genomes in order to elucidate the relevance and function of particular genes of interest. Among them, the development of transgenic mouse strains and gene-targeting technologies have turned out to be particularly useful (Brandon, E. P., Idzerda, R. L. and McKnight, G. S. (1995) Curr Biol, 5, 625-34; Brandon, E. P., Idzerda, R. L. and McKnight, G. S. (1995) Curr Biol, 5, 758-65). These techniques have undergone a new advance with the characterization and application of site-specific recombinases (Kilby, N. J., Snaith, M. R. and Murray, J. A. (1993) Trends Genet, 9, 413-21).

Site-specific recombinases can be separated into two major families. The first one (the Int family or tyrosine recombinase family) comprises those enzymes that catalyze recombination between sites located either in the same DNA molecule (intramolecular recombination leading to resolution, excision, or inversion) or in separate DNA molecules (intermolecular recombination leading to integration) (Sauer, B. (1993) Methods Enzymol, 225, 890-900; Dymecki, S. M. (1996) Proc Natl Acad Sci USA, 93, 6191-6; Abremski, K. and Hoess, R. (1984) J Biol Chem 259, 1509-14; Nash, H. A. (1996) in Escherichia coli and Salmonella cellular and molecular biology., ed. F. C. Neidhart, R. I. Curtis, J. L. Ingraham, E. C. C. Lin, K. B. Low, B. Magasanik, W. S. Rezaikoff, M. Riley, M. Schaechter and H. E. Umbager (A. S. M. Press, Washington D.C.), pp. 2363-7). The latter property has been exploited to allow targeted insertion of specific sequences in precise locations (Sauer, B. and Henderson, N. (1990) The New Biologist, 2, 441-9; Fukushige, S. and Sauer, B. (1992) Proc. Natl. Acad. Sci. USA, 89, 7905-9). The recombinases that have been used for manipulating mammalian genomes have been mainly the Cre and the Flp proteins, which belong to the Int family (Kilby, N. J., Snaith, M. R. and Murray, J. A. (1993) Trends Genet, 9, 413-21). The target sequences for these enzymes, named loxP sites for the Cre enzyme and FRT for the Flp enzyme, consist of a short inverted repeat to which the protein binds. The recombination process is operative through long distances (up to 70 kb) in the genome. Using these enzymes, several authors have reported site- and tissue-specific DNA recombination in murine models (DiSanto, J. P., Muller, W., Guy, G. D., Fischer, A. and Rajewsky, K. (1995) Proc Natl Acad Sci USA, 92, 377-81; Gu, H., Marth, J. D., Orban, P. C., Mossmann, H. and Rajewsky, K. (1994) Science, 265, 103-6; Kuhn, R., Schwenk, F., Aguet, M. and Rajewsky, K. (1995) Science, 269, 1427-9; Orban, P. C., Chui, D. and Marth, J. D. (1992) Proc. Natl. Acad. Sci. USA, 89, 6861-5), chromosomal translocations in plants and animals (Deursen, J. v., Fornerod, M., Rees, B. v. and Grosveld, G. (1995) Proc. Natl. Acad. Sci. USA, 92, 7376-80; Medberry, S. L., Dale, E., Qin, M. and Ow, D. W. (1995) Nucleic Acids Res, 23, 485-90; Osborne, B. I., Wirtz, U. and Baker, B. (1995) Plant J, 7, 687-701) and targeted induction of specific genes (Pichel, J. G., Lakso, M. and Westphal, H. (1993) Oncogene, 8, 3333-42). The Cre-loxP system has also been used in combination with inducible promoters, such as the interferon gamma inducible promoter, that was used to provoke gene ablation in liver with high efficiency and to a less extent in other tissues (Kuhn, R., Schwenk, F., Aguet, M. and Rajewsky, K. (1995) Science, 269, 1427-9). This site-specific recombination system, however, only allows the induction of a reduced number of recombination events in the same genome. Since each recombination reaction leaves a target sequence for the recombinase in the genome at the crossover site, and because recombinases (e.g. Cre and Flp) can catalyze intermolecular recombination, the whole process may lead to undesired chromosomal rearrangements.

The second family of recombinases are collectively termed resolvases/invertases family or serine family (Grindley, N. D. F. (1994) in Nucleic Acids and Molecular Biology, ed. F. Eckstein and D. M. J. Lilley (Springer-Verlag, Berlin), pp. 236-67, (Smith, M. C. and Thorpe, H. M. (2000) Mol. Microbiol., 44, 299-307)). These site-specific recombinases, which include enzymes that catalyze intramolecular and intermolecular reactions, could have an advantage over the Int family of recombinases. Serine recombinases that catalyze phage integration (integrases) are especially well adapted for use as genetic engineering tools. So far three serine recombinases, φC31, R4 and TP901-1, have been examined in mammalian cells (Groth, A. C. and Calos, M. P. (2004) J. Mol. Biol. 335, 667-678). These recombinases were observed to be autonomous, to have simple att sequences and have the ability to function in mammalian cells. As little or no recombination between any combination of sites other than attP or attB has been observed, the integrations are unidirectional and there is a high integration frequency. Serine recombinases provide a significant advantage over the prior recombination systems employing the use of members of the Int family of recombinases. These enzymes have numerous applications. One way is the placement of att sites into the genome of an organism and use as targets for recombination.

Applicant has identified novel serine recombinases that demonstrate robust activity in various mammalian cells and in plant cells, as well as the ability to stably integrate a polynucleotide into the genome of a host cell or excise a polynucleotide from the genome of a host cell.

SUMMARY OF THE INVENTION

The present invention provides compositions and methods for obtaining stable, site-specific recombination in a eukaryotic cell. Contrary to previously described methods for site-specific recombination, the present recombinases and methods of their use provide for stable, irreversible, site-specific recombination.

The compositions of the present invention provide for a recombinase polypeptide that mediates site-specific recombination between a first recombination site and a second recombination site. In some embodiments, the nucleic acids further include recombination sites recognized by the recombinase polypeptide.

The methods involve providing a eukaryotic cell that comprises a first recombination site and a second recombination site, which second recombination site can serve as a substrate for recombination with the first recombination site. The first and the second recombination sites are contacted with a prokaryotic recombinase polypeptide, resulting in recombination between the recombination sites. Either or both of the recombination sites can be present in a chromosome of the eukaryotic cell. In some embodiments, one of the recombination sites is present in the chromosome and the other is included within a nucleic acid that is to be integrated into the chromosome.

The invention also provides eukaryotic cells that contain a prokaryotic recombinase polypeptide or a nucleic acid that encodes a prokaryotic recombinase. In these embodiments, the recombinase can mediate site-specific recombination between a first recombination site and a second recombination site that can serve as a substrate for recombination with the first recombination site. In preferred embodiments the recombinases are selected from the group consisting of a *Listeria monocytogenes* phage, a *Streptococcus pyogenes* phage, a *Bacillus subtilis* phage, a *Mycobacterium tuberculosis* phage and a *Mycobacterium smegmatis* phage. More preferably, the recombinase is selected from the group consisting of A118 recombinase, SF370.1 recombinase, SPβc2 recombinase, φRv1 recombinase, and Bxb1 recombinase.

In additional embodiments, the invention provides methods for obtaining a eukaryotic cell having a stably integrated polynucleotide sequence. These methods involve introducing a nucleic acid into a eukaryotic cell that comprises a first recombination site, wherein the nucleic acid comprises the transgene of interest and a second recombination site which can serve as a substrate for recombination with the first recombination site. The first and second recombination sites are contacted with a prokaryotic recombinase polypeptide. The recombinase polypeptide catalyzes recombination between the first and second recombination sites, resulting in integration of the nucleic acid at the first recombination site.

The ability of phage recombinases to specifically and efficiently direct recombination between DNA sequences in living cells makes them potentially useful in a variety of genetic engineering applications. Such applications include integration, excision, inversion, translocation and cassette exchange of polynucleotide sequences.

BRIEF DESCRIPTION OF THE DRAWINGS

FIG. 14 demonstrates the nucleotide sequences of native pseudo attB sites for SF370.1 and SPβc2 recombinases identified in HEK293 cells.

DESCRIPTION OF THE PREFERRED EMBODIMENT

Definitions

Figure 1:
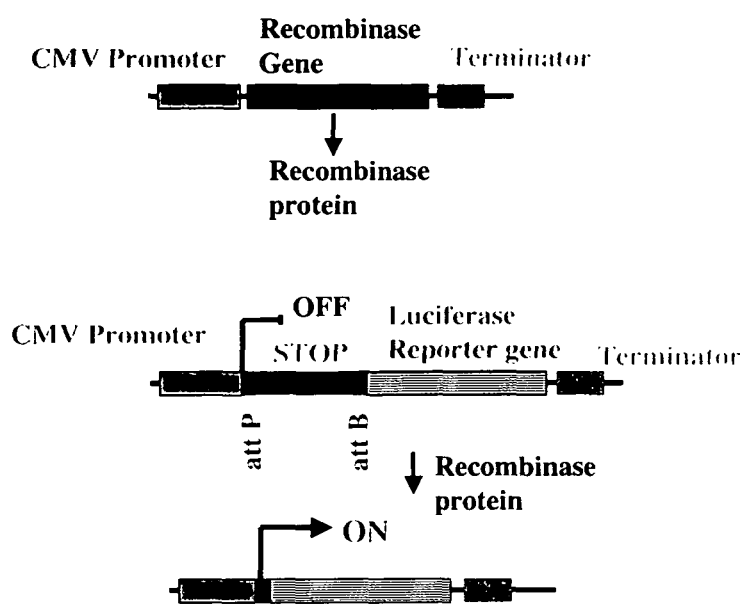
FIG. 1 depicts a schematic representation of the Transient Intramolecular Recombination Assay (TIRA) used to assay the ability of the recombinase to detect recombination between attP and attB sites on a target or assay plasmid as described in the Examples.

In this disclosure, a number of terms and abbreviations are used. The following definitions are provided and should be helpful in understanding the scope and practice of the present invention.

In a specific embodiment, the term "about" or "approximately" means within 20%, preferably within 10%, more preferably within 5%, and even more preferably within 1% of a given value or range.

"Recombinase" as used herein refers to a group of enzymes that can facilitate site-specific recombination between defined sites, where the sites are physically separated on a single DNA molecule or where the sites reside on separate DNA molecules. The DNA sequences of the defined recombination sites are not necessarily identical. Initiation of recombination depends on protein-DNA interaction, within the group there are large number of proteins that catalyze phage integration and excision (e.g., λ integrase, φC31), resolution of circular plasmids (e.g., Tn3, gamma delta, Cre, Flp), DNA inversion for expression of alternate genes (e.g., Hin, Gin, Pin), assembly of genes during development (e.g., Anabaena nitrogen fixation genes), and transposition (e.g., IS607 transposon). Most site-specific recombinases fall into one of the two families, based on evolutionary and mechanistic relatedness. These are λ integrase family or tyrosine recombinases (e.g., Cre, Flp, Xer D) and resolvase/integrase family or serine recombinase family (e.g., φC31, TP901-1, Tn3, gamma delta).

"Recombination attachment sites" are specific polynucleotide sequences that are recognized by the recombinase enzymes described herein. Typically, two different sites are involved (termed "complementary sites"), one present in the target nucleic acid (e.g., a chromosome or episome of a eukaryote or prokaryote) and another on the nucleic acid that is to be integrated at the target recombination site. The terms "attB" and "attP," which refer to attachment (or recombination) sites originally from a bacterial target and a phage donor, respectively, are used herein although recombination sites for particular enzymes may have different names. The recombination sites typically include left and right arms separated by a core or spacer region. Thus, an attB recombination site consists of BOB', where B and B' are the left and right arms, respectively, and O is the core region. Similarly, attP is POP', where P and P' are the arms and O is again the core region. Upon recombination between the attB and attP sites, and concomitant integration of a nucleic acid at the target, the recombination sites that flank the integrated DNA are referred to as "attL" and "attR." The attL and attR sites, using the terminology above, thus consist of BOP' and POB', respectively. In some representations herein, the "O" is omitted and attB and attP, for example, are designated as BB' and PP', respectively.

The term "substantially free" means that a composition comprising "A" (where "A" is a single protein, DNA molecule, vector, recombinant host cell, etc.) is substantially free of "B" (where "B" comprises one or more contaminating proteins, DNA molecules, vectors, etc.) when at least about 75% by weight of the proteins, DNA, vectors (depending on the category of species to which A and B belong) in the composition is "A". Preferably, "A" comprises at least about 90% by weight of the A+B species in the composition, most preferably at least about 99% by weight. It is also preferred that a composition, which is substantially free of contamination, contain only a single molecular weight species having the activity or characteristic of the species of interest.

The term "isolated" for the purposes of the present invention designates a biological material (nucleic acid or protein) that has been removed from its original environment (the environment in which it is naturally present). For example, a polynucleotide present in the natural state in a plant or an animal is not isolated, however the same polynucleotide separated from the adjacent nucleic acids in which it is naturally present, is considered "isolated". The term "purified" does not require the material to be present in a form exhibiting absolute purity, exclusive of the presence of other compounds. It is rather a relative definition.

A polynucleotide is in the "purified" state after purification of the starting material or of the natural material by at least one order of magnitude, preferably 2 or 3 and preferably 4 or 5 orders of magnitude.

A "nucleic acid" is a polymeric compound comprised of covalently linked subunits called nucleotides. Nucleic acid includes polyribonucleic acid (RNA) and polydeoxyribonucleic acid (DNA), both of which may be single-stranded or double-stranded. DNA includes but is not limited to cDNA, genomic DNA, plasmids DNA, synthetic DNA, and semi-synthetic DNA. DNA may be linear, circular, or supercoiled.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA). A "recombinant DNA molecule" is a DNA molecule that has undergone a molecular biological manipulation.

The term "fragment" will be understood to mean a nucleotide sequence of reduced length relative to the reference nucleic acid and comprising, over the common portion, a nucleotide sequence identical to the reference nucleic acid. Such a nucleic acid fragment according to the invention may be, where appropriate, included in a larger polynucleotide of which it is a constituent. Such fragments comprise, or alternatively consist of, oligonucleotides ranging in length from at least 6, 8, 9, 10, 12, 15, 18, 20, 21, 22, 23, 24, 25, 30, 39, 40, 42, 45, 48, 50, 51, 54, 57, 60, 63, 66, 70, 75, 78, 80, 90, 100, 105, 120, 135, 150, 200, 300, 500, 720, 900, 1000 or 1500 consecutive nucleotides of a nucleic acid according to the invention.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A "gene" refers to an assembly of nucleotides that encode a polypeptide, and includes cDNA and genomic DNA nucleic acids. "Gene" also refers to a nucleic acid fragment that expresses a specific protein or polypeptide, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and/or coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A chimeric gene may comprise coding sequences derived from different sources and/or regulatory sequences derived from different sources. "Endogenous gene" refers to a native gene in its natural location in the genome of an organism. A "foreign" gene or "heterologous" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Heterologous" DNA refers to DNA not naturally located in the cell, or in a chromosomal site of the cell. Preferably, the heterologous DNA includes a gene foreign to the cell.

The term "genome" includes chromosomal as well as mitochondrial, chloroplast and viral DNA or RNA.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., 1989 infra). Hybridization and washing conditions are well known and exemplified in Sambrook, J., Fritsch, E. F. and Maniatis, T. *Molecular Cloning: A Laboratory Manual*, Second Edition, Cold Spring Harbor Laboratory Press, Cold Spring Harbor (1989), particularly Chapter 11 and Table 11.1 therein (entirely incorporated herein by reference). The conditions of temperature and ionic strength determine the "stringency" of the hybridization.

Stringency conditions can be adjusted to screen for moderately similar fragments, such as homologous sequences from distantly related organisms, to highly similar fragments, such as genes that duplicate functional enzymes from closely related organisms. For preliminary screening for homologous nucleic acids, low stringency hybridization conditions, corresponding to a $T_m$ of 55°, can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC.

Hybridization requires that the two nucleic acids contain complementary sequences, although depending on the stringency of the hybridization, mismatches between bases are possible. The term "complementary" is used to describe the relationship between nucleotide bases that are capable of hybridizing to one another. For example, with respect to DNA, adenosine is complementary to thymine and cytosine is complementary to guanine. Accordingly, the instant invention also includes isolated nucleic acid fragments that are complementary to the complete sequences as disclosed or used herein as well as those substantially similar nucleic acid sequences.

In a specific embodiment of the invention, polynucleotides are detected by employing hybridization conditions comprising a hybridization step at $T_m$ of 55° C., and utilizing conditions as set forth above. In a preferred embodiment, the $T_m$ is 60° C.; in a more preferred embodiment, the $T_m$ is 63° C.; in an even more preferred embodiment, the $T_m$ is 65° C.

Post-hybridization washes also determine stringency conditions. One set of preferred conditions uses a series of washes starting with 6×SSC, 0.5% SDS at room temperature for 15 minutes (min), then repeated with 2×SSC, 0.5% SDS at 45° C. for 30 minutes, and then repeated twice with 0.2×SSC, 0.5% SDS at 50° C. for 30 minutes. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. Hybridization requires that the two nucleic acids comprise complementary sequences, although depending on the stringency of the hybridization, mismatches between bases are possible.

The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50-0.51). For hybridization with shorter nucleic acids, i.e., oligonucleotides, the position of mismatches becomes more important, and the length of the oligonucleotide determines its specificity (see Sambrook et al., supra, 11.7-11.8).

In a specific embodiment of the invention, polynucleotides are detected by employing hybridization conditions comprising a hybridization step in less than 500 mM salt and at least 37 degrees Celsius, and a washing step in 2×SSPE at at least 63 degrees Celsius. In a preferred embodiment, the hybridization conditions comprise less than 200 mM salt and at least 37 degrees Celsius for the hybridization step. In a more preferred embodiment, the hybridization conditions comprise 2×SSPE and 63 degrees Celsius for both the hybridization and washing steps.

In one embodiment, the length for a hybridizable nucleic acid is at least about 10 nucleotides. Preferably a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

The term "probe" refers to a single-stranded nucleic acid molecule that can base pair with a complementary single stranded target nucleic acid to form a double-stranded molecule.

As used herein, the term "oligonucleotide" refers to a nucleic acid, generally of at least 18 nucleotides, that is hybridizable to a genomic DNA molecule, a cDNA molecule, a plasmid DNA or an mRNA molecule. Oligonucleotides can be labeled, e.g., with $^{32}$P-nucleotides or nucleotides to which a label, such as biotin, has been covalently conjugated. A labeled oligonucleotide can be used as a probe to detect the presence of a nucleic acid. Oligonucleotides (one or both of which may be labeled) can be used as PCR primers, either for cloning full length or a fragment of a nucleic acid, or to detect the presence of a nucleic acid. An oligonucleotide can also be used to form a triple helix with a DNA molecule. Generally, oligonucleotides are prepared synthetically, preferably on a nucleic acid synthesizer. Accordingly, oligonucleotides can be prepared with non-naturally occurring phosphoester analog bonds, such as thioester bonds, etc.

A "primer" is an oligonucleotide that hybridizes to a target nucleic acid sequence to create a double stranded nucleic acid region that can serve as an initiation point for DNA synthesis under suitable conditions. Such primers may be used in a polymerase chain reaction.

"Polymerase chain reaction" is abbreviated PCR and means an in vitro method for enzymatically amplifying specific nucleic acid sequences. PCR involves a repetitive series of temperature cycles with each cycle comprising three stages: denaturation of the template nucleic acid to separate the strands of the target molecule, annealing a single stranded PCR oligonucleotide primer to the template nucleic acid, and extension of the annealed primer(s) by DNA polymerase. PCR provides a means to detect the presence of the target molecule and, under quantitative or semi-quantitative conditions, to determine the relative amount of that target molecule within the starting pool of nucleic acids.

"Reverse transcription-polymerase chain reaction" is abbreviated RT-PCR and means an in vitro method for enzymatically producing a target cDNA molecule or molecules from an RNA molecule or molecules, followed by enzymatic amplification of a specific nucleic acid sequence or sequences within the target cDNA molecule or molecules as described above. RT-PCR also provides a means to detect the presence of the target molecule and, under quantitative or semi-quantitative conditions, to determine the relative amount of that target molecule within the starting pool of nucleic acids.

A DNA "coding sequence" is a double-stranded DNA sequence that is transcribed and translated into a polypeptide in a cell in vitro or in vivo when placed under the control of appropriate regulatory sequences. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure. The boundaries of the coding sequence are determined by a start codon at the 5' (amino) terminus and a translation stop codon at the 3' (carboxyl) terminus. A coding sequence can include, but is not limited to, prokaryotic sequences, cDNA from mRNA, genomic DNA sequences, and even synthetic DNA sequences. If the coding sequence is intended for expression in a eukaryotic cell, a polyadenylation signal and transcription termination sequence will usually be located 3' to the coding sequence.

"Open reading frame" is abbreviated ORF and means a length of nucleic acid sequence, either DNA, cDNA or RNA, that comprises a translation start signal or initiation codon, such as an ATG or AUG, and a termination codon and can be potentially translated into a polypeptide sequence.

The term "head-to-head" is used herein to describe the orientation of two polynucleotide sequences in relation to each other. Two polynucleotides are positioned in a head-to-head orientation when the 5' end of the coding strand of one polynucleotide is adjacent to the 5' end of the coding strand of the other polynucleotide, whereby the direction of transcription of each polynucleotide proceeds away from the 5' end of the other polynucleotide. The term "head-to-head" may be abbreviated (5')-to-(5') and may also be indicated by the symbols (←→) or (3'←5'5'→3').

The term "tail-to-tail" is used herein to describe the orientation of two polynucleotide sequences in relation to each other. Two polynucleotides are positioned in a tail-to-tail orientation when the 3' end of the coding strand of one polynucleotide is adjacent to the 3' end of the coding strand of the other polynucleotide, whereby the direction of transcription of each polynucleotide proceeds toward the other polynucleotide. The term "tail-to-tail" may be abbreviated (3')-to-(3') and may also be indicated by the symbols (→←) or (5'→3'3'←5').

The term "head-to-tail" is used herein to describe the orientation of two polynucleotide sequences in relation to each other. Two polynucleotides are positioned in a head-to-tail orientation when the 5' end of the coding strand of one polynucleotide is adjacent to the 3' end of the coding strand of the other polynucleotide, whereby the direction of transcription of each polynucleotide proceeds in the same direction as that of the other polynucleotide. The term "head-to-tail" may be abbreviated (5')-to-(3') and may also be indicated by the symbols (→→) or (5'→3'5'←3').

The term "downstream" refers to a nucleotide sequence that is located 3' to reference nucleotide sequence. In particular, downstream nucleotide sequences generally relate to sequences that follow the starting point of transcription. For example, the translation initiation codon of a gene is located downstream of the start site of transcription.

The term "upstream" refers to a nucleotide sequence that is located 5' to reference nucleotide sequence. In particular, upstream nucleotide sequences generally relate to sequences that are located on the 5' side of a coding sequence or starting point of transcription. For example, most promoters are located upstream of the start site of transcription.

The terms "restriction endonuclease" and "restriction enzyme" refer to an enzyme that binds and cuts within a specific nucleotide sequence within double stranded DNA.

"Homologous recombination" refers to the insertion of a foreign DNA sequence into another DNA molecule, e.g., insertion of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

Several methods known in the art may be used to propagate a polynucleotide according to the invention. Once a suitable host system and growth conditions are established, recombinant expression vectors can be propagated and prepared in quantity. As described herein, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

A "vector" is any means for the cloning of and/or transfer of a nucleic acid into a host cell. A vector may be a replicon to which another DNA segment may be attached so as to bring about the replication of the attached segment. A "replicon" is any genetic element (e.g., plasmid, phage, cosmid, chromosome, virus) that functions as an autonomous unit of DNA replication in vivo, i.e., capable of replication under its own control. The term "vector" includes both viral and nonviral means for introducing the nucleic acid into a cell in vitro, ex vivo or in vivo. A large number of vectors known in the art may be used to manipulate nucleic acids, incorporate response elements and promoters into genes, etc. Possible vectors include, for example, plasmids or modified viruses including, for example bacteriophages such as lambda derivatives, or plasmids such as pBR322 or pUC plasmid derivatives, or the Bluescript vector. For example, the insertion of the DNA fragments corresponding to response elements and promoters into a suitable vector can be accomplished by ligating the appropriate DNA fragments into a chosen vector that has complementary cohesive termini. Alternatively, the ends of the DNA molecules may be enzymatically modified or any site may be produced by ligating nucleotide sequences (linkers) into the DNA termini. Such vectors may be engineered to contain selectable marker genes that provide for the selection of cells that have incorporated the marker into the cellular genome. Such markers allow identification and/or selection of host cells that incorporate and express the proteins encoded by the marker.

Viral vectors, and particularly retroviral vectors, have been used in a wide variety of gene delivery applications in cells, as well as living animal subjects. Viral vectors that can be used include but are not limited to retrovirus, adeno-associated virus, pox, baculovirus, vaccinia, herpes simplex, Epstein-Barr, adenovirus, geminivirus, and caulimovirus vectors. Non-viral vectors include plasmids, liposomes, electrically charged lipids (cytofectins), DNA-protein complexes, and biopolymers. In addition to a nucleic acid, a vector may also comprise one or more regulatory regions, and/or selectable markers useful in selecting, measuring, and monitoring nucleic acid transfer results (transfer to which tissues, duration of expression, etc.).

The term "plasmid" refers to an extra chromosomal element often carrying a gene that is not part of the central metabolism of the cell, and usually in the form of circular double-stranded DNA molecules. Such elements may be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

A "cloning vector" is a "replicon", which is a unit length of a nucleic acid, preferably DNA, that replicates sequentially and which comprises an origin of replication, such as a plasmid, phage or cosmid, to which another nucleic acid segment may be attached so as to bring about the replication of the attached segment. Cloning vectors may be capable of replication in one cell type and expression in another ("shuttle vector").

Vectors may be introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., 1992, J. Biol. Chem. 267: 963-967; Wu and Wu, 1988, J. Biol. Chem. 263: 14621-14624; and Hartmut et al., Canadian Patent Application No. 2,012,311, filed Mar. 15, 1990).

A polynucleotide according to the invention can also be introduced in vivo by lipofection. For the past decade, there has been increasing use of liposomes for encapsulation and transfection of nucleic acids in vitro. Synthetic cationic lipids designed to limit the difficulties and dangers encountered with liposome-mediated transfection can be used to prepare liposomes for in vivo transfection of a gene encoding a marker (Felgner et al., 1987, Proc. Natl. Acad. Sci. U.S.A. 84: 7413; Mackey, et al., 1988, Proc. Natl. Acad. Sci. U.S.A. 85:8027-8031; and Ulmer et al., 1993, Science 259: 1745-1748). The use of cationic lipids may promote encapsulation of negatively charged nucleic acids, and also promote fusion with negatively charged cell membranes (Felgner and Ringold, 1989, Science 337:387-388). Particularly useful lipid compounds and compositions for transfer of nucleic acids are described in International Patent Publications WO95/18863 and WO96/17823, and in U.S. Pat. No. 5,459,127. The use of lipofection to introduce exogenous genes into the specific organs in vivo has certain practical advantages. Molecular targeting of liposomes to specific cells represents one area of benefit. It is clear that directing transfection to particular cell types would be particularly preferred in a tissue with cellular heterogeneity, such as pancreas, liver, kidney, and the brain. Lipids may be chemically coupled to other molecules for the purpose of targeting (Mackey, et al., 1988, supra). Targeted peptides, e.g., hormones or neurotransmitters, and proteins such as antibodies, or non-peptide molecules could be coupled to liposomes chemically.

Other molecules are also useful for facilitating transfection of a nucleic acid in vivo, such as a cationic oligopeptide (e.g., WO95/21931), peptides derived from DNA binding proteins (e.g., WO96/25508), or a cationic polymer (e.g., WO95/21931).

It is also possible to introduce a vector in vivo as a naked DNA plasmid (see U.S. Pat. Nos. 5,693,622, 5,589,466 and 5,580,859). Receptor-mediated DNA delivery approaches can also be used (Curiel et al., 1992, Hum. Gene Ther. 3: 147-154; and Wu and Wu, 1987, J. Biol. Chem. 262: 4429-4432).

The term "transfection" means the uptake of exogenous or heterologous RNA or DNA by a cell. A cell has been "transfected" by exogenous or heterologous RNA or DNA when such RNA or DNA has been introduced inside the cell. A cell has been "transformed" by exogenous or heterologous RNA or DNA when the transfected RNA or DNA effects a phenotypic change. The transforming RNA or DNA can be integrated (covalently linked) into chromosomal DNA making up the genome of the cell.

"Transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

The term "genetic region" will refer to a region of a nucleic acid molecule or a nucleotide sequence that comprises a gene encoding a polypeptide.

In addition, the recombinant vector comprising a polynucleotide according to the invention may include one or more origins for replication in the cellular hosts in which their amplification or their expression is sought, markers or selectable markers.

The term "selectable marker" means an identifying factor, usually an antibiotic or chemical resistance gene, that is able to be selected for based upon the marker gene's effect, i.e., resistance to an antibiotic, resistance to a herbicide, colorimetric markers, enzymes, fluorescent markers, and the like, wherein the effect is used to track the inheritance of a nucleic acid of interest and/or to identify a cell or organism that has inherited the nucleic acid of interest. Examples of selectable marker genes known and used in the art include: genes providing resistance to ampicillin, streptomycin, gentamycin, kanamycin, hygromycin, bialaphos herbicide, sulfonamide, and the like; and genes that are used as phenotypic markers, i.e., anthocyanin regulatory genes, isopentanyl transferase gene, and the like.

The term "reporter gene" means a nucleic acid encoding an identifying factor that is able to be identified based upon the reporter gene's effect, wherein the effect is used to track the inheritance of a nucleic acid of interest, to identify a cell or organism that has inherited the nucleic acid of interest, and/or to measure gene expression induction or transcription. Examples of reporter genes known and used in the art include: luciferase (Luc), green fluorescent protein (GFP), chloramphenicol acetyltransferase (CAT), β-galactosidase (LacZ), β-glucuronidase (Gus), and the like. Selectable marker genes may also be considered reporter genes.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters". Promoters that cause a gene to be expressed in a specific cell type are commonly referred to as "cell-specific promoters" or "tissue-specific promoters". Promoters that cause a gene to be expressed at a specific stage of development or cell differentiation are commonly referred to as "developmentally-specific promoters" or "cell differentiation-specific promoters". Promoters that are induced and cause a gene to be expressed following exposure or treatment of the cell with an agent, biological molecule, chemical, ligand, light, or the like that induces the promoter are commonly referred to as "inducible promoters" or "regulatable promoters". It is further recognized that since in most cases the exact boundaries of regulatory sequences have not been completely defined, DNA fragments of different lengths may have identical promoter activity.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced (if the coding sequence contains introns) and translated into the protein encoded by the coding sequence.

"Transcriptional and translational control sequences" are DNA regulatory sequences, such as promoters, enhancers, terminators, and the like, that provide for the expression of a coding sequence in a host cell. In eukaryotic cells, polyadenylation signals are control sequences.

The term "response element" means one or more cis-acting DNA elements which confer responsiveness on a promoter mediated through interaction with the DNA-binding domains of the first chimeric gene. This DNA element may be either palindromic (perfect or imperfect) in its sequence or composed of sequence motifs or half sites separated by a variable number of nucleotides. The half sites can be similar or identical and arranged as either direct or inverted repeats or as a single half site or multimers of adjacent half sites in tandem. The response element may comprise a minimal promoter isolated from different organisms depending upon the nature of the cell or organism into which the response element will be incorporated. The DNA binding domain of the first hybrid protein binds, in the presence or absence of a ligand, to the DNA sequence of a response element to initiate or suppress transcription of downstream gene(s) under the regulation of this response element. Examples of DNA sequences for response elements of the natural ecdysone receptor include: RRGG/TTCANTGAC/ACYY, (SEQ ID NO:26), (see Cherbas L., et. al., (1991), *Genes Dev.* 5, 120-131); AGGTCAN$_{(n)}$AGGTCA, (SEQ ID NO:27), where N$_{(n)}$ can be one or more spacer nucleotides (see D'Avino P P., et. al., (1995), *Mol. Cell. Endocrinol,* 113, 1-9); and GGGTTGAATGAATTT (SEQ ID NO:28), (see Antoniewski C., et. al., (1994). *Mol. Cell Biol.* 14, 4465-4474).

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from a nucleic acid or polynucleotide. Expression may also refer to translation of mRNA into a protein or polypeptide.

The terms "cassette", "expression cassette" and "gene expression cassette" refer to a segment of DNA that can be inserted into a nucleic acid or polynucleotide at specific restriction sites or by homologous recombination. The segment of DNA comprises a polynucleotide that encodes a polypeptide of interest, and the cassette and restriction sites are designed to ensure insertion of the cassette in the proper reading frame for transcription and translation. "Transformation cassette" refers to a specific vector comprising a polynucleotide that encodes a polypeptide of interest and having elements in addition to the polynucleotide that facilitate transformation of a particular host cell. Cassettes, expression cassettes, gene expression cassettes and transformation cassettes of the invention may also comprise elements that allow for enhanced expression of a polynucleotide encoding a polypeptide of interest in a host cell. These elements may include, but are not limited to: a promoter, a minimal promoter, an enhancer, a response element, a terminator sequence, a polyadenylation sequence, and the like.

The terms "modulate" and "modulates" mean to induce, reduce or inhibit nucleic acid or gene expression, resulting in the respective induction, reduction or inhibition of protein or polypeptide production.

The plasmids or vectors according to the invention may further comprise at least one promoter suitable for driving expression of a gene in a host cell. The term "expression vector" means a vector, plasmid or vehicle designed to enable the expression of an inserted nucleic acid sequence following transformation into the host. The cloned gene, i.e., the inserted nucleic acid sequence, is usually placed under the control of control elements such as a promoter, a minimal promoter, an enhancer, or the like. Initiation control regions or promoters, which are useful to drive expression of a nucleic acid in the desired host cell are numerous and familiar to those skilled in the art. Virtually any promoter capable of driving these genes is suitable for the present invention including but not limited to: viral promoters, bacterial promoters, animal promoters, mammalian promoters, synthetic promoters, constitutive promoters, tissue specific promoter, developmental specific promoters, inducible promoters, light regulated promoters; CYC1, HIS3, GAL1, GAL4, GAL10, ADH1, PGK, PHO5, GAPDH, ADC1, TRP1, URA3, LEU2, ENO, TPI, alkaline phosphatase promoters (useful for expression in *Saccharomyces*); AOX1 promoter (useful for expression in *Pichia*); β-lactamase, lac, ara, tet, trp, $IP_L$, $IP_R$, T7, tac, and trc promoters (useful for expression in *Escherichia coli*); light regulated-, seed specific-, pollen specific-, ovary specific-, pathogenesis or disease related-, cauliflower mosaic virus 35S, CMV 35S minimal, cassava vein mosaic virus (Cs-VMV), chlorophyll a/b binding protein, ribulose 1,5-bisphosphate carboxylase, shoot-specific, root specific, chitinase, stress inducible, rice tungro bacilliform virus, plant super-promoter, potato leucine aminopeptidase, nitrate reductase, mannopine synthase, nopaline synthase, ubiquitin, zein protein, and anthocyanin promoters (useful for expression in plant cells); animal and mammalian promoters known in the art include, but are not limited to, the SV40 early (SV40e) promoter region, the promoter contained in the 3' long terminal repeat (LTR) of Rous sarcoma virus (RSV), the promoters of the E1A or major late promoter (MLP) genes of adenoviruses (Ad), the cytomegalovirus (CMV) early promoter, the herpes simplex virus (HSV) thymidine kinase (TK) promoter, a baculovirus IE1 promoter, an elongation factor 1 alpha (EF1) promoter, a phosphoglycerate kinase (PGK) promoter, a ubiquitin (Ubc) promoter, an albumin promoter, the regulatory sequences of the mouse metallothionein-L promoter and transcriptional control regions, the ubiquitous promoters (HPRT, vimentin, α-actin, tubulin and the like), the promoters of the intermediate filaments (desmin, neurofilaments, keratin, GFAP, and the like), the promoters of therapeutic genes (of the MDR, CFTR or factor VIII type, and the like), pathogenesis or disease related-promoters, and promoters that exhibit tissue specificity and have been utilized in transgenic animals, such as the elastase I gene control region which is active in pancreatic acinar cells; insulin gene control region active in pancreatic beta cells, immunoglobulin gene control region active in lymphoid cells, mouse mammary tumor virus control region active in testicular, breast, lymphoid and mast cells; albumin gene, Apo AI and Apo AII control regions active in liver, alpha-fetoprotein gene control region active in liver, alpha 1-antitrypsin gene control region active in the liver, β-globin gene control region active in myeloid cells, myelin basic protein gene control region active in oligodendrocyte cells in the brain, myosin light chain-2 gene control region active in skeletal muscle, and gonadotropic releasing hormone gene control region active in the hypothalamus, pyruvate kinase promoter, villin promoter, promoter of the fatty acid binding intestinal protein, promoter of the smooth muscle cell α-actin, and the like. In addition, these expression sequences may be modified by addition of enhancer or regulatory sequences and the like.

Enhancers that may be used in embodiments of the invention include but are not limited to: an SV40 enhancer, a cytomegalovirus (CMV) enhancer, an elongation factor 1 (EF1) enhancer, yeast enhancers, viral gene enhancers, and the like.

Termination control regions, i.e., terminator or polyadenylation sequences, may also be derived from various genes native to the preferred hosts. Optionally, a termination site may be unnecessary, however, it is most preferred if included. In a preferred embodiment of the invention, the termination control region may be comprise or be derived from a synthetic sequence, synthetic polyadenylation signal, an SV40 late polyadenylation signal, an SV40 polyadenylation signal, a bovine growth hormone (BGH) polyadenylation signal, viral terminator sequences, or the like.

The terms "3' non-coding sequences" or "3' untranslated region (UTR)" refer to DNA sequences located downstream (3') of a coding sequence and may comprise polyadenylation [poly(A)] recognition sequences and other sequences encoding regulatory signals capable of affecting mRNA processing or gene expression. The polyadenylation signal is usually characterized by affecting the addition of polyadenylic acid tracts to the 3' end of the mRNA precursor.

"Regulatory region" means a nucleic acid sequence that regulates the expression of a second nucleic acid sequence. A regulatory region may include sequences which are naturally responsible for expressing a particular nucleic acid (a homologous region) or may include sequences of a different origin that are responsible for expressing different proteins or even synthetic proteins (a heterologous region). In particular, the sequences can be sequences of prokaryotic, eukaryotic, or viral genes or derived sequences that stimulate or repress transcription of a gene in a specific or non-specific manner and in an inducible or non-inducible manner. Regulatory regions include origins of replication, RNA splice sites, promoters, enhancers, transcriptional termination sequences, and signal sequences which direct the polypeptide into the secretory pathways of the target cell.

A regulatory region from a "heterologous source" is a regulatory region that is not naturally associated with the expressed nucleic acid. Included among the heterologous regulatory regions are regulatory regions from a different species, regulatory regions from a different gene, hybrid regulatory sequences, and regulatory sequences which do not occur in nature, but are designed by one having ordinary skill in the art.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene. The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated yet has an effect on cellular processes.

A "polypeptide" is a polymeric compound comprised of covalently linked amino acid residues. Amino acids have the following general structure:

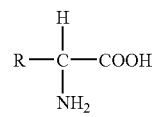

Amino acids are classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group. A polypeptide of the invention preferably comprises at least about 14 amino acids.

A "protein" is a polypeptide that performs a structural or functional role in a living cell.

An "isolated polypeptide" or "isolated protein" is a polypeptide or protein that is substantially free of those compounds that are normally associated therewith in its natural state (e.g., other proteins or polypeptides, nucleic acids, carbohydrates, lipids). "Isolated" is not meant to exclude artificial or synthetic mixtures with other compounds, or the presence of impurities which do not interfere with biological activity, and which may be present, for example, due to incomplete purification, addition of stabilizers, or compounding into a pharmaceutically acceptable preparation.

A "variant" of a polypeptide or protein is any analogue, fragment, derivative, or mutant which is derived from a polypeptide or protein and which retains at least one biological property of the polypeptide or protein. Different variants of the polypeptide or protein may exist in nature. These variants may be allelic variations characterized by differences in the nucleotide sequences of the structural gene coding for the protein, or may involve differential splicing or post-translational modification. The skilled artisan can produce variants having single or multiple amino acid substitutions, deletions, additions, or replacements. These variants may include, inter alia: (a) variants in which one or more amino acid residues are substituted with conservative or non-conservative amino acids, (b) variants in which one or more amino acids are added to the polypeptide or protein, (c) variants in which one or more of the amino acids includes a substituent group, and (d) variants in which the polypeptide or protein is fused with another polypeptide such as serum albumin. The techniques for obtaining these variants, including genetic (suppressions, deletions, mutations, etc.), chemical, and enzymatic techniques, are known to persons having ordinary skill in the art.

A "heterologous protein" refers to a protein not naturally produced in the cell.

A "mature protein" refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

The term "signal peptide" refers to an amino terminal polypeptide preceding the secreted mature protein. The signal peptide is cleaved from and is therefore not present in the mature protein. Signal peptides have the function of directing and translocating secreted proteins across cell membranes. Signal peptide is also referred to as signal protein.

A "signal sequence" is included at the beginning of the coding sequence of a protein to be expressed on the surface of a cell. This sequence encodes a signal peptide, N-terminal to the mature polypeptide that directs the host cell to translocate the polypeptide. The term "translocation signal sequence" is used herein to refer to this sort of signal sequence. Translocation signal sequences can be found associated with a variety of proteins native to eukaryotes and prokaryotes, and are often functional in both types of organisms.

The term "homology" refers to the percent of identity between two polynucleotide or two polypeptide moieties. The correspondence between the sequence from one moiety to another can be determined by techniques known to the art. For example, homology can be determined by a direct comparison of the sequence information between two polypeptide molecules by aligning the sequence information and using readily available computer programs. Alternatively, homology can be determined by hybridization of polynucleotides under conditions that form stable duplexes between homologous regions, followed by digestion with single-stranded-specific nuclease(s) and size determination of the digested fragments.

As used herein, the term "homologous" in all its grammatical forms and spelling variations refers to the relationship between proteins that possess a "common evolutionary origin," including proteins from superfamilies (e.g., the immunoglobulin superfamily) and homologous proteins from different species (e.g., myosin light chain, etc.) (Reeck et al., 1987, Cell 50: 667.). Such proteins (and their encoding genes) have sequence homology, as reflected by their high degree of sequence similarity. However, in common usage and in the instant application, the term "homologous," when modified with an adverb such as "highly," may refer to sequence similarity and not a common evolutionary origin.

Accordingly, the term "sequence similarity" in all its grammatical forms refers to the degree of identity or correspondence between nucleic acid or amino acid sequences of proteins that may or may not share a common evolutionary origin (see Reeck et al., 1987, Cell 50:667).

In a specific embodiment, two DNA sequences are "substantially homologous" or "substantially similar" when at least about 50% (preferably at least about 75%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Sambrook et al., 1989, supra.

As used herein, "substantially similar" refers to nucleic acid fragments wherein changes in one or more nucleotide bases results in substitution of one or more amino acids, but do not affect the functional properties of the protein encoded by the DNA sequence. "Substantially similar" also refers to nucleic acid fragments wherein changes in one or more nucleotide bases does not affect the ability of the nucleic acid fragment to mediate alteration of gene expression by antisense or co-suppression technology. "Substantially similar" also refers to modifications of the nucleic acid fragments of the instant invention such as deletion or insertion of one or more nucleotide bases that do not substantially affect the functional properties of the resulting transcript. It is therefore understood that the invention encompasses more than the specific exemplary sequences. Each of the proposed modifications is well within the routine skill in the art, as is determination of retention of biological activity of the encoded products.

Moreover, the skilled artisan recognizes that substantially similar sequences encompassed by this invention are also defined by their ability to hybridize, under stringent conditions (0.1×SSC, 0.1% SDS, 65° C. and washed with 2×SSC, 0.1% SDS followed by 0.1×SSC, 0.1% SDS), with the sequences exemplified herein. Substantially similar nucleic acid fragments of the instant invention are those nucleic acid fragments whose DNA sequences are at least 70% identical to the DNA sequence of the nucleic acid fragments reported herein. Preferred substantially nucleic acid fragments of the instant invention are those nucleic acid fragments whose DNA sequences are at least 80% identical to the DNA sequence of the nucleic acid fragments reported herein. More preferred nucleic acid fragments are at least 90% identical to the DNA sequence of the nucleic acid fragments reported herein. Even more preferred are nucleic acid fragments that are at least 95% identical to the DNA sequence of the nucleic acid fragments reported herein.

Two amino acid sequences are "substantially homologous" or "substantially similar" when greater than about 40% of the amino acids are identical, or greater than 60% are similar (functionally identical). Preferably, the similar or homologous sequences are identified by alignment using, for example, the GCG (Genetics Computer Group, Program Manual for the GCG Package, Version 7, Madison, Wis.) pileup program.

The term "corresponding to" is used herein to refer to similar or homologous sequences, whether the exact position is identical or different from the molecule to which the similarity or homology is measured. A nucleic acid or amino acid sequence alignment may include spaces. Thus, the term "corresponding to" refers to the sequence similarity, and not the numbering of the amino acid residues or nucleotide bases.

A "substantial portion" of an amino acid or nucleotide sequence comprises enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., (1993) *J. Mol. Biol.* 215: 403-410; see also www.ncbi.nlm.nih.gov/BLAST/). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignments of the sequences may be performed using the Clustal method of alignment (Higgins and Sharp (1989) *CABIOS*. 5:151-153) with the default parameters (GAP PENALTY=10, GAP LENGTH PENALTY=10). Default parameters for pairwise alignments using the Clustal method may be selected: KTUPLE 1, GAP PENALTY=3, WINDOW=5 and DIAGONALS SAVED=5.

The term "sequence analysis software" refers to any computer algorithm or software program that is useful for the analysis of nucleotide or amino acid sequences. "Sequence analysis software" may be commercially available or independently developed. Typical sequence analysis software will include but is not limited to the GCG suite of programs (Wisconsin Package Version 9.0, Genetics Computer Group (GCG), Madison, Wis.), BLASTP, BLASTN, BLASTX (Altschul et al., *J. Mol. Biol.* 215: 403-410 (1990), and DNASTAR (DNASTAR, Inc. 1228 S. Park St. Madison, Wis. 53715 USA). Within the context of this application it will be understood that where sequence analysis software is used for analysis, that the results of the analysis will be based on the "default values" of the program referenced, unless otherwise specified. As used herein "default values" will mean any set of values or parameters, which originally load with the software when first initialized.

"Synthetic genes" can be assembled from oligonucleotide building blocks that are chemically synthesized using procedures known to those skilled in the art. These building blocks are ligated and annealed to form gene segments that are then enzymatically assembled to construct the entire gene. "Chemically synthesized", as related to a sequence of DNA, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

The Invention

The present invention provides compositions and methods for obtaining site-specific recombination in eukaryotic cells. More specifically, the invention employs prokaryotic recombinases, such as bacteriophage recombinases, that are unidirectional in that they can catalyze recombination between two complementary recombination sites, but cannot catalyze recombination between the hybrid sites that are formed by this recombination. The inventor has identified novel recombinases that each directs recombination only between a bacterial attachment site (attB) and a phage attachment site (attP). The recombinase cannot mediate recombination between the attL and attR hybrid sites that are formed upon recombination between attB and attP. Because recombinases such as these cannot alone catalyze the reverse reaction, the attB and attP recombination is stable. This property is one that sets the compositions and methods of the present invention apart from other recombination systems currently used for eukaryotic cells, such as the Cre-10x or FLP-FRT system, where the recombination reactions are reversible. Use of the recombination systems of the present invention provides new opportunities for directing stable transgene and chromosome rearrangements in eukaryotic cells.

The methods of the present invention involve contacting a pair of recombination attachment sites, attB and attP, that are present in a eukaryotic cell with a corresponding recombinase. The recombinase then mediates recombination between the recombination attachment sites. Depending upon the relative locations of the recombination attachment sites, any one of a number of events can occur as a result of the recombination. For example, if the recombination attachment sites are present on different nucleic acid molecules, the recombination can result in integration of one nucleic acid molecule into a second molecule. Thus, one can obtain integration of a plasmid that contains one recombination site into a eukaryotic cell chromosome that includes the corresponding recombination site. Because the recombinases used in the methods of the invention cannot catalyze the reverse reaction, the integration is stable. Such methods are useful, for example, for obtaining stable integration into the eukaryotic chromosome of a transgene that is present on the plasmid.

The recombination attachment sites can also be present on the same nucleic acid molecule. In such cases, the resulting product typically depends upon the relative orientation of the attachment sites. For example, recombination between sites that are in the parallel or direct orientation will generally result in excision of any DNA that lies between the recombination attachment sites. In contrast, recombination between attachment sites that are in the reverse orientation can result in inversion of the intervening DNA. Likewise, the resulting rearranged nucleic acid is stable in that the recombination is irreversible in the absence of an additional factor or factors, generally encoded by the particular bacteriophage and/or by the host cell of the bacteriophage from which the recombinase is derived, that is not normally found in eukaryotic cells. One example of an application for which this method is useful involves the placement of a promoter between the recombination attachment sites. If the promoter is initially in the opposite orientation relative to a coding sequence that is to be expressed by the promoter and the recombination sites that flank the promoter are in the inverted orientation, contacting the recombination attachment sites will result in inversion of the promoter, thus placing the promoter in the correct orientation to drive expression of the coding sequence. Similarly, if the promoter is initially in the correct orientation for expression and the recombination attachment sites are in the same orientation, contacting the recombination attachment sites with the recombinase can result in excision of the promoter fragment, thus stopping expression of the coding sequence.

The methods of the invention are also useful for obtaining translocations of chromosomes. For example, in these embodiments, one recombination attachment site is placed on one chromosome and a second recombination attachment site that can serve as a substrate for recombination with the first recombination attachment site is placed on a second chromosome. Upon contacting the recombination attachment sites with a recombinase, recombination occurs that results in swapping of the two chromosome arms. For example, one can construct two strains of an organism, one strain of which includes the first recombination attachment site and the second strain that contains the second recombination attachment site. The two strains are then crossed, to obtain a progeny strain that includes both of the recombination attachment sites. Upon contacting the attachment sites with the recombinase, chromosome arm swapping occurs.

Recombinases

The recombinases used in the practice of the present invention can be introduced into a target cell before, concurrently with, or after the introduction of a targeting vector. The recombinase can be directly introduced into a cell as a protein, for example, using liposomes, coated particles, or microinjection. Alternately, a polynucleotide, either DNA or messenger RNA, encoding the recombinase can be introduced into the cell using a suitable expression vector. The targeting vector components described above are useful in the construction of expression cassettes containing sequences encoding a recombinase of interest. However, expression of the recombinase can be regulated in other ways, for example, by placing the expression of the recombinase under the control of a regulatable promoter (i.e., a promoter whose expression can be selectively induced or repressed).

Recombinases for use in the practice of the present invention can be produced recombinantly or purified as previously described. Polypeptides having the desired recombinase activity can be purified to a desired degree of purity by methods known in the art of protein ammonium sulfate precipitation, purification, including, but not limited to, size fractionation, affinity chromatography, HPLC, ion exchange chromatography, heparin agarose affinity chromatography (e.g., Thorpe & Smith, Proc. Nat. Acad. Sci. 95:5505-5510, 1998.)

Recombinase polypeptides, and nucleic acids that encode the recombinase polypeptides of the present invention, are described in Example 1, and can be obtained using routine methods known to those of skill in the art. In preferred embodiments the recombinase is an isolated polynucleotide sequence comprising a nucleic acid that is at least 90% identical to the nucleic acid sequence selected from the group consisting of SEQ ID NO: 1, SEQ ID NO: 3, SEQ ID NO: 5, SEQ ID NO: 7, and SEQ ID NO: 9, wherein the nucleic acid has recombinase activity. More preferably the recombinase is an isolated polynucleotide sequence comprising the nucleic acid sequence selected from the group consisting of SEQ ID NO: 1, SEQ ID NO: 3, SEQ ID NO: 5, SEQ ID NO: 7, and SEQ ID NO: 9. Even more preferably the recombinase is an isolated polynucleotide sequence comprising a nucleic acid sequence that encodes a recombinase selecting from the group consisting of a SPβc2 recombinase, a SF370.1 recombinase, a Bxb1 recombinase, an A118 recombinase and a φRv1 recombinase.

The recombinases can be introduced into the eukaryotic cells that contain the recombination attachment sites at which recombination is desired by any suitable method. Methods of introducing functional proteins, e.g., by microinjection or other methods, into cells are well known in the art. Introduction of purified recombinase protein ensures a transient presence of the protein and its function, which is often a preferred embodiment. Alternatively, a gene encoding the recombinase can be included in an expression vector used to transform the cell, in which the recombinase-encoding polynucleotide is operably linked to a promoter which mediates expression of the polynucleotide in the eukaryotic cell. The recombinase polypeptide can also be introduced into the eukaryotic cell by messenger RNA that encodes the recombinase polypeptide. It is generally preferred that the recombinase be present for only such time as is necessary for insertion of the nucleic acid fragments into the genome being modified. Thus, the lack of permanence associated with most expression vectors is not expected to be detrimental. One can introduce the recombinase gene into the cell before, after, or simultaneously with, the introduction of the exogenous polynucleotide of interest. In one embodiment, the recombinase gene is present within the vector that carries the polynucleotide that is to be inserted; the recombinase gene can even be included within the polynucleotide. In other embodiments, the recombinase gene is introduced into a transgenic eukaryotic organism, e.g., a transgenic plant, animal, fungus, or the like, which is then crossed with an organism that contains the corresponding recombination sites. Transgenic cells or animals can be made that express a recombinase constitutively or under cell-specific, tissue-specific, developmental-specific, organelle-specific, or small molecule-inducible or repressible promoters. The recombinases can be also expressed as a fusion protein with other peptides, proteins, nuclear localizing signal peptides, signal peptides, or organelle-specific signal peptides (e.g., mitochondrial or chloroplast transit peptides to facilitate recombination in mitochondria or chloroplast).

In embodiments of the present invention, recombination attachment sites comprise an isolated polynucleotide sequence comprising a nucleic acid that is at least 90% identical to the nucleic acid sequence selected from the group consisting of SEQ ID NO: 11, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, and SEQ ID NO: 21. Preferably the attachment site is an isolated polynucleotide sequence comprising the nucleic acid sequence selected from the group consisting of SEQ ID NO: 11, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, and SEQ ID NO: 21.

Vectors/Constructs

The targeting constructs contemplated by the invention may contain additional nucleic acid fragments such as control sequences, marker sequences, selection sequences and the like as discussed below.

The present invention also provides means for targeted insertion of a polynucleotide (or nucleic acid sequence(s)) of interest into a genome by, for example, (i) providing a recombinase, wherein the recombinase is capable of facilitating recombination between a first recombination site and a second recombination site, (ii) providing a targeting construct having a first recombination sequence and a polynucleotide of interest, (iii) introducing the recombinase and the targeting construct into a cell which contains in its nucleic acid the second recombination site, wherein said introducing is done under conditions that allow the recombinase to facilitate a recombination event between the first and second recombination sites.

The present invention also relates to a vector for site-specific integration of a polynucleotide sequence into the genome of an isolated eukaryotic cell, said vector comprising a polynucleotide of interest, and a second recombination attB or attP site, wherein said second recombination attB or attP site comprises a polynucleotide sequence that recombines with a first recombination attP or attB site or pseudo attP or pseudo attB site in the genome of said isolated eukaryotic cell and said recombination occurs in the presence of a site-specific recombinase selected from the group consisting of a *Listeria monocytogenes* phage recombinase, a *Streptococcus pyogenes* phage recombinase, a *Bacillus subtilis* phage recombinase, a *Mycobacterium tuberculosis* phage recombinase and a *Mycobacterium smegmatis* phage recombinase, provided that when the first recombination site is attB or pseudo attB, the second recombination site is attP and when the first recombination site is attP or pseudo attP, the second recombination site is attB. Preferably the recombinase is selected from the group consisting of an A118 recombinase, a SF370.1 recombinase, a SPβc2 recombinase, a φRv1 recombinase, and a Bxb1 recombinase.

Polynucleotides of interest can include, but are not limited to, expression cassettes encoding polypeptide products. The targeting constructs can be circular or linear and may also contain selectable markers, an origin of replication, and other elements.

A variety of expression vectors are suitable for use in the practice of the present invention, both for prokaryotic expression and eukaryotic expression. In general, the targeting construct will have one or more of the following features: a promoter, promoter-enhancer sequences, a selection marker sequence, an origin of replication, an inducible element sequence, an epitope—tag sequence, and the like.

Promoter and promoter-enhancer sequences are DNA sequences to which RNA polymerase binds and initiates transcription. The promoter determines the polarity of the transcript by specifying which strand will be transcribed. Bacterial promoters consist of consensus sequences, −35 and −10 nucleotides relative to the transcriptional start, which are bound by a specific sigma factor and RNA polymerase. Eukaryotic promoters are more complex. Most promoters utilized in expression vectors are transcribed by RNA polymerase II. General transcription factors (GTFS) first bind specific sequences near the start and then recruit the binding of RNA polymerase II. In addition to these minimal promoter elements, small sequence elements are recognized specifically by modular DNA-binding/trans-activating proteins (e.g. AP-1, SP-1) that regulate the activity of a given promoter. Viral promoters serve the same function as bacterial or eukaryotic promoters and either provide a specific RNA polymerase in trans (bacteriophage T7) or recruit cellular factors and RNA polymerase (SV40, RSV, CMV). Viral promoters may be preferred as they are generally particularly strong promoters.

Promoters may be, furthermore, either constitutive or regulatable (i.e., inducible or repressible). Inducible elements are DNA sequence elements which act in conjunction with promoters and bind either repressors (e.g. lacO/LAC Iq repressor system in *E. coli*) or inducers (e.g. gall/GAL4 inducer system in yeast). In either case, transcription is virtually "shut off" until the promoter is repressed or induced, at which point transcription is "turned-on."

Examples of constitutive promoters include the int promoter of bacteriophage λ, the bla promoter of the β-lactamase gene sequence of pBR322, the CAT promoter of the chloramphenicol acetyl transferase gene sequence of pPR325, and the like. Examples of inducible prokaryotic promoters include the major right and left promoters of bacteriophage (P.sub.L and P.sub.R), the trp, reca, lacZ, AraC and gal promoters of *E. coli*, the α-amylase (Ulmanen Ett at., J. Bacteriol. 162:176-182, 1985) and the sigma-28-specific promoters of *B. subtilis* (Gilman et al., Gene sequence 32:11-20(1984)), the promoters of the bacteriophages of *Bacillus* (Gryczan, In: The Molecular Biology of the Bacilli, Academic Press, Inc., NY (1982)), *Streptomyces* promoters (Ward et at., Mol. Gen. Genet. 203:468-478, 1986), and the like. Exemplary prokaryotic promoters are reviewed by Glick (J. Ind. Microtiot. 1:277-282, 1987); Cenatiempo (Biochimie 68: 505-516, 1986); and Gottesman (Ann. Rev. Genet. 18:415-442, 1984).

Preferred eukaryotic promoters include, but are not limited to, the following: the promoter of the mouse metallothionein I gene sequence (Hamer et al., J. Mol. Appl. Gen. 1:273-288, 1982); the TK promoter of Herpes virus (McKnight, Cell 31:355-365, 1982); the SV40 early promoter (Benoist et al., Nature (London) 290:304-310, 1981); the yeast gall gene sequence promoter (Johnston et al., Proc. Natl. Acad. Sci. (USA) 79:6971-6975, 1982); Silver et al., Proc. Natl. Acad. Sci. (USA) 81:5951-59SS, 1984), the CMV promoter, the EF-1 promoter, ecdysone-responsive promoter(s), tetracycline-responsive promoter, and the like. Exemplary promoters for use in the present invention are selected such that they are functional in cell type (and/or animal or plant) into which they are being introduced.

Selection markers are valuable elements in expression vectors as they provide a means to select for growth of only those cells that contain a vector. Such markers are of two types: drug resistance and auxotrophic. A drug resistance marker enables cells to detoxify an exogenously added drug that would otherwise kill the cell. Auxotrophic markers allow cells to synthesize an essential component (usually an amino acid) while grown in media that lacks that essential component.

Common selectable marker genes include those for resistance to antibiotics such as ampicillin, tetracycline, kanamycin, bleomycin, streptomycin, hygromycin, neomycin, Zeocin.™., and the like. Selectable auxotrophic genes include, for example, hisD, that allows growth in histidine free media in the presence of histidinol.

A further element useful in an expression vector is an origin of replication. Replication origins are unique DNA segments that contain multiple short repeated sequences that are recognized by multimeric origin-binding proteins and that play a key role in assembling DNA replication enzymes at the origin site. Suitable origins of replication for use in expression vectors employed herein include $E.$ $coli$ oriC, colE1 plasmid origin, $2\mu$ and ARS (both useful in yeast systems), sf1, SV40, EBV oriP (useful in mammalian systems), and the like.

Epitope tags are short peptide sequences that are recognized by epitope specific antibodies. A fusion protein comprising a recombinant protein and an epitope tag can be simply and easily purified using an antibody bound to a chromatography resin. The presence of the epitope tag furthermore allows the recombinant protein to be detected in subsequent assays, such as Western blots, without having to produce an antibody specific for the recombinant protein itself. Examples of commonly used epitope tags include V5, glutathione-S-transferase (GST), hemaglutinin (HA), the peptide Phe-His-His-Thr-Thr, chitin binding domain, and the like.

A further useful element in an expression vector is a multiple cloning site or polylinker. Synthetic DNA encoding a series of restriction endonuclease recognition sites is inserted into a plasmid vector, for example, downstream of the promoter element. These sites are engineered for convenient cloning of DNA into the vector at a specific position.

The foregoing elements can be combined to produce expression vectors suitable for use in the methods of the invention. Those of skill in the art would be able to select and combine the elements suitable for use in their particular system in view of the teachings of the present specification. Suitable prokaryotic vectors include plasmids such as those capable of replication in $E.$ $coli$ (for example, pBR322, ColE1, pSC101, PACYC 184, itVX, PRSET, pBAD (Invitrogen, Carlsbad, Calif.) and the like). Such plasmids are disclosed by Sambrook (cf. "Molecular Cloning: A Laboratory Manual," second edition, edited by Sambrook, Fritsch, & Maniatis, Cold Spring Harbor Laboratory, (1989)). *Bacillus* plasmids include pC194, pC221, pT127, and the like, and are disclosed by Gryczan (In: The Molecular Biology of the Bacilli, Academic Press, NY (1982), pp. 307-329). Suitable *Streptomyces* plasmids include pli101 (Kendall et al., J. Bacteriol. 169:4177-4183, 1987), and *Streptomyces* bacteriophages such as φC31 (Chater et al., In: Sixth International Symposium on Actinomycetales Biology, Akademiai Kaido, Budapest, Hungary (1986), pp. 45-54). *Pseudomonas* plasmids are reviewed by John et al. (Rev. Infect. Dis. 8:693-704, 1986), and Izaki (Jpn. J. Bacteriol. 33:729-742, 1978).

Suitable eukaryotic plasmids include, for example, BPV, EBV, vaccinia, SV40, 2-micron circle, pcDNA3.1, pcDNA3.1/GS, pDual, pYES2/GS, pMT, p IND, pIND(Spl), pVgRXR (Invitrogen), and the like, or their derivatives. Such plasmids are well known in the art (Botstein et al., Miami Wntr. SyTnp. 19:265-274, 1982; Broach, In: "The Molecular Biology of the Yeast *Saccharomyces*: Life Cycle and Inheritance", Cold Spring Harbor Laboratory, Cold Spring Harbor, N.Y., p. 445-470, 1981; Broach, Cell 28:203-204, 1982; Dilon et al., J. Clin. Hematol. Oncol. 10: 39-48, 1980; Maniatis, In: Cell Biology: A Comprehensive Treatise, Vol. 3, Gene Sequence Expression, Academic Press, NY, pp. 563-608, 1980. The targeting cassettes described herein can be constructed utilizing methodologies known in the art of molecular biology (see, for example, Ausubel or Maniatis) in view of the teachings of the specification. As described above, the targeting constructs are assembled by inserting, into a suitable vector backbone, a recombination attachment site, polynucleotides encoding sequences of interest operably linked to a promoter of interest; and, optionally a sequence encoding a positive selection marker.

A preferred method of obtaining polynucleotides, including suitable regulatory sequences (e.g., promoters) is PCR. General procedures for PCR are taught in MacPherson et al., PCR: A PRACTICAL APPROACH, (IRL Press at Oxford University Press, (1991)). PCR conditions for each application reaction may be empirically determined. A number of parameters influence the success of a reaction. Among these parameters are annealing temperature and time, extension time, $Mg^{2+}$ and ATP concentration, pH, and the relative concentration of primers, templates and deoxyribonucleotides. After amplification, the resulting fragments can be detected by agarose gel electrophoresis followed by visualization with ethidium bromide staining and ultraviolet illumination.

The expression cassettes, targeting constructs, vectors, recombinases and recombinase-coding sequences of the present invention can be formulated into kits. Components of such kits can include, but are not limited to, containers, instructions, solutions, buffers, disposables, and hardware.

Methods

The present invention relates to a method for site-specific recombination comprising: providing a first recombination site and a second recombination site; contacting the first and second recombination sites with a prokaryotic recombinase polypeptide, resulting in recombination between the recombination sites, wherein the recombinase polypeptide can mediate recombination between the first and second recombination sites, the first recombination site is attP or attB, the second recombination site is attB or attP, and the recombinase is selected from the group consisting of a *Listeria monocytogenes* phage recombinase, a *Streptococcus pyogenes* phage recombinase, a *Bacillus subtilis* phage recombinase, a *Mycobacterium tuberculosis* phage recombinase and a *Mycobacterium smegmatis* phage recombinase, provided that when the first recombination attachment site is attB, the second recombination attachment site is attP, and when the first recombination attachment site is attP, the second recombination attachment site is attB Further methods of the present invention provide for the introduction of a site-specific recombinase into a cell whose genome is to be modified. A preferred embodiment of the present invention relates to a method for obtaining site-specific recombination in a eukaryotic cell comprises providing a eukaryotic cell that comprises a first recombination attachment site and a second recombination attachment site; contacting the first and second recombination attachment sites with a prokaryotic recombinase polypeptide, resulting in recombination between the recombination attachment sites, wherein the recombinase polypeptide can mediate recombination between the first and second recombination attachment sites, the first recombination attachment site is a phage genomic recombination attachment site (attP) or a bacterial genomic recombination attachment site (attB), the second recombination attachment site is attB or attP, and the recombinase is selected from the group consisting of a *Listeria monocytogenes* phage recombinase, a *Streptococcus pyogenes* phage recombinase, a *Bacillus subtilis* phage recombinase, a *Mycobacterium tuberculosis* phage recombinase and a *Mycobacterium smegmatis* phage recombinase, provided that when the first recombination attachment site is attB, the second recombination attachment site is attP, and when the first recombination attachment site is attP, the second recombination attachment site is attB. In a preferred embodiment the recombinase is selected from the group consisting of an A118 recombinase, a SF370.1 recombinase, a SPβc2 recombinase, a φRv1 recombinase, and a Bxb1 recombinase. In one embodiment the recombination results in integration. Targeted integration of transgenes into predefined genetic loci is a desirable goal for many applications. First, a first recombination site for a site-specific recombinase is inserted at a genomic site, either at a random or at a predetermined location. Subsequently, the cells are transfected with a plasmid carrying the gene or DNA of interest and the second recombination site and a source for recombinase (expression plasmid, RNA, protein, or virus-expressing recombinase). Recombination between the first and second recombination sites leads to integration of plasmid DNA.

In another embodiment the site-specific recombination results in a deletion or excision. The most common application in mammalian genetics is the inactivation or activation at a defined developmental stage. The DNA or gene to be deleted or excised from the chromosomes or episomal DNA is flanked by tandem (direct) repeats of first recombination and second recombination sites. Recombination between the sites due to the introduction of a recombinase leads to deletion of the DNA and gene inactivation. In another type of application, a recombinase can mediate excision of a transcriptional stop signal (present between the promoter and gene) from the genome, thereby linking the promoter element to the open reading frame of a transgene and activating gene expression. The recombinase can be expressed using a constitutive or inducible promoter or by introducing a recombinase-expressing viral vector.

In an additional embodiment, the site-specific recombination results in an inversion. Recombination between first and second recombination sites inserted into the same DNA molecule (intramolecular recombination) in opposite orientations leads to inversion of the intervening DNA segment or fragment.

In a further embodiment, the site-specific recombination results in an exchange of DNA. First a cassette acceptor is created at a location of interest in the chromosome. The cassette acceptor contains DNA of interest, very often a selectable marker gene flanked on either side by first recombination site (for example, attB). Second, an exchange vector containing replacement DNA cassette flanked on either side by the recombination site (for example, attP) is introduced into cells along with the recombinase expression plasmid or recombinase protein. Double cross between the cognate recombination recognition sites leads to the replacement of the DNA between the first recombination sites with that carried by the exchange vector. In another instance, the first recombination site is attP and second recombination site is attB. This procedure is often called recombinase-mediated cassette exchange.

In an additional embodiment, the site-specific recombination results in chromosomal translocations. For chromosomal translocation, a first recombination site is introduced into a first chromosome and second recombination site is introduced into a second chromosome. Supplying the cells with a recombinase leads to translocation of the chromosomes. Translocations are generated when recombination sites are targeted to non-homologous chromosomes. Depending on the relative orientation of recombinase sites, recombination leads to translocation or dicentric and acentric chromosomes. When the recombination sites are oriented in the direction relative to their respective centromeres, translocation occurs. If the recombination sites are in opposite orientation, recombination will result in acentric and dicentric chromosomes.

The present invention also comprises recombinase-mediated DNA insertion at pseudo recombination attachment sites present in the genome. Pseudo recombination or attachment site of the specific recombinase is a native sequence present on the chromosome that the site-specific recombinase can recognize and use for integrating of plasmid DNA containing the first or second recombination sites. The integration at pseudo recombination site is often more frequent than the random integration. This is a one step process in the sense that there is no need to introduce a recombination site into the genome as a first step. Integration at pseudo-sites has applications in gene and cell therapy. Pseudo attB is a native recombination site present in the genome that recombines with attP site. Pseudo attP is a native recombination site present in the genome that recombines with attB site. Accordingly, the present invention provides for a method for obtaining site-specific recombination in a eukaryotic cell, the method comprising: providing a eukaryotic cell that comprises a first recombination site and a second recombination site; contacting the first and second recombination sites with a prokaryotic recombinase polypeptide, resulting in recombination between the recombination sites, wherein the recombinase polypeptide can mediate recombination between the first and second recombination sites, the first recombination site is attP or attB, the second recombination site is a pseudo attachment site, and the recombinase is selected from the group consisting of a *Listeria monocytogenes* phage recombinase, a *Streptococcus pyogenes* phage recombinase, a *Bacillus subtilis* phage recombinase, a *Mycobacterium tuberculosis* phage recombinase and a *Mycobacterium smegmatis* phage recombinase. Preferably the recombinase is selected from the group consisting of an A118 recombinase, a SF370.1 recombinase, a SPβc2 recombinase, a φRv1 recombinase, and a Bxb1 recombinase.

The present invention further comprises methods for obtaining a eukaryotic cell having a stably integrated polynucleotide sequence, the method comprising: introducing a polynucleotide into a eukaryotic cell that comprises a first recombination attB or attP site, wherein the polynucleotide comprises a nucleic acid sequence and a second recombination attP or attB site, and contacting the first and the second recombination sites with a prokaryotic recombinase polypeptide, wherein the recombinase polypeptide can mediate site-specific recombination between the first and second recombination sites, and the recombinase is selected from the group consisting of a *Listeria monocytogenes* phage recombinase, a *Streptococcus pyogenes* phage recombinase, a *Bacillus subtilis* phage recombinase, a *Mycobacterium tuberculosis* phage recombinase and a *Mycobacterium smegmatis* phage recombinase, provided that when the first recombination site is attB, the second recombination site is attP and when the first recombination site is attP, the second recombination site is attB. In another embodiment the method for obtaining a eukaryotic cell having a stably integrated polynucleotide sequence comprises: introducing a polynucleotide into a eukaryotic cell that comprises a first recombination pseudo attachment site, wherein the polynucleotide comprises a nucleic acid sequence and a second recombination attP or attB site, and contacting the first and the second recombination sites with a prokaryotic recombinase polypeptide, wherein the recombinase polypeptide can mediate site-specific recombination between the first and second recombination sites, and the recombinase is selected from the group consisting of a *Listeria monocytogenes* phage recombinase, a *Streptococcus pyogenes* phage recombinase, a *Bacillus subtilis* phage recombinase, a *Mycobacterium tuberculosis* phage recombinase and a *Mycobacterium smegmatis* phage recombinase. In preferred embodiments the recombinase is selected from the group consisting of an A118 recombinase, a SF370.1 recombinase, a SPβc2 recombinase, a φRv1 recombinase, and a Bxb1 recombinase.

The present invention additionally comprises a method for obtaining site-specific recombination in a eukaryotic cell, the method comprising: providing a eukaryotic cell that comprises a first recombination site and a second recombination site with a polynucleotide sequence flanked by a third recombination site and a fourth recombination site; contacting the recombination sites with a prokaryotic recombinase polypeptide, resulting in recombination between the recombination sites, wherein the recombinase polypeptide can mediate recombination between the first and third recombination sites and the second and fourth recombination sites, the first and second recombination sites are attP or attB, the third and fourth recombination sites are attB or attP, and the recombinase is selected from the group consisting of a *Listeria monocytogenes* phage recombinase, a *Streptococcus pyogenes* phage recombinase, a *Bacillus subtilis* phage recombinase, a *Mycobacterium tuberculosis* phage recombinase and a *Mycobacterium smegmatis* phage recombinase, provided that when the first and second recombination attachment sites are attB, the third and fourth recombination attachment sites are attP, and when the first and second recombination attachment sites are attP, the third and fourth recombination attachment sites are attB. Preferably the recombinase is selected from the group consisting of an A118 recombinase, a SF370.1 recombinase, a SPβc2 recombinase, a φRv1 recombinase, and a Bxb1 recombinase.

Another embodiment of the present invention provides for a method for the site-specific integration of a polynucleotide of interest into the genome of a transgenic subject, wherein the genome comprises a first recombination attB or attP site or pseudo attB or pseudo attP site, the method comprising: introducing a nucleic acid that comprises the polynucleotide of interest and a second recombination attP or attB site; contacting the first and the second recombination sites with a prokaryotic recombinase polypeptide, wherein the recombinase polypeptide can mediate site-specific recombination between the first and second recombination sites, and the recombinase is selected from the group consisting of a *Listeria monocytogenes* phage recombinase, a *Streptococcus pyogenes* phage recombinase, a *Bacillus subtilis* phage recombinase, a *Mycobacterium tuberculosis* phage recombinase and a *Mycobacterium smegmatis* phage recombinase, provided that when the first recombination site is attB or pseudo attB, the second recombination site is attP and when the first recombination site is attP or pseudo attP, the second recombination site is attB. Preferably the recombinase is selected from the group consisting of an A118 recombinase, a SF370.1 recombinase, a SPβc2 recombinase, a φRv1 recombinase, and a Bxb1 recombinase.

Another method of the present invention provides for obtaining multiple site-specific recombinations in a eukaryotic cell, the method comprising: providing a eukaryotic cell that comprises a first recombination site and a second recombination site with a third recombination site and a fourth recombination site; contacting the first and second recombination sites with a first prokaryotic recombinase polypeptide, contacting the third and fourth recombination sites with a second prokaryotic recombinase polypeptide, resulting in recombination between the first and second recombination sites and recombination between the third and fourth recombination sites, wherein the first recombinase polypeptide can mediate recombination between the first and second recombination sites and the second recombinase polypeptide can mediate recombination between the third and fourth recombination sites, the first and second recombinase are selected from the group consisting of a *Listeria monocytogenes* phage recombinase, a *Streptococcus pyogenes* phage recombinase, a *Bacillus subtilis* phage recombinase, a *Mycobacterium tuberculosis* phage recombinase and a *Mycobacterium smegmatis* phage recombinase, provided that the first recombinase polypeptide and the second recombinase polypeptide are different. The method can further comprising a fifth recombination site and a sixth recombination site and a third recombinase polypeptide, wherein the third recombinase polypeptide can mediate recombination between the fifth and sixth recombination sites, provided that the third recombinase polypeptide is different than the first and second recombinase polypeptides.

The present invention further relates to a eukaryotic cell that comprises a prokaryotic recombinase polypeptide or a nucleic acid that encodes a prokaryotic recombinase, wherein the recombinase can mediate site-specific recombination between a first recombination site and a second recombination site that can serve as a substrate for recombination with the first recombination site, wherein the first recombination site is attP, pseudo attP, attB or pseudo attB, the second recombination site is attB, pseudo attB, attP or pseudo attP, and the recombinase is selected from the group consisting of a *Listeria monocytogenes* phage recombinase, a *Streptococcus pyogenes* phage recombinase, a *Bacillus subtilis* phage recombinase, a *Mycobacterium tuberculosis* phage recombinase and a *Mycobacterium smegmatis* phage recombinase, provided that when the first recombination site is attB, the second recombination site is attP or pseudo attP, when the first recombination site is pseudo attB, the second recombination site is attP, when the first recombination site is attP, the second recombination site is attB or pseudo attB, and when the first recombination site is pseudo attP, the second recombination site is attB. Preferably the recombinase is selected from the group consisting of an A118 recombinase, a SF370.1 recombinase, a SPβc2 recombinase, a φRv1 recombinase, and a Bxb1 recombinase.

Cells

Cells suitable for modification employing the methods of the invention include both prokaryotic cells and eukaryotic cells. Prokaryotic cells are cells that lack a defined nucleus. Examples of suitable prokaryotic cells include bacterial cells, mycoplasmal cells and archaebacterial cells. Particularly preferred prokaryotic cells include those that are useful either in various types of test systems (discussed in greater detail below) or those that have some industrial utility such as *Klebsiella oxytoca* (ethanol production), *Clostridium acetobutylicum* (butanol production), and the like (see Green and Bennet, Biotech & Bioengineering 58:215-221, 1998; Ingram, et al, Biotech & Bioengineering 58:204-206, 1998). Suitable eukaryotic cells include both animal cells (such as from insect, rodent, cow, goat, rabbit, sheep, non-human primate, human, and the like) and plant cells (such as rice, corn, cotton, tobacco, tomato, potato, and the like). Cell types applicable to particular purposes are discussed in greater detail below.

Yet another embodiment of the invention comprises isolated genetically engineered cells. Suitable cells may be prokaryotic or eukaryotic, as discussed above. The genetically engineered cells of the invention may be unicellular organisms or may be derived from multicellular organisms. By "isolated" in reference to genetically engineered cells derived from multicellular organisms it is meant the cells are outside a living body, whether plant or animal, and in an artificial environment. The use of the term isolated does not imply that the genetically engineered cells are the only cells present.

In one embodiment, the genetically engineered cells of the invention contain any one of the nucleic acid constructs of the invention. In a second embodiment, a recombinase that specifically recognizes recombination sequences is introduced into genetically engineered cells containing one of the nucleic acid constructs of the invention under conditions such that the nucleic acid sequence(s) of interest will be inserted into the genome. Thus, the genetically engineered cells possess a modified genome. Methods of introducing such a recombinase are well known in the art and are discussed above.

The genetically engineered cells of the invention can be employed in a variety of ways. Unicellular organisms can be modified to produce commercially valuable substances such as recombinant proteins, industrial solvents, industrially useful enzymes, and the like. Preferred unicellular organisms include fungi such as yeast (for example, *S. pombe, Pichia pastoris, S. cerevisiae* (such as INVSc1), and the like) *Aspergillis*, and the like, and bacteria such as *Klebsiella, Streptomyces*, and the like.

Isolated cells from multicellular organisms can be similarly useful, including insect cells, mammalian cells and plant cells. Mammalian cells that may be useful include those derived from rodents, primates and the like. They include Chinese Hamster Ovary (CHO) cells, HeLa cells, mouse neural stem cells, rat bone marrow stromal cells, cells of fibroblast origin such as VERO, 3T3 or CHOK1, HEK 293 cells or cells of lymphoid origin (such as 32D cells) and their derivatives.

In addition, plant cells, such as tobacco BY2 cells, are also available as hosts, and control sequences compatible with plant cells are available, such as the cauliflower mosaic virus 35S and 19S, nopaline synthase promoter and polyadenylation signal sequences, and the like. Appropriate transgenic plant cells can be used to produce transgenic plants.

Another preferred host is an insect cell, for example from the *Drosophila* larvae. Using insect cells as hosts, the *Drosophila* alcohol dehydrogenase promoter can be used (Rubin, Science 240:1453-1459, 1988). Alternatively, baculovirus vectors can be engineered to express large amounts of peptide encoded by a desired nucleic acid sequence in insect cells (Jasny, Science 238:1653, 1987); Miller et al., In: Genetic Engineering (1986), Setlow, J. K., et al., eds., Plenum, Vol. 8, pp. 277-297).

The genetically engineered cells of the invention are additionally useful as tools to screen for substances capable of modulating the activity of a protein encoded by a nucleic acid fragment of interest. Thus, an additional embodiment of the invention comprises methods of screening comprising contacting genetically engineered cells of the invention with a test substance and monitoring the cells for a change in cell phenotype, cell proliferation, cell differentiation, enzymatic activity of the protein or the interaction between the protein and a natural binding partner of the protein when compared to test cells not contacted with the test substance.

A variety of test substances can be evaluated using the genetically engineered cells of the invention including peptides, proteins, antibodies, low molecular weight organic compounds, natural products derived from, for example, fungal or plant cells, and the like. By "low molecular weight organic compound" it is, meant a chemical species with a molecular weight of generally less than 500-1000. Sources of test substances are well known to those of skill in the art.

Various assay methods employing cells are also well known by those skilled in the art. They include, for example, assays for enzymatic activity (Hirth, et al, U.S. Pat. No. 5,763, 198, issued Jun. 9, 1998), assays for binding of a test substance to a protein expressed by the genetically engineered cells, assays for transcriptional activation of a reporter gene, and the like.

Cells modified by the methods of the present invention can be maintained under conditions that, for example, (i) keep them alive but do not promote growth, (ii) promote growth of the cells, and/or (iii) cause the cells to differentiate or dedifferentiate. Cell culture conditions are typically permissive for the action of the recombinase in the cells, although regulation of the activity of the recombinase may also be modulated by culture conditions (e.g., raising or lowering the temperature at which the cells are cultured). For a given cell, cell-type, tissue, or organism, culture conditions are known in the art.

Transgenic Plants and Non-Human Animals

In another embodiment, the present invention comprises transgenic plants and nonhuman transgenic animals whose genomes have been modified by employing the methods and compositions of the invention. Transgenic animals may be produced employing the methods of the present invention to serve as a model system for the study of various disorders and for screening of drugs that modulate such disorders.

A "transgenic" plant or animal refers to a genetically engineered plant or animal, or offspring of genetically engineered plants or animals. A transgenic plant or animal usually contains material from at least one unrelated organism, such as, from a virus. The term "animal" as used in the context of transgenic organisms means all species except human. It also includes an individual animal in all stages of development, including embryonic and fetal stages. Farm animals (e.g., chickens, pigs, goats, sheep, cows, horses, rabbits and the like), rodents (such as mice), and domestic pets (e.g., cats and dogs) are included within the scope of the present invention. In a preferred embodiment, the animal is a mouse or a rat.

The term "chimeric" plant or animal is used to refer to plants or animals in which the heterologous gene is found, or in which the heterologous gene is expressed in some but not all cells of the plant or animal.

The term transgenic animal also includes a germ cell line transgenic animal. A "germ cell line transgenic animal" is a transgenic animal in which the genetic information provided by the invention method has been taken up and incorporated into a germ line cell, therefore conferring the ability to transfer the information to offspring. If such offspring, in fact, possess some or all of that information, then they, too, are transgenic animals.

Methods of generating transgenic plants and animals are known in the art and can be used in combination with the teachings of the present application.

In one embodiment, a transgenic animal of the present invention is produced by introducing into a single cell embryo a nucleic acid construct, comprising a first recombination site capable of recombining with a second recombination site found within the genome of the organism from which the cell was derived and a nucleic acid fragment of interest, in a manner such that the nucleic acid fragment of interest is stably integrated into the DNA of germ line cells of the mature animal and is inherited in normal Mendelian fashion. In this embodiment, the nucleic acid fragment of interest can be any one of the fragment described previously. Alternatively, the nucleic acid sequence of interest can encode an exogenous product that disrupts or interferes with expression of an endogenously produced protein of interest, yielding a transgenic animal with decreased expression of the protein of interest.

A variety of methods are available for the production of transgenic animals. A nucleic acid construct of the invention can be injected into the pronucleus, or cytoplasm, of a fertilized egg before fusion of the male and female pronuclei, or injected into the nucleus of an embryonic cell (e.g., the nucleus of a two-cell embryo) following the initiation of cell division (Brinster, et al., Proc. Nat. Acad. Sci. USA 82: 4438, 1985). Embryos can be infected with viruses, especially retroviruses, modified with an attD recombination site and a nucleic acid sequence of interest. The cell can further be treated with a site-specific recombinase as described above to promote integration of the nucleic acid sequence of interest into the genome.

By way of example only, to prepare a transgenic mouse, female mice are induced to superovulate. After being allowed to mate, the females are sacrificed by $CO_2$ asphyxiation or cervical dislocation and embryos are recovered from excised oviducts. Surrounding cumulus cells are removed. Pronuclear embryos are then washed and stored until the time of injection. Randomly cycling adult female mice are paired with vasectomized males. Recipient females are mated at the same time as donor females. Embryos then are transferred surgically. The procedure for generating transgenic rats is similar to that of mice. See Hammer, et al., Cell 63:1099-1112, 1990). Rodents suitable for transgenic experiments can be obtained from standard commercial sources such as Charles River (Wilmington, Mass.), Taconic (Germantown, N.Y.), Harlan Sprague Dawley (Indianapolis, Ind.), etc.

The procedures for manipulation of the rodent embryo and for microinjection of DNA into the pronucleus of the zygote are well known to those of ordinary skill in the art (Hogan, et al., supra). Microinjection procedures for fish, amphibian eggs and birds are detailed in Houdebine and Chourrout, Experientia 47:897-905, 1991). Other procedures for introduction of DNA into tissues of animals are described in U.S. Pat. No. 4,945,050 (Sandford et al., Jul. 30, 1990).

Totipotent or pluripotent stem cells derived from the inner cell mass of the embryo and stabilized in culture can be manipulated in culture to incorporate nucleic acid sequences employing invention methods. A transgenic animal can be produced from such cells through injection into a blastocyst that is then implanted into a foster mother and allowed to come to term.

Methods for the culturing of stem cells and the subsequent production of transgenic animals by the introduction of DNA into stem cells using methods such as electroporation, calcium phosphate/DNA precipitation, microinjection, liposome fusion, retroviral infection, and the like are also are well known to those of ordinary skill in the art. See, for example, Teratocarcinomas and Embryonic Stem Cells, A Practical Approach, E. J. Robertson, ed., IRL Press, 1987). Reviews of standard laboratory procedures for microinjection of heterologous DNAs into mammalian (mouse, pig, rabbit, sheep, goat, cow) fertilized ova include: Hogan et al., Manipulating the Mouse Embryo (Cold Spring Harbor Press 1986); Krimpenfort et al., 1991, Bio/Technology 9:86; Palmiter et al., 1985, Cell 41:343; Kraemer et al., Genetic Manipulation of the Early Mammalian Embryo (Cold Spring Harbor Laboratory Press 1985); Hammer et al., 1985, Nature, 315:680; Purcel et al., 1986, Science, 244:1281; Wagner et al., U.S. Pat. No. 5,175,385; Krimpenfort et al., U.S. Pat. No. 5,175,384, the respective contents of which are incorporated by reference.

The final phase of the procedure is to inject targeted ES cells into blastocysts and to transfer the blastocysts into pseudo-pregnant females. The resulting chimeric animals are bred and the offspring are analyzed by Southern blotting to identify individuals that carry the transgene. Procedures for the production of non-rodent mammals and other animals have been discussed by others (see Houdebine and Chourrout, supra; Pursel, et al., Science 244:1281-1288, 1989; and Simms, et al., Bio/Technology 6:179-183, 1988). Animals carrying the transgene can be identified by methods well known in the art, e.g., by dot blotting or Southern blotting.

The term transgenic as used herein additionally includes any organism whose genome has been altered by in vitro manipulation of the early embryo or fertilized egg or by any transgenic technology to induce a specific gene knockout. The term "gene knockout" as used herein, refers to the targeted disruption of a gene in vivo with loss of function that has been achieved by use of the invention vector. In one embodiment, transgenic animals having gene knockouts are those in which the target gene has been rendered nonfunctional by an insertion targeted to the gene to be rendered non-functional by targeting a pseudo-recombination site located within the gene sequence.

Gene Therapy and Disorders

A further embodiment of the invention comprises a method of treating a disorder in a subject in need of such treatment. In one embodiment of the method, at least one cell or cell type (or tissue, etc.) of the subject has a recombination site. This cell(s) is transformed with a nucleic acid construct (a "targeting construct") comprising a second recombination sequence and one or more polynucleotides of interest (typically a therapeutic gene). Into the same cell a recombinase is introduced that specifically recognizes the recombination sequences under conditions such that the nucleic acid sequence of interest is inserted into the genome via a recombination event between the first and second recombination sites. Subjects treatable using the methods of the invention include both humans and non-human animals. Such methods utilize the targeting constructs and recombinases of the present invention.

A variety of disorders may be treated by employing the method of the invention including monogenic disorders, infectious diseases, acquired disorders, cancer, and the like. Exemplary monogenic disorders include ADA deficiency, cystic fibrosis, familial-hypercholesterolemia, hemophilia, chronic ganulomatous disease, Duchenne muscular dystrophy, Fanconi anemia, sickle-cell anemia, Gaucher's disease, Hunter syndrome, X-linked SCID, and the like.

Infectious diseases treatable by employing the methods of the invention include infection with various types of virus including human T-cell lymphotropic virus, influenza virus, papilloma virus, hepatitis virus, herpes virus, Epstein-Bar virus, immunodeficiency viruses (HIV, and the like), cytomegalovirus, and the like. Also included are infections with other pathogenic organisms such as *Mycobacterium Tuberculosis*, *Mycoplasma pneumoniae*, and the like or parasites such as *Plasmadium falciparum*, and the like.

The term "acquired disorder" as used herein refers to a noncongenital disorder. Such disorders are generally considered more complex than monogenic disorders and may result from inappropriate or unwanted activity of one or more genes. Examples of such disorders include peripheral artery disease, rheumatoid arthritis, coronary artery disease, and the like.

A particular group of acquired disorders treatable by employing the methods of the invention include various cancers, including both solid tumors and hematopoietic cancers such as leukemias and lymphomas. Solid tumors that are treatable utilizing the invention method include carcinomas, sarcomas, osteomas, fibrosarcomas, chondrosarcomas, and the like. Specific cancers include breast cancer, brain cancer, lung cancer (non-small cell and small cell), colon cancer, pancreatic cancer, prostate cancer, gastric cancer, bladder cancer, kidney cancer, head and neck cancer, and the like.

The suitability of the particular place in the genome is dependent in part on the particular disorder being treated. For example, if the disorder is a monogenic disorder and the desired treatment is the addition of a therapeutic nucleic acid encoding a non-mutated form of the nucleic acid thought to be the causative agent of the disorder, a suitable place may be a region of the genome that does not encode any known protein and which allows for a reasonable expression level of the added nucleic acid. Methods of identifying suitable places in the genome are well known in the art and described further in the Examples below.

The nucleic acid construct useful in this embodiment is additionally comprised of one or more nucleic acid fragments of interest. Preferred nucleic acid fragments of interest for use in this embodiment are therapeutic genes and/or control regions, as previously defined. The choice of nucleic acid sequence will depend on the nature of the disorder to be treated. For example, a nucleic acid construct intended to treat hemophilia B, which is caused by a deficiency of coagulation factor IX, may comprise a nucleic acid fragment encoding functional factor IX. A nucleic acid construct intended to treat obstructive peripheral artery disease may comprise nucleic acid fragments encoding proteins that stimulate the growth of new blood vessels, such as, for example, vascular endothelial growth factor, platelet-derived growth factor, and the like. Those of skill in the art would readily recognize which nucleic acid fragments of interest would be useful in the treatment of a particular disorder.

The nucleic acid construct can be administered to the subject being treated using a variety of methods. Administration can take place in vivo or ex vivo. By "in vivo," it is meant in the living body of an animal. By "ex vivo" it is meant that cells or organs are modified outside of the body, such cells or organs are typically returned to a living body.

Methods for the therapeutic administration of nucleic acid constructs are well known in the art. Nucleic acid constructs can be delivered with cationic lipids (Goddard, et al, Gene Therapy, 4:1231-1236, 1997; Gorman, et al, Gene Therapy 4:983-992, 1997; Chadwick, et al, Gene Therapy 4:937-942, 1997; Gokhale, et al, Gene Therapy 4:1289-1299, 1997; Gao, and Huang, Gene Therapy 2:710-722, 1995, all of which are incorporated by reference herein), using viral vectors (Monahan, et al, Gene Therapy 4:4049, 1997; Onodera, et al, Blood 91:30-36, 1998, all of which are incorporated by reference herein), by uptake of "naked DNA", and the like. Techniques well known in the art for the transfection of cells (see discussion above) can be used for the ex vivo administration of nucleic acid constructs. The exact formulation, route of administration and dosage can be chosen by the individual physician in view of the patient's condition. (See e.g. Fingl et al., 1975, in "The Pharmacological Basis of Therapeutics", Ch. 1 p 1).

It should be noted that the attending physician would know how to and when to terminate, interrupt, or adjust administration due to toxicity, to organ dysfunction, and the like. Conversely, the attending physician would also know how to adjust treatment to higher levels if the clinical response were not adequate (precluding toxicity). The magnitude of an administered dose in the management of the disorder being treated will vary with the severity of the condition to be treated, with the route of administration, and the like. The severity of the condition may, for example, be evaluated, in part, by standard prognostic evaluation methods. Further, the dose and perhaps dose frequency will also vary according to the age, body weight, and response of the individual patient.

In general at least 1-10% of the cells targeted for genomic modification should be modified in the treatment of a disorder. Thus, the method and route of administration will optimally be chosen to modify at least 0.1-1% of the target cells per administration. In this way, the number of administrations can be held to a minimum in order to increase the efficiency and convenience of the treatment.

Depending on the specific conditions being treated, such agents may be formulated and administered systemically or locally. Techniques for formulation and administration may be found in "Remington's Pharmaceutical Sciences," 1990, 18th ed., Mack Publishing Co., Easton, Pa. Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few.

The subject being treated will additionally be administered a recombinase that specifically recognizes the first and second recombination sequences that are selected for use. The particular recombinase can be administered by including a nucleic acid encoding it as part of a nucleic acid construct, or as a protein to be taken up by the cells whose genome is to be modified. Methods and routes of administration will be similar to those described above for administration of a targeting construct comprising a recombination sequence and nucleic acid sequence of interest. The recombinase protein is likely to only be required for a limited period of time for integration of the nucleic acid sequence of interest. Therefore, if introduced as a recombinase gene, the vector carrying the recombinase gene will lack sequences mediating prolonged retention. For example, conventional plasmid DNA decays rapidly in most mammalian cells. The recombinase gene may also be equipped with gene expression sequences that limit its expression. For example, an inducible promoter can be used, so that recombinase expression can be temporally regulated by limited exposure to the inducing agent. One such exemplary group of promoters is ecdysone-responsive promoters, the expression of which can be regulated using ecdysteroids or other non-steroidal agonists. Another group of promoters are tetracycline-responsive promoters, the expression of which can be regulated using tetracycline or doxycycline.

EXAMPLES

General Methods

Standard recombinant DNA and molecular cloning techniques used herein are well known in the art and are described by Sambrook, J., Fritsch, E. F. and Maniatis, T. *Molecular Cloning. A Laboratory Manual*; Cold Spring Harbor Laboratory Press: Cold Spring Harbor, N.Y. (1989) and by T. J. Silhavy, M. L. Bennan, and L. W. Enquist, *Experiments with Gene Fusions*, Cold Spring Harbor Laboratory, Cold Spring Harbor, N.Y. (1984), and by Ausubel, F. M. et al., Current Protocols in Molecular Biology, Greene Publishing Assoc.

and Wiley-Interscience, New York, N.Y. (1987). Materials and methods suitable for the maintenance and growth of bacterial cultures are well known in the art. Techniques suitable for use in the following examples may be found as set out in Phillipp, G. et al., *Manual of Methods for General Bacteriology*, American Society for Microbiology, Washington, D.C. (1994) or in Brock, T. D. *Biotechnology: A Textbook of Industrial Microbiology*, Second Edition, Sinauer Associates, Inc., Sunderland, Mass. (1989). All reagents, restriction enzymes and materials used for the growth and maintenance of host cells were obtained from New England Biolabs (Beverly, Mass.), Invitrogen Corporation (Carlsbad, Calif.), Stratagene Corporation (La Jolla, Calif.), Promega Corporation (Madison, Wis.), DIFCO Laboratories (Detroit, Mich.), or Sigma/Aldrich Chemical Company (St. Louis, Mo.) unless otherwise specified.

Manipulations of genetic sequences and alignment and comparison of polynucleotide and peptide sequences can be accomplished using the suite of programs available from Invitrogen Corporation, Carlsbad, Calif. (Vector NTI software version 8.0), DNASTAR, Inc., Madison, Wis. (DNASTAR software version 6.0), or Genetics Computer Group Inc., Madison, Wis. (Wisconsin Package Version 9.0).

The meaning of abbreviations is as follows: "h" means hour(s), "μL" means microliter(s), "mL" means milliliter(s), "L" means liter(s), "μM" means micromolar, "mM" means millimolar, "ng" means nanogram(s), "μg" means microgram(s), "mg" means milligram(s), "A" means adenine or adenosine, "T" means thymine or thymidine, "G" means guanine or guanosine, "C" means cytidine or cytosine, "nt" means nucleotide(s), "aa" means amino acid(s), "bp" means base pair(s), "kb" means kilobase(s), "k" means kilo, "μ" means micro, "Φ" means Phi, "β" means beta, "SE" means standard error, "Luc" means firefly luciferase, "RLuc" means *Renilla* luciferase, and "° C." means degrees Celsius.

The following examples demonstrate that site-specific recombinase systems derived from *Bacillus subtilis* bacteriophage SPβc2, *Streptococcus pyogenes* bacteriophage SF370.1, *Mycobacterium smegmatis* bacteriophage Bxb1, *Listeria monocytogenes* bacteriophage A118, and *Mycobacterium tuberculosis* bacteriophage ΦRv1 function in eukaryotic cells. These examples are offered to illustrate, but not to limit the present invention.

Example 1

Design, Synthesis, and Cloning of Recombinase Genes and Intramolecular Recombination Assay Plasmids After analyzing the published literature and sequences available in Genbank, numerous site-specific recombinases were selected and assayed for DNA integration, excision, inversion, and replacement in mammalian and plant cells. The amino acid sequences for large site-specific recombinases of serine family (Smith, M. C. and H. M. Thorpe 2000 Diversity in the serine recombinases. Mol. Microbiol., 44:299-307) were obtained from GenBank and reverse translated to DNA. Since the sources of recombinases were from bacteria or bacterial viruses, we optimized the DNA sequence for recombinase expression in mammalian cells without changing the encoded amino acid sequence. The genes were totally synthesized using the codons for high-level human and mouse expression and with convenient restriction enzyme sites for cloning. In addition, regions of very high (>80%) or very low (<30%) GC content have been avoided where possible. Moreover, during the optimization the following cis-acting sequence motifs were avoided to optimize RNA stability and translation:
  internal TATA-boxes, chi-sites and ribosomal entry sites
  AT-rich or GC-rich sequence stretches
  repeat sequences and RNA secondary structures
  (cryptic) splice donor and acceptor sites, branch points
  poly(A) sites The codon and RNA optimization resulted in difference of 20-30% of sequence between native (i.e., DNA sequence available at Genbank) and synthetic genes. The synthetic genes encoding the recombinases were cloned into mammalian and *E. coli* expression plasmid pDual obtained from Stratagene Corporation (La Jolla, Calif., catalog #214501). pDual expression vector directs expression of heterologous genes in both mammalian and prokaryotic cells. For the constitutive expression in mammalian cells the vector contains the promoter/enhancer of the human cytomegalovirus (CMV) immediate early gene. The recombinase gene is cloned at the unique Earn 1104 I restriction enzyme site present between the CMV promoter and SV40 terminator sequence. While synthesizing the gene sequences we added Earn 1104 I restriction enzyme recognition site at the beginning (before the initiation codon ATG) and end (after the stop codon TAG) of the gene to facilitate digestion with Earn 1104 I enzyme and cloning at the same site in the pDual plasmid. The cloning of synthetic genes, sequencing of clones to confirm the gene sequence after cloning into pDual vector were performed using the standard DNA cloning procedures (Sambrook, J., E. F. Fritsch, et al. 1989. *Molecular Cloning: A laboratory Manual*. Cold Spring Harbor Press, Cold Spring Harbor, N.Y.). The description of expression plasmids is given below.

1.1 SPbc2 Recombinase Expression Plasmid: A synthetic DNA sequence (SEQ ID NO: 1) codon optimized for animal cell expression and encoding the site-specific DNA recombinase yokA of *Bacillus subtilis* phage SPβc2 (SEQ ID NO: 2, Genbank accession #T12765, Lazarevic, V., A. Dusterhoft, et al. 1999, Nucleotide sequence of the *Bacillus subtilis* temperate bacteriophage SPβc2. Microbiology 145:1055-67) was cloned into pDual expression vector at Earn 1104 I restriction site following the procedures recommended by Stratagene (La Jolla, Calif.).

1.2 SF370.1 Recombinase Expression Plasmid: A synthetic DNA sequence (SEQ ID NO: 3) codon optimized for animal cell expression and encoding the putative recombinase of *Streptococcus pyogenes* bacteriophage SF370.1 (SEQ ID NO: 4, Genbank accession #T12765, Canchaya, C., F. Desiere, et al. 2002, Genome analysis of an inducible prophage and prophage remnants integrated in the *Streptococcus pyogenes* strain SF370. Virology 302:245-58) was cloned into pDual expression vector at Earn 1104 I restriction site following the procedures recommended by Stratagene (La Jolla, Calif.).

1.3 Bxb1 Recombinase Expression Plasmid: A synthetic DNA sequence (SEQ ID NO: 5) codon optimized for animal cell expression and encoding the putative recombinase of *Mycobacterium smegmatis* bacteriophage Bxb1 (SEQ ID NO: 6, Genbank accession # AAG59740, Mediavilla, J., S. Jain, et al. 2000, Genome organization and characterization of mycobacteriophage Bxb1. Mol. Microbiol. 38:955-70) was cloned into pDual expression vector at Earn 1104 I restriction site following the procedures recommended by Stratagene (La Jolla, Calif.).

1.4 A118 Recombinase Expression Plasmid: A synthetic DNA sequence (SEQ ID NO: 7) codon optimized for animal cell expression and encoding the putative recombinase of

*Listeria monocytogenes* bacteriophage A118 (SEQ ID NO: 8, Genbank accession # CAB53817, Loessner, M. J., R. B. Inman, et al. 2000, Complete nucleotide sequence, molecular analysis and genome structure of bacteriophage A118 of *Listeria monocytogenes*: implications for phage evolution. Mol. Microbiol. 35:324-40) was cloned into pDual expression vector at Earn 1104 I restriction site following the procedures recommended by Stratagene (La Jolla, Calif.).

1.5 ΦRv1 Recombinase Expression Plasmid: A synthetic DNA sequence (SEQ ID NO: 9) codon optimized for animal cell expression and encoding the putative recombinase of and *Mycobacterium tuberculosis* bacteriophage ΦRv1 (SEQ ID NO: 10, Genbank accession #CAB09083, Bibb, L. A. and G. F. Hatfull 2002, Integration and excision of the *Mycobacterium tuberculosis* prophage-like element, phiRv1. Mol. Microbiol. 45:1515-26) was cloned into pDual expression vector at Earn 1104 I restriction site following the procedures recommended by Stratagene (La Jolla, Calif.).

1.6 A118 Recombinase Plant Expression Plasmid: A synthetic DNA sequence (SEQ ID NO: 7) codon optimized for animal cell expression and encoding the putative recombinase of *Listeria monocytogenes* bacteriophages A118 was cloned into plant expression plasmid pILTAB358 between the cassava vein mosaic promoter NOS terminator sequence (Verdaguer, B., A. Kochko et al. 1998, Functional organization of the cassava vein mosaic virus (CsVMV) promoter. Plant Mol. Biol. 37:1055-67). pILTAB plasmid DNA was obtained from Donald Danforth Center for Plant Research, St. Louis, Mo. The constructs are similar to the A118 expression plasmid used in animal cells except that the CMV promoter and SV40 terminator were replaced with cassava vein mosaic promoter and 35S terminator, respectively.

Design and Construction of Intramolecular Recombination Assay Plasmids

Intramolecular recombination assay plasmids were constructed using the plasmid gWiz™ Luc (Gene Therapy Systems, San Diego, Calif.). This plasmid confers kanamycin resistance in *E. coli* and expresses a luciferase gene constitutively from the CMV promoter when introduced into mammalian cells. The vector also contains unique Sal I and Not I restriction sites between the CMV promoter and start codon of luciferase gene. Recognition sites for restriction enzymes Apa I and Nhe I were created by inserting an oligonucleotide between the Sal I and Not I sites. Oligonucleotides containing the attP site of recombinase and having Sal I and Apa I flanking restriction sites were synthesized, annealed, and inserted between the Sal and Apa I sites. Similarly, oligonucleotides containing the attB sequence were inserted between the Nhe I and Not I sites. A 1296 bp transcriptional termination or STOP sequence was PCR amplified from plasmid pBS302 (Genbank accession # U51223, nucleotides 193-1488) and cloned at Apa I and Nhe I sites, between attP and attB sites. The final construct had the attP, STOP, and attB sequences placed between the CMV promoter and luciferase gene as shown in FIG. 1. The plasmid would express luciferase gene only after the deletion of STOP sequence due to recombination between attP and attB sites. The description of intramolecular recombination assay plasmids is given below.

1.7 SPβc2 Intramolecular Recombination Assay Plasmid: A 99 bp synthetic oligonucleotide sequence containing the attP site of SPβc2 recombinase (SEQ ID NO: 1), a 1296 bp STOP sequence (SEQ ID NO: 12), and a 96 bp synthetic oligonucleotide sequence containing the attB site (SEQ ID NO: 13) of SPβc2 recombinase were cloned in that order between the CMV promoter and luciferase gene of gWiZ™ Luc plasmid.

1.8 SF370.1 Intramolecular Recombination Assay Plasmid: A 99 bp synthetic oligonucleotide sequence containing the attP site of SF370.1 recombinase (SEQ ID NO: 14), a 1296 bp STOP sequence (SEQ ID NO: 12), and a 96 bp synthetic oligonucleotide sequence containing the attB site (SEQ ID NO: 15) of SF370.1 recombinase were cloned in that order between the CMV promoter and luciferase gene of gWiz™ Luc plasmid.

1.9 Bxb1 Intramolecular Recombination Assay Plasmid: A 52 bp synthetic oligonucleotide sequence containing the attP site of Bxb1 recombinase (SEQ ID NO: 16), a 1296 bp STOP sequence (SEQ ID NO: 12), and a 46 bp synthetic oligonucleotide sequence containing the attB site (SEQ ID NO: 17) of Bxb1 recombinase were cloned in that order between the CMV promoter and luciferase gene of gWiZ™ Luc plasmid.

1.10 A118 Intramolecular Recombination Assay Plasmid: A 99 bp synthetic oligonucleotide sequence containing the attP site of A118 recombinase (SEQ ID NO: 18), a 1296 bp STOP sequence (SEQ ID NO: 12), and a 96 bp synthetic oligonucleotide sequence containing the attB site (SEQ ID NO: 19) of A118 recombinase were cloned in that order between the CMV promoter and luciferase gene of gWiZ™ Luc plasmid.

1.11 ΦRv1 Intramolecular Recombination Assay Plasmid: A 99 bp synthetic oligonucleotide sequence containing the attP site of ΦRv1 recombinase (SEQ ID NO: 20), a 1296 bp STOP sequence (SEQ ID NO: 12), and a 96 bp synthetic oligonucleotide sequence containing the attB site (SEQ ID NO: 21) of ΦRv1 recombinase were cloned in that order between the CMV promoter and luciferase gene of gWiZ™ Luc plasmid.

1.12 A118 Intramolecular Recombination Assay Plant Plasmid: A 99 bp synthetic oligonucleotide sequence containing the attP site of A118 recombinase (SEQ ID NO: 18), a 1296 bp STOP sequence (SEQ ID NO: 12), a 96 bp synthetic oligonucleotide sequence containing the attB site (SEQ ID NO: 19) of A118 recombinase, and luciferase gene were cloned in that order between the cassava vein mosaic promoter and NOS terminator sequence of pILTAB358.

Example 2

Transient Intramolecular Recombination Assays

In order to determine the activity of the recombinases in mammalian and plant cells, a transient assay was developed. Briefly, the assay consisted of cloning the recombinase gene into an expression plasmid, making the corresponding intramolecular recombination assay plasmid, introducing both plasmid DNAs into cells by transfection, and assaying for luciferase enzyme activity. The recombinase assay plasmids contained CMV Promoter—attP:STOP:attB—Luciferase Reporter gene—Terminator sequences. The STOP sequence is a transcription termination signal sequence. In the absence of recombination, expression of the luciferase reporter gene is prevented by the STOP sequence present between the promoter and reporter gene. Recombination between the attP and attB sites due to the introduced recombinase results in deletion of the STOP sequence and activation of reporter gene. This assay is sensitive and robust because it is an OFF to ON format and the amount of luciferase reporter can be easily assayed by detecting the light emitted by luciferase with a luminometer. The assay format is graphically depicted in FIG. 1.

Transient Transfections and Luciferase Assays

Cells were maintained at 37° C. and 5% $CO_2$ in DMEM supplemented with 10% fetal bovine serum and 1% penicillin/streptomycin (obtained from Invitrogen, Carlsbad, Calif.) or in other media as indicated. On the day of transfection, cells were plated at different densities depending on the cell type used. The cells were transfected with intramolecular recombination assay plasmid alone or along with varying amounts of recombinase expression plasmid DNA using Lipofectamine 2000™ according to the manufacturers instructions (Invitrogen, Carlsbad, Calif.). Constitutively expressed *Renilla* luciferase reporter plasmid (pRL-CMV from Promega, Madison, Wis.) was co-transfected (2 ng/well) and used as an internal control to normalize the data. Twenty-four or forty-eight hours after transfection (depending on the cell line), media was discarded and cells were lysed with passive lysis buffer (Promega, Madison, Wis.). Extracts were then assayed using Dual Luciferase Assay kit (Promega, Madison, Wis.) on a plate reader equipped with injectors (Dynex Technologies, Chantilly, Va.). The data shown are the ratios of luciferase (Luc) and *Renilla* luciferase (RLuc) activities, unless noted otherwise. Similar results were observed when Luc activities (relative light units) were compared (data not shown). Since the number of replicates and experiments varied for different constructs and cell lines the standard error was used to indicate the experimental variation.

2.1 Transient Intramolecular Recombination Assay in Human HEK293 Cells

Cells (20,000 cells per well in a 96-well plate) were transfected with 25 ng of intramolecular recombination assay plasmid and 0, 10, 25, or 75 ng of the corresponding recombinase plasmid and incubated for 24 hours. Cells were lysed with 50 µl of passive lysis buffer and 25 µl extracts were assayed. Six to twenty replicate assays were performed, and ratios of Luc/RLuc (mean values)±SE were plotted. The values shown above the bars in FIG. 2 are fold inductions (ratio of luciferase activity in the presence of recombinase plasmid to the activity in the absence of recombinase plasmid).

Figure 2:
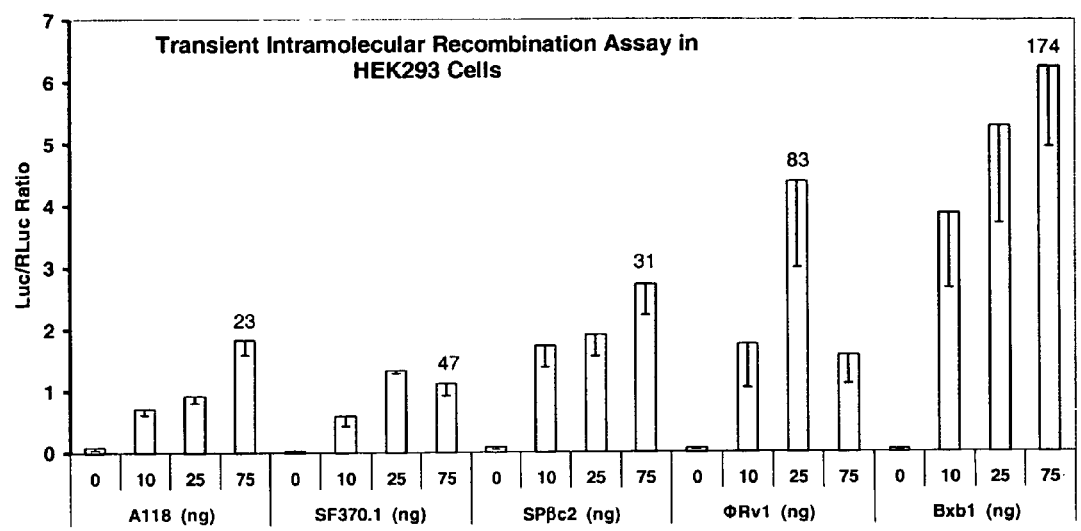
FIG. 2 demonstrates the results of the TIRA for various recombinases performed in human embryonic kidney (HEK293) cells.

As shown in FIG. 2, transfection of intramolecular recombination assay plasmid alone showed no or very little luciferase activity (given as ratio of Luc/RLuc). Transfection of increasing amounts of A118 recombinase expression plasmid (10, 25, or 75 ng) along with A118 intramolecular recombination assay plasmid increased the luciferase activity. Similar results were also observed for SF370.1, SPβc2, ΦRV1, and Bxb1. These results clearly indicated that the recombinases are functional in HEK293 cells. The recombinases mediated the recombination between their attP and attB sites and deleted the STOP sequence on the intramolecular recombination assay plasmid and activated the luciferase gene expression.

2.2 Transient Intramolecular Recombination Assay in Mouse NIH3T3 Cells

Cells (5,000 cells per well in a 96-well plate) were transfected with 25 ng of intramolecular recombination assay plasmid and 0, 10, 25, or 75 ng of the corresponding recombinase expression plasmid and incubated for 24 hours. Cells were lysed with 50 µl of passive lysis buffer and 25 µl extracts were assayed. Two to fourteen replicate assays were performed, and ratios of Luc/RLuc (mean values)±SE were plotted. The values shown above the bars in FIG. 3 are fold inductions.

Figure 3:
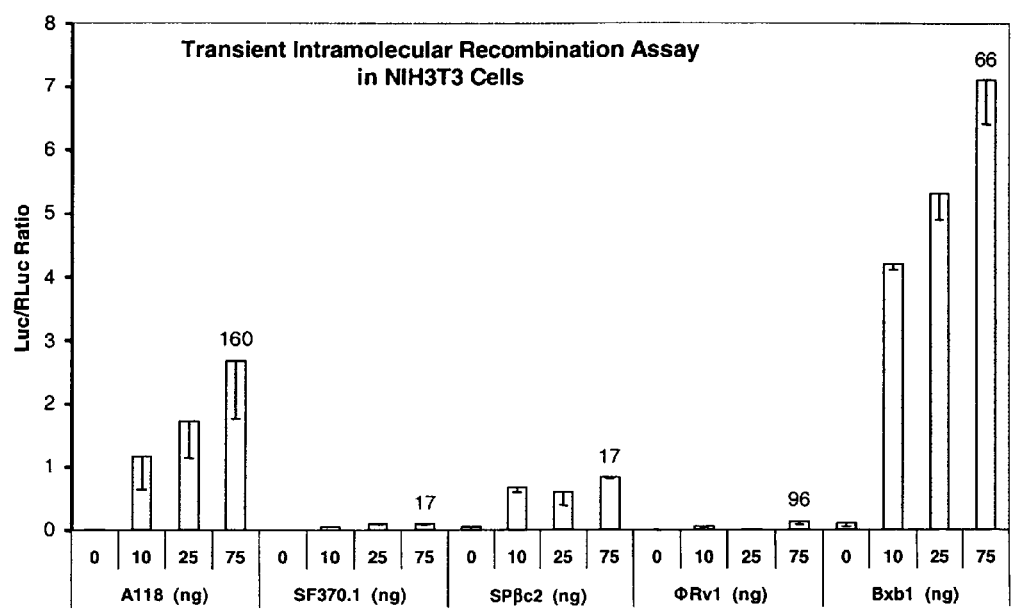
FIG. 3 demonstrates the results of the TIRA for various recombinases performed in mouse NIH3T3 cells.

FIG. 3 shows the data obtained from transfection of NIH3T3 with intramolecular recombination assay plasmid alone or along with increasing amounts (10, 25, or 75 ng) of recombinase expression plasmid. Co-transfection of recombinase plasmid and intramolecular recombination assay plasmid increased the luciferase activity many fold. For example, transfection of cells with 25 ng Bxb1 intramolecular recombination assay plasmid and 75 ng of Bxb1 recombinase expression plasmid increased the luciferase activity 66-fold when compared with transfection with 25 ng Bxb1 intramolecular recombination assay plasmid alone. Similar to Bxb1, recombinases A118, SF370.1, SPβc2, and ΦRV1 also increased the luciferase activity (FIG. 3) showing that these recombinases are functional in mouse NIH3T3 cells and are effective at recombining their attP and attB sites.

2.3 Transient Intramolecular Recombination Assay in Chinese Hamster Ovary (CHO) Cells Cells (15,000 cells per well in a 96-well plate) were transfected with 25 ng of intramolecular recombination assay plasmid and 0, 10, 25, or 75 ng of the corresponding recombinase expression plasmid and incubated for 24 hours. Cells were lysed with 50 µl of passive lysis buffer and 25 µl extracts were assayed. Two to eight replicate assays were performed, and ratios of Luc/RLuc (mean values)±SE were plotted. The values shown above the bars in FIG. 4 are fold inductions.

Figure 4:
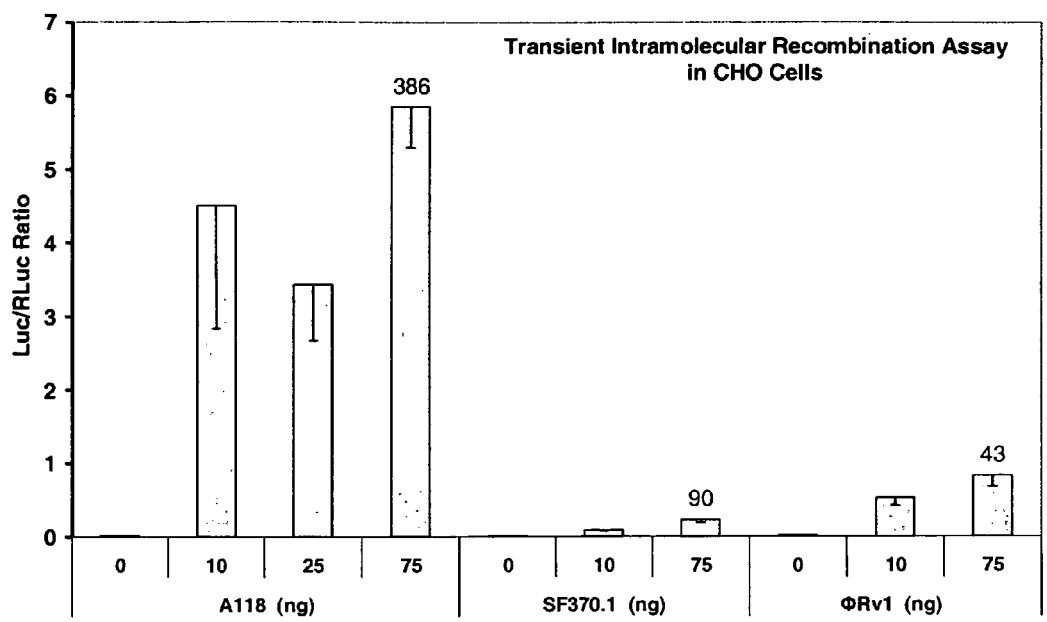
FIG. 4 demonstrates the results of the TIRA for various recombinases performed in Chinese hamster ovary (CHO) cells.

As shown in FIG. 4, transfection of intramolecular recombination assay plasmid of A118, SF370.1, or ΦRV1 alone showed no or very little luciferase activity. Co-transfection with increasing amounts of corresponding A118, SF370.1, or ΦRV1 recombinase expression plasmid increased the luciferase activity. These results clearly indicated that the recombinases are functional in CHO cells. The recombinases mediated the recombination between their attP and attB sites and deleted the STOP sequence on the intramolecular recombination assay plasmid and activated the luciferase gene expression.

2.4 Transient Intramolecular Recombination Assay in Human HeLa Cells

Cells (15,000 cells per well in a 96-well plate) were transfected with 25 ng of intramolecular recombination assay plasmid and 0, 10, 25, or 75 ng of the corresponding recombinase expression plasmid and incubated for 24 hours. Two to eight replicate assays were performed, and ratios of Luc/RLuc (mean values)±SE were plotted. The values shown above the bars in FIG. 5 are fold inductions.

Figure 5:
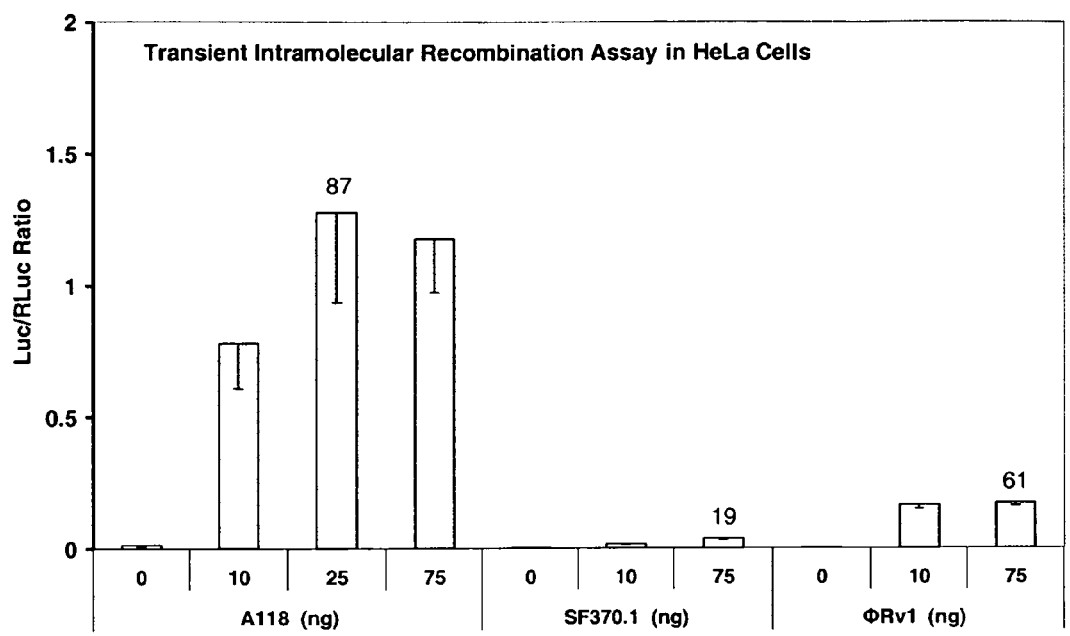
FIG. 5 demonstrates the results of the TIRA for various recombinases performed in human HeLa cells.

As shown in FIG. 5, transfection of intramolecular recombination assay plasmid of A118, SF370.1, or ΦRV1 alone showed no or very little luciferase activity. Co-transfection with increasing amounts of corresponding A118, SF370.1, or ΦRV1 recombinase expression plasmid increased the luciferase activity. These results showed that the recombinases are functional in HeLa cells.

2.5 Transient Intramolecular Recombination Assay in Rat Bone Marrow Stromal Cells Primary bone marrow stromal cells from rats were preplated one day before the transfection at a density of 4000 cells/cm$^2$ and cultured in medium containing 50% Minimum Essential Medium Alpha Medium (αMEM), 50% F12 Hams, 10% FBS, 1% Pen/Strep (100 U/ml penicillin G and 100 mg/ml streptomycin sulfate). Cells were transfected with 25 ng of intramolecular recombination assay plasmid and 0, 50, 100, or 200 ng of the corresponding recombinase plasmid and incubated for 48 hours. Cells were lysed with 50 µl of passive lysis buffer and 25 µl extracts were assayed. Eight replicate assays were performed, and ratios of Luc/RLuc (mean values)±SE were plotted. The values shown above the bars in FIG. 6 are fold inductions.

Figure 6:
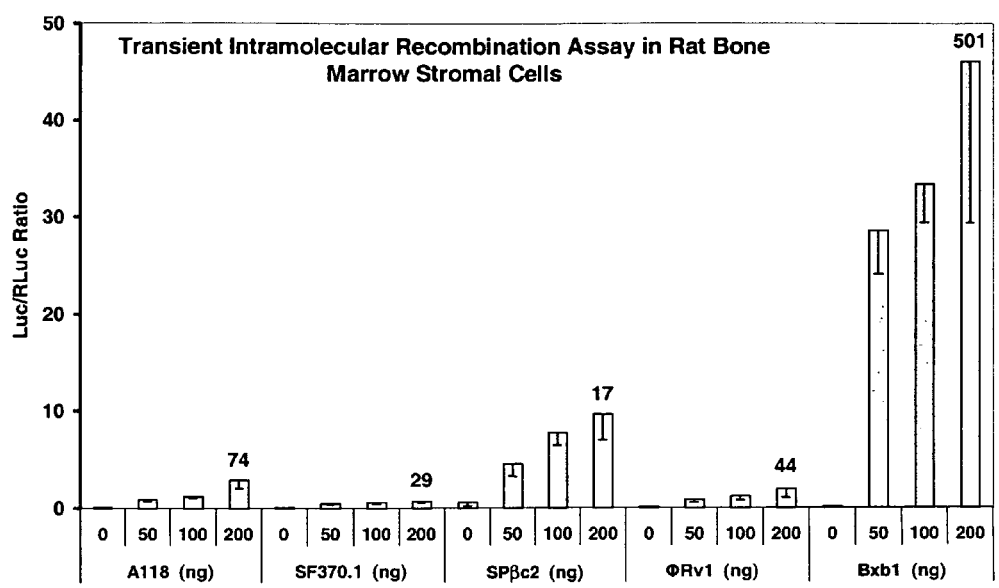
FIG. 6 demonstrates the results of the TIRA for various recombinases performed in rat bone marrow stromal cells.

FIG. 6 shows the data obtained from transfection of rat bone marrow stromal cells with intramolecular recombination assay plasmid alone or along with increasing amounts (50, 100, or 200 ng) of corresponding recombinase expression plasmid. Co-transfection of intramolecular recombination assay plasmid and recombinase expression plasmid increased the luciferase activity many fold. For example, transfection of cells with 25 ng Bxb1 intramolecular recombination assay plasmid and 200 ng of Bxb1 recombinase expression plasmid increased the luciferase activity 501-fold when compared to transfection with 25 ng Bxb1 intramolecular recombination assay plasmid alone. Similar to Bxb1, recombinases A118, SF370.1, SPβc2, and ΦRV1 also increased the luciferase activity (FIG. 6) showing that these recombinases are functional in rat bone marrow stromal cells and are effective at recombining their attP and attB sites.

2.6 Transient Intramolecular Recombination Assay in Mouse Neural Stem Cells

Figure 7:
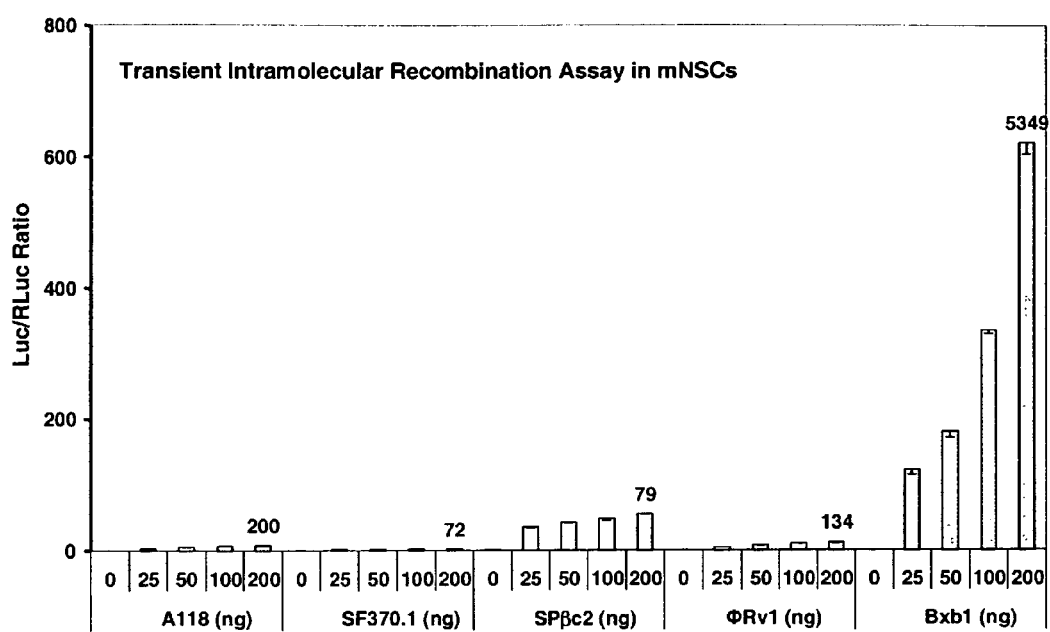
FIG. 7 demonstrates the results of the TIRA for various recombinases performed in mouse neural stem cells.

Mouse neural stem C17.2 cells (mNSCs) were obtained from Dr. Evan Snyder of The Burnham Research Institute, La Jolla, Calif. and maintained using the recommended protocol (Ryder, E. F., E. Y. Snyder, et al. 1990. Establishment and characterization of multipotent neural cell lines using retrovirus vector-mediated oncogene transfer. J. Neurobiol., 21:356-75). Cells were split one day prior to transfection and plated in 48-well plates at a density of 120,000 cells per well. After overnight incubation the culture media was replaced with serum-free medium. The cells were transfected with 50 ng intramolecular recombination assay plasmid alone or along with 0, 25, 50, 100, or 200 ng of recombinase plasmid DNA using transfection reagent Lipofectamine 2000™ according to the manufacturers instructions (Invitrogen, Carlsbad, Calif.). Constitutively expressed Renilla luciferase reporter plasmid (pRL-CMV, Promega, Madison, Wis.) was co-transfected (4 ng/well) as an internal control to normalize the data. Two days after transfection, the media was discarded and cells were lysed with 75 µl of passive lysis buffer (Promega, Madison, Wis.). Extracts (50 µl) were assayed for luciferase and Renilla luciferase activities using the Dual Luciferase Assay kit (Promega, Madison, Wis.) on a plate reader equipped with injectors (Dynex Technologies, Chantilly, Va.). The data shown in FIG. 7 are the ratios of luciferase (Luc) and Renilla luciferase (RLuc) activities, and is the average of 4 transfections per treatment. Error bars represent standard error.

Similar to results observed in HEK293, NIH3T3, CHO, HeLa, and rat bone marrow stromal cells, recombinases A118, SF370.1, SPβc2, φRV1, and Bxb1 were functional in mNSCs and increased the luciferase activity (FIG. 7). Co-transfection of increasing amounts (25, 50, 100, or 200 ng) of recombinase expression plasmid with corresponding intramolecular recombination assay plasmid (50 ng) resulted in higher luciferase activities and the fold inductions ranged from 72-5349.

2.7 Transient Intramolecular Recombination Assay in Tobacco BY2 Cells

Figure 8:
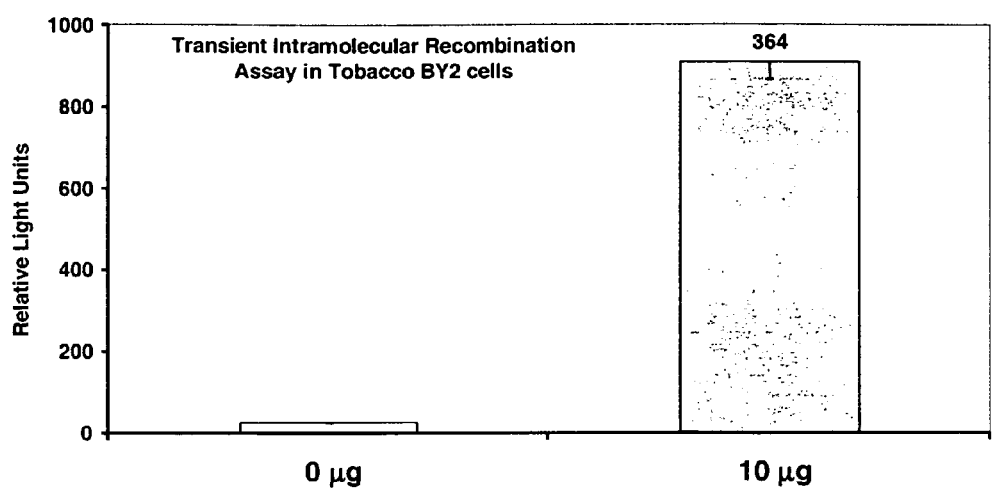
FIG. 8 demonstrates the results of the TIRA assay for A118 recombinase performed in tobacco BY2 cells.

Cell suspension cultures of Nicotiana tobacum BY2 were maintained in MS medium in the dark and subcultured weekly (Nagata, T., T. Nemoto, and S. Hasezawa. 1992. Tobacco BY-2 cell line as the Hela cell in the cell biology of higher plants. Intl. Rev. Cytol., 132:1-30). Protoplasts prepared from 3 day-old cultures were resuspended in 0.4 M mannitol and distributed into 35 mm petri dishes in 1 mL aliquots (~5×10$^5$ cells). Protoplasts were mixed with plasmid DNA and electroporated at 0.56 K Volts for 80µ seconds using a square wave electroporation system with Petripulser electrode (BTX, San Diego, Calif., USA). The cells were transfected with 10 µg for the intramolecular recombination test plasmid and 0 or 10 µg for the recombinase expression plasmid. Following the electroporation, protoplasts were diluted with 1 mL of 2× protoplast culture medium (Watanabe, Y., T. Meshi, and Y. Okada. 1987. Infection of tobacco protoplasts with in vitro transcribed tobacco mosaic virus RNA using an improved electroporation method. Virology, 192:264-272), aliquoted as two 1 mL cultures, and incubated at 27° C. for 17 h. Protoplasts were lysed by freeze thawing and addition of 250 µL 5× passive lysis buffer (Promega, Madison, Wis., USA). Twenty µL of cell extract was assayed for luciferase activity using Dual Luciferase Assay kit on a plate reader equipped with injectors. The data shown in FIG. 8 are the relative light units due to luciferase activity. The values shown are average of 22 replicates and the error bars are standard error.

As shown in FIG. 8, transfection of BY2 cells with A118 intramolecular recombination plant assay plasmid alone showed very little luciferase activity. Co-transfection with A118 recombinase plant expression plasmid resulted in 364-fold increase in luciferase activity. The data clearly indicated that the recombinase recombined attP and attB sites in plant cells.

Example 3

Stable Integration of Plasmid DNA Containing attP or attB Sequence Into HEK293 Chromosome Containing the attB OR attP Site Assay for the integration of plasmid DNA at attP or attB site on the chromosome was done in a two-step process. In the first step, a stable cell line containing a single copy of attP or attB site of each enzyme was generated and characterized. In the second step, a plasmid containing the attP or attB site was integrated at the chromosomal attB or attP, respectively, in the presence of the recombinase expression plasmid.

Generation of Stable HEK293 Clones with attP or attB Sequence in the Chromosome

Figure 9:
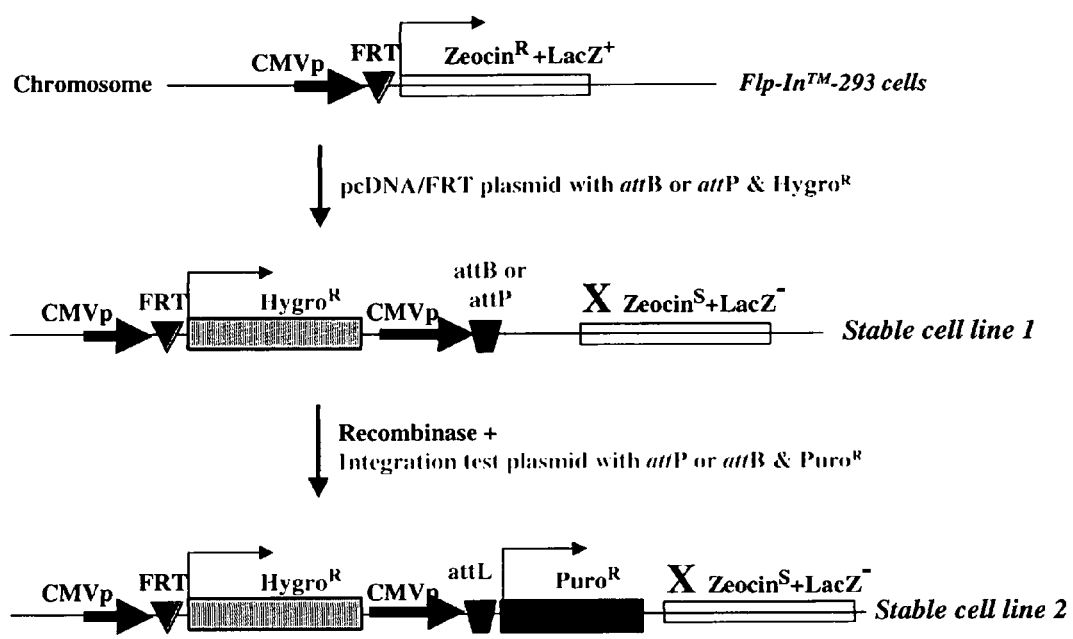
FIG. 9 depicts a schematic representation of stable integration of plasmid DNA containing attP or attB sequence into HEK293 chromosome containing the attB or attP site.

A single copy of attP or attB sequence of each recombinase (SEQ ID Numbers 11, 13-21) was introduced at the FRT locus in Flp-In™-293 cells obtained from Invitrogen [Carlsbad, Calif. (catalog #R750-07)] following the procedure recommended by the manufacturer. The FRT locus in Flp-In™-293 cells has a CMV promoter, FRT integration site for Flp recombinase, and zeocin resistance and β-galactosidase fusion gene. These cells grow in the presence of zeocin antibiotic and express β-galactosidase marker gene. The attP or attB sequence of each enzyme was cloned into pcDNA/FRT plasmid (Invitrogen, Carlsbad, Calif., catalog #V6010-20) at the multiple cloning sites region present between the CMV promoter and BGH terminator sequence. The pcDNA/FRT cloning plasmid has a FRT site preceding the hygromycin gene. The hygromycin gene lacks a promoter and ATG initiation codon. Therefore, transfection of pcDNA/FRT plasmid containing the attP or attB site into mammalian cells will not confer hygromycin resistance. The integration of pcDNA/FRT plasmid occurs at the FRT locus in Flp-In™-293 cells only following co-transfection with the Flp recombinase expression plasmid (pCG44, Invitrogen, Carlsbad, Calif.). Integration results in gain of hygromycin resistance and loss of zeocin resistance and β-galactosidase expression. The procedure is schematically shown in FIG. 9.

Figure 10:
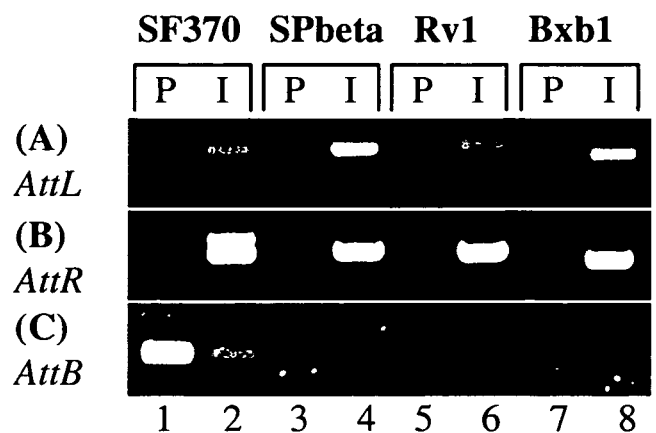
FIG. 10 demonstrates the results of PCR amplification of attL and attR sites following stable integration of plasmid DNA containing attP or attB sequence into HEK293 cell chromosome containing the attB or attP site.
Figure 10:
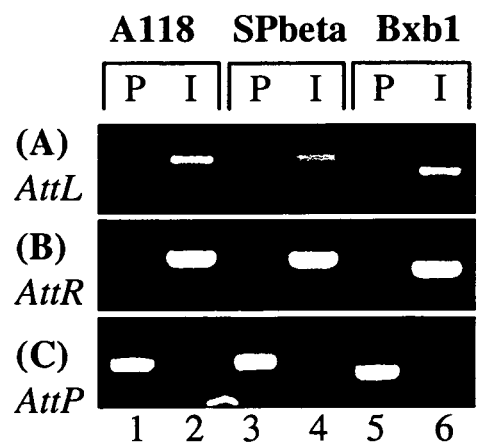

The attP or attb containing pcDNA/FRT plasmid DNAs were integrated into Flp-In™-293 cells and clonal lines for each attP or attB site were selected on media containing the hygromycin. As expected, these cells lost the β-galactosidase activity and were sensitive to zeocin. The presence of pcDNA/FRT plasmid with attP or attB sequence at the FRT locus was also confirmed by PCR (FIG. 10). In PCR analysis, we detected integration of attP or attB sequence at the FRT locus in the genome by using a primer that binds to attP or attB and another primer that binds to adjacent FRT locus sequence. Therefore, the clone would be PCR positive only if attP or attB site is integrated in the chromosome. As expected, the selected lines are positive for attP or attB. PCR did not amplify a specific band from the genomic DNA isolated from the parental Flp-In™-293 cells (lanes P, Panel C in FIG. 10)

but amplified a band from the DNA isolated from cells integrated with attP or attB containing pcDNA/FRT plasmid (lanes I, panel C in FIG. 10) for each recombinase tested. The stable 293 cells with attP or attB sites were used for integrating plasmid containing the attB or attP sites, respectively.

Integration of Plasmid DNA at Chromosomal attP or attB Site

The integration assay plasmids were constructed by placing attP or attB sequence of each recombinase immediately before the puromycin resistance gene. In this plasmid, the puromycin gene does not have its own promoter. However, recombination between the attP on the chromosome and attB in the integration assay plasmid (or attB on the chromosome and attP on the assay plasmid) would integrate the puromycin gene next to the CMV promoter present immediately before the attP or attB site in the Flp-In™-293 cells generated above (FIG. 9). The integration will result in expression of puromycin gene and growth of such cells in the presence of puromycin antibiotic. Random integration of assay plasmid is not expected to provide resistance to puromycin. The Flp-In™-293 stable cell line containing the attP sequence was transfected with integration assay plasmid containing the attB site and with or without the corresponding recombinase expression plasmid using the standard protocols. In another instance, Flp-In™-293 stable cell line with stably integrated attB sequence were generated and used for integrating the attP containing integration assay plasmid. Flp-In™-293 cells containing chromosomal attP or attB site (150,000 to 300,000 cells) were transfected with 100 ng integration assay plasmid and 400 ng of recombinase expression plasmid. Cells were then selected on medium containing the puromycin antibiotic. If the recombinase is functional, the attB sequence containing plasmid is expected to integrate at the attP site on the chromosome or vice versa.

The number of puromycin resistant colonies obtained from attB or attP site containing Flp-In™-293 cells after co-transfection with attP or attB-containing integration assay plasmid and the corresponding recombinase expression plasmid in 3 independent experiments is shown in Tables 1 and 2 below. In the absence of recombinase plasmid, no puromycin resistant colonies were observed. These results clearly showed that the recombinases facilitated recombination between chromosomal attP or attB site and plasmid attB or attP site, resulting in integration of plasmid DNA into chromosome. We also confirmed the plasmid integration by isolating genomic DNA from puromycin resistant clones and detected the presence of attL and attR sites on the chromosome. Recombination between attB and attP results in creation of attL and attR sites, which are hybrid sites between attB and attP. PCR amplification using the attL or attR specific primers amplified the expected specific band only in puromycin resistant clones after the integration of assay plasmid (lanes I, panels A and B in FIG. 10) but not in parental cells containing attP or attB that were used for integration (lanes P, panels A and B in FIG. 10).

TABLE 1

Integration of attP containing plasmid into chromosome with attB site

| Recombinase | Chromosomal site | Site on assay plasmid | Number of puromycin$^R$ clones | | |
|---|---|---|---|---|---|
| | | | Exp #1 | Exp #2 | Exp #3 |
| A118 | attB | attP | 28 | 12 | 0 |
| SF370.1 | attB | attP | Not done | 48 | 148 |
| SPβc2 | attB | attP | 77 | 303 | 270 |
| ΦRv1 | attB | attP | 4 | 9 | 0 |
| Bxb1 | attB | attP | 4 | 3 | 12 |

TABLE 2

Integration of attB containing plasmid into chromosome with attP site

| Recombinase | Chromosomal site | Site on assay plasmid | Number of puromycin$^R$ clones | | |
|---|---|---|---|---|---|
| | | | Exp #1 | Exp #2 | Exp #3 |
| A118 | attP | attB | 34 | 55 | 26 |
| SF370.1 | attP | attB | 0 | 2 | 2 |
| SPβc2 | attP | attB | 268 | 293 | 445 |
| Bxb1 | attP | attB | 12 | 8 | Not done |

Example 4

Deletion of Chromosomal DNA Flanked by attP AND attB Sites

Assay for the deletion of attP:STOP:attB sequence located on the chromosome was done in a two-step process. In the first step, stable cell lines containing a single copy of CMV promoter—attP:STOP:attB—Luciferase gene—Terminator construct were generated for each recombinase and characterized. In the second step, recombinase expression plasmid was transiently transfected into stable cells with CMV promoter—attP:STOP:attB—Luciferase gene—Terminator and the cells were assayed for the luciferase activity. If the recombinase is active in mammalian cells, the recombination between chromosomal attP and attB sites will result in the deletion of STOP sequence and activation of luciferase expression. The assay format is graphically depicted in FIG. 11.

Generation of Stable HEK293 Clones with CMV Promoter-attP-STOP-attB-Luciferase Gene Construct in the Chromosome A single copy of CMV promoter—attP:STOP:attB—Luciferase gene—Terminator construct was introduced at the FRT locus of Flp-In™-293 cells obtained from Invitrogen, Carlsbad, Calif. (catalog #R750-07) as described above. The attP:STOP:attB—Luciferase gene sequence of each recombinase that was present in transient intramolecular recombination assay plasmids (see Design and construction of intramolecular recombination assay plasmids and FIG. 1) was cloned into pcDNA/FRT plasmid (Invitrogen, Carlsbad, Calif., catalog #V6010-20) at the multiple cloning sites region present between the between CMV promoter and BGH terminator sequence. The constructed pcDNA/FRT plasmid with CMV promoter—attP:STOP:attB—Luciferase gene—Terminator was inserted at the FRT locus of Flp-In™-293 cells using Flp recombinase. Integration of this plasmid results in gain of hygromycin resistance and loss of zeocin resistance and β-galactosidase expression.

Flp-In™-293 cells were transfected with pcDNA/FRT plasmid containing the CMV promoter—attP:STOP:attB—

Figure 11:
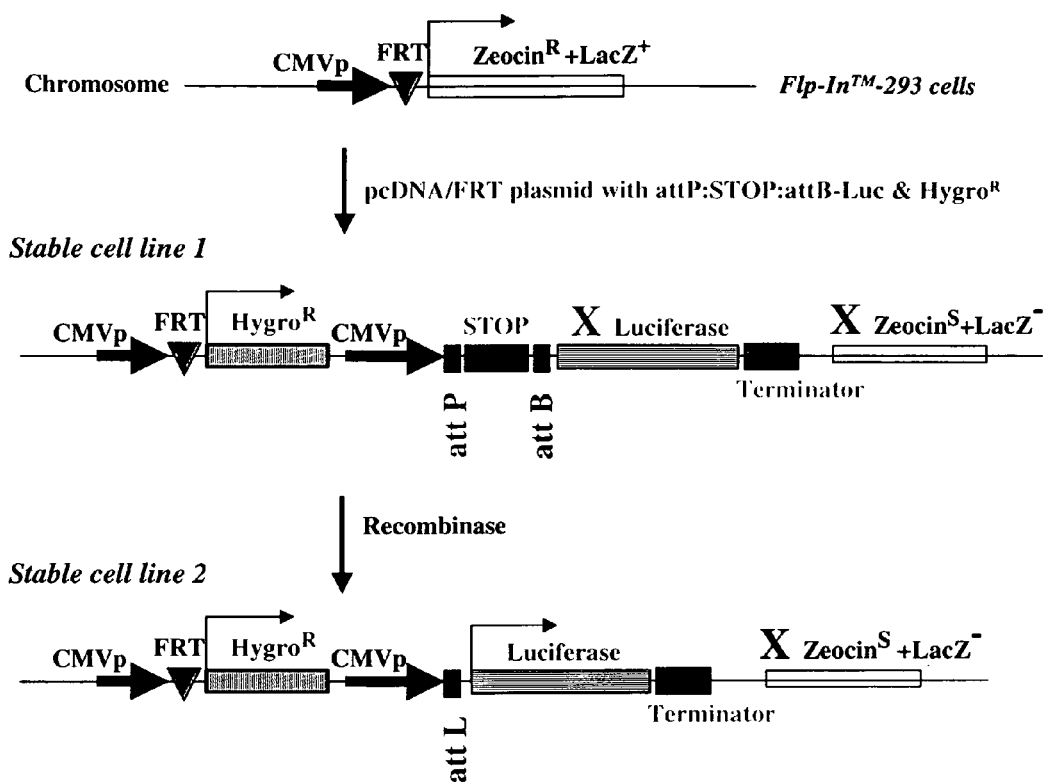
FIG. 11 depicts a schematic representation of excision of stably integrated STOP sequence and activation of luciferase activity due to recombinase.

Luciferase gene—Terminator along with Flp expression plasmid (pCG44, Invitrogen, Carlsbad, Calif.). Clones resistant to hygromycin were selected and expanded (FIG. 11). The insertion of pCDNA/FRT plasmid was also confirmed by assaying the selected clones for β-galactosidase activity. The selected clones lost the β-galactosidase activity. The isolated clones were used for transfection with recombinase expression plasmids.

Deletion of STOP Sequence from the Chromosome and Activation of Luciferase in Stable Cell Lines In the second step, hygromycin resistant cells containing the CMV promoter—attP:STOP:attB—Luciferase gene—Terminator construct for each recombinase were transiently transfected with the corresponding recombinase expression plasmid. Cells (15000 per well, 96-well format) were transfected with 0, 25, 50, 100, or 200 ng of recombinase expression plasmids and incubated for 24 hours. Cells were lysed with 50 µl of passive lysis buffer and 25 µl extracts were assayed. Sixteen replicate assays were performed, and luciferase activity (mean of relative light unit)±SE were plotted.

Figure 12:
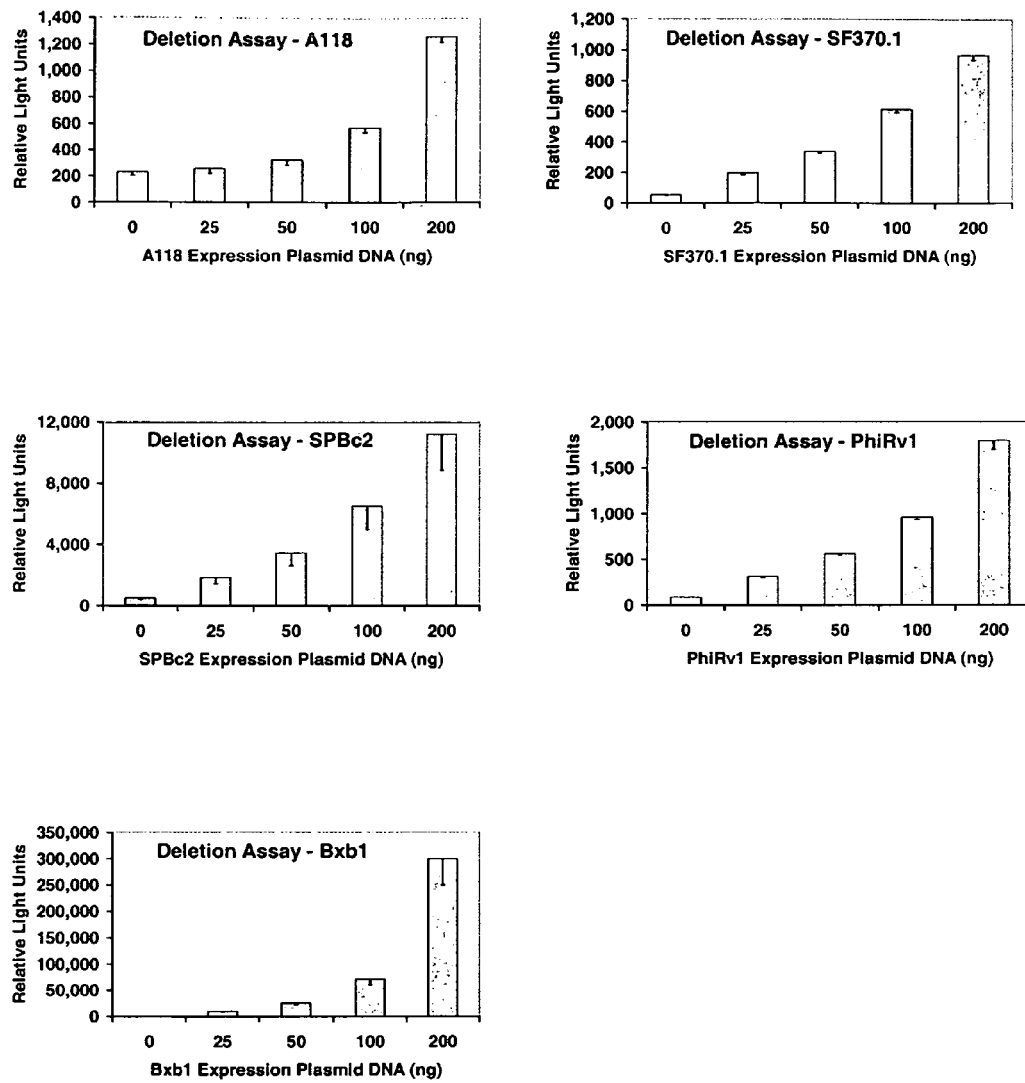
FIG. 12 demonstrates the results of excision of stably integrated STOP sequence and activation of luciferase activity due to recombinase.

As shown in FIG. 12, transfection of increased amounts (0, 25, 50, 100, or 200 ng) of each recombinase expression plasmid into its corresponding attP:STOP:attB containing Flp-In™-293 clone increased the luciferase activity. These results showed that the recombinases can recombine chromosomally placed attP and attB sequences. The recombination resulted in the deletion of sequence flanked by attP and attB sites and activation of luciferase gene.

Example 5

Integration of DNA at Chromosomal Pseudo Attachment Sites in HEK293 Cells

Figure 13:
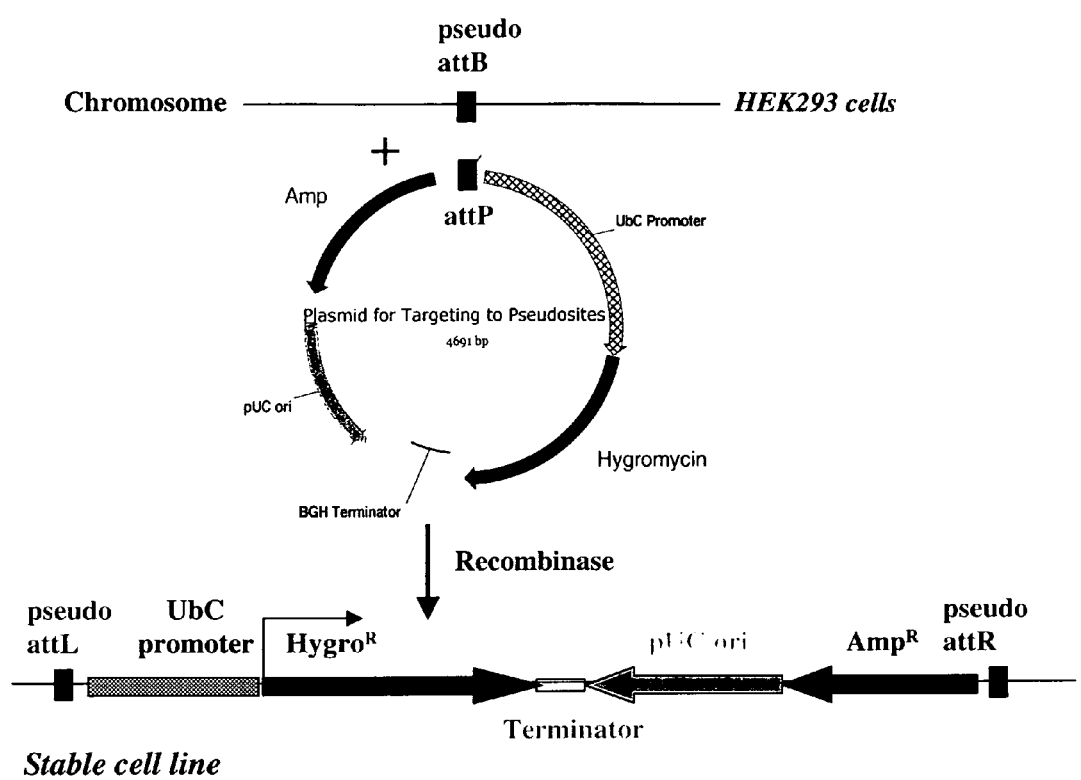
FIG. 13 depicts a schematic representation of insertion or integration of a plasmid containing attP or attB recombination site at the native pseudo attB or pseudo attP site present in HEK293 cells.

Assay for the insertion or integration of a plasmid containing attP or attB recombination site at the native pseudo attB or pseudo attP site present in the HEK293 cell was done by co-transfecting cells with the recombinase expression plasmid and corresponding targeting plasmid containing the attP or attB site and hygromycin resistance gene, and selecting stable cells on media containing hygromycin antibiotic. The procedure is schematically depicted in FIG. 13. HEK293 cells were maintained at 37° C. and 5% $CO_2$ in DMEM supplemented with 10% fetal bovine serum and 1% penicillin/streptomycin (obtained from Invitrogen, Carlsbad, Calif.). On the day of transfection, cells were plated at a density of 750,000 cells per 35 mm Petri dish. The cells were transfected with 50 ng of targeting plasmid containing attP or attB site and a Ubiquitin C promoter-driven hygromycin resistance gene (FIG. 13) alone or along with 4 µg of recombinase expression plasmid using Lipofectamine 2000 according to the manufacturers instructions (Invitrogen, Carlsbad, Calif.). The chromosomal integration of plasmid will result in expression of hygromycin gene and growth of such cells in the presence of hygromycin antibiotic. It should be noted that random integration of targeting plasmid (i.e., at non-pseudo sites) could also result in generation of hygromycin resistant clones. However, when the target plasmid is introduced into cells along with the recombinase expression plasmid, the number of hygromycin resistant HEK293 clones is expected to be higher if the genome contains pseudo attachment sites. Also, for instance, if the integration is due to recombination between pseudo attB site on the genome and attP site on the targeting plasmid the attP site on the targeting plasmid is precisely cut and plasmid is inserted at the pseudo attB sites in the genome, resulting in creation of pseudo attL and pseudo attR sites that can be identified by DNA sequencing of rescued plasmids. In contrast, random integrations generally preserve the intact attP site after integration.

The hygromycin resistant HEK293 clones obtained in the presence of recombinase expression plasmid were pooled, genomic DNA preparation was made and digested with restriction enzymes that cut out side the integrated plasmid (i.e., outside the region of pUC ori and bacterial selectable marker gene), the digested DNA was self-ligated, and the ligated DNA was transformed into E. coli to rescue the integrated plasmid containing the adjacent genomic DNA, following the procedures common in this field (Thyagarajan, B. et al. (2001) Site-specific genomic integration in mammalian cells mediated by phage ΦC31 integrase. Mol. Cell. Biol. 21: 3926-3934). Genomic DNA prepared from hygromycin resistant clones (10 µg) was digested with restriction enzymes Bgl II, Xba 1, Eco 01091, Ban II, Sty I, Bso BI, or Btg I in 40 µL total volume for 3 hrs @ 37° C. 20 µL of each digestion was ligated in 200 µL total volume overnight at 4° C., and then purified. The ligated DNA was introduced into E. coli by electroporation and ampicillin-resistant E. coli colonies were then selected on a plate containing the antibiotic. Plasmid DNAs was prepared from the bacterial colonies and the rescued plasmid DNAs were then sequenced. The recovered genomic DNA sequence was used to identify its chromosomal location by aligning the recovered genomic sequence with the human genome sequence at Genbank, NIH Library of Medicine using the BLAST program (http://www.ncbi.nlm.nih.gov/BLAST).

When the pseudo site targeting plasmid containing the attP site of SF370.1 or SPβc2 recombinase was introduced into HEK293 cells, 9 and 0 hygromycin resistant clones were obtained, respectively (Table 3). In contrast, when the targeting plasmid DNA was co-introduced into HEK293 cells along with respective SF370.1 or SPβc2 recombinase expression plasmid, more than 100 hygromycin resistant clones were recovered in each case (Table 3). These results clearly indicate that recombinase-mediated integration at chromosomal pseudo attB sites was highly efficient and integration at pseudo sites was many fold higher than random integration of targeting plasmid (i.e., integration in the absence of recombinase). Genomic DNA was isolated from pooled hygromycin-resistant HEK293 clones obtained with SF370.1 recombinase, plasmids were rescued from the genome, and pseudo attB sequences were identified by sequencing 100 plasmid DNAs as described above. Out of the 100 rescued plasmids sequenced; there were 41 different pseudo attB sites, as there were more integrations at some pseudo sites than at other pseudo sites. For example, 35 out 100 recovered integrations were at a single site. The nucleotide sequence of this pseudo attB site is given in FIG. 14. These results suggest that the SF370.1 recombinase preferentially integrated plasmid DNA at this site compared to other sites.

TABLE 3

| Integration of attP containing plasmid into HEK293 chromosomal pseudo attB sites | | | | |
|---|---|---|---|---|
| | | Site on | Number of hygromycin[R] clones | |
| Recombinase | Chromosomal pseudo site | targeting plasmid | Without Recombinase | With Recombinase |
| SF370.1 | attB | attP | 9 | >100 |
| SPβc2 | attB | attP | 0 | >100 |

Similar analysis was done with hygromycin resistant HEK293 clones obtained after targeting of SPβc2 attP containing plasmid using the SPβc2 recombinase and 109 rescued plasmids DNAs were sequenced. Sequence analysis showed that 105 out of 107 integrations were at pseudo attB sites and 2 integrations were at random sites. There were 54 different pseudo attB integration sites among the 105 integration sites recovered. Fifteen of the integrations occurred at one pseudo site sequence shown in FIG. 14. These results show that human and eukaryotic chromosomes serve as efficient targets for precise site-specific integrations at pseudo att sites using the enzymes we discovered. These sites form naturally occurring targets for integration that can be used in many biotechnology and medical applications.

What is claimed is:

1. A method for obtaining site-specific recombination in a eukaryotic cell, the method comprising:
providing a eukaryotic cell that comprises a first recombination site and a second recombination site;
contacting the first and second recombination sites with a prokaryotic serine recombinase polypeptide, resulting in recombination between the recombination sites,
wherein the serine recombinase polypeptide can mediate recombination between the first and second recombination sites, the first recombination site is a phage genomic recombination attachment site (attP) or a bacterial genomic recombination attachment site (attB),
the second recombination site is attB or attP, and
the serine recombinase is a *Streptococcus pyogenes* SF370.1 phage serine recombinase,
provided that when the first recombination attachment site is attB, the second recombination attachment site is attP, and when the first recombination attachment site is attP, the second recombination attachment site is attB.

2. A method for obtaining site-specific recombination in a eukaryotic cell, the method comprising:
providing a eukaryotic cell that comprises a first recombination site and a second recombination site;
contacting the first and second recombination sites with a prokaryotic serine recombinase polypeptide, resulting in recombination between the recombination sites,
wherein the serine recombinase polypeptide can mediate recombination between the first and second recombination sites,
the first recombination site is attP or attB,
the second recombination site is a pseudo attachment site, and
the serine recombinase is a *Streptococcus pyogenes* SF370.1 phage serine recombinase.

3. The method of claim 1 or 2, wherein the serine recombinase polypeptide is encoded by a polynucleotide operably linked to a promoter which mediates expression of the polynucleotide in the eukaryotic cell.

4. The method of claim 1 or 2, wherein the serine recombinase polypeptide is introduced into the eukaryotic cell by expression of a polynucleotide that encodes the serine recombinase polypeptide.

5. The method of claim 1 or 2, wherein the serine recombinase polypeptide is introduced into the eukaryotic cell as a polypeptide.

6. The method of claim 1 or 2, wherein the serine recombinase polypeptide is introduced into the eukaryotic cell by messenger RNA that encodes the serine recombinase polypeptide.

7. The method of claim 1 or 2, wherein the site-specific recombination results in integration, deletion, inversion, translocation or exchange of DNA.

8. A method for obtaining a eukaryotic cell having a stably integrated polynucleotide sequence, the method comprising:
providing a eukaryotic cell that comprises a first recombination attB or attP site,
introducing a polynucleotide into the eukaryotic cell, wherein the polynucleotide comprises a nucleic acid sequence and a second recombination attP or attB site, and
contacting the first and the second recombination sites with a prokaryotic serine recombinase polypeptide,
wherein the serine recombinase polypeptide can mediate site-specific recombination between the first and second recombination sites, and
the serine recombinase is a *Streptococcus pyogenes* SF370.1 phage serine recombinase,
provided that when the first recombination site is attB, the second recombination site is attP and when the first recombination site is attP, the second recombination site is attB.

9. A method for obtaining a eukaryotic cell having a stably integrated polynucleotide sequence, the method comprising:
providing a eukaryotic cell that comprises a first recombination pseudo attachment site,
introducing a polynucleotide into the eukaryotic cell, wherein the polynucleotide comprises a nucleic acid sequence and a second recombination attP or attB site, and
contacting the first and the second recombination sites with a prokaryotic serine recombinase polypeptide, wherein the serine recombinase polypeptide can mediate site-specific recombination between the first and second recombination sites, and
the serine recombinase is a *Streptococcus pyogenes* SF370.1 phage serine recombinase.

10. The method of claim 8 or 9, wherein the serine recombinase polypeptide is encoded by a polynucleotide operably linked to a promoter which mediates expression of the polynucleotide in the eukaryotic cell.

11. The method of claim 8 or 9, wherein the serine recombinase polypeptide is introduced into the eukaryotic cell by expression of a polynucleotide that encodes the serine recombinase polypeptide.

12. The method of claim 8 or 9, wherein the serine recombinase polypeptide is introduced into the eukaryotic cell as a polypeptide.

13. The method of claim 8 or 9, wherein the serine recombinase polypeptide is introduced into the eukaryotic cell by expression of RNA that encodes the serine recombinase polypeptide.

14. A method for obtaining site-specific recombination in a eukaryotic cell, the method comprising:
   providing a eukaryotic cell that comprises a first recombination site and a second recombination site with a polynucleotide sequence flanked by a third recombination site and a fourth recombination site;
   contacting the recombination sites with a prokaryotic serine recombinase polypeptide, resulting in recombination between the recombination sites,
   wherein the serine recombinase polypeptide can mediate recombination between the first and third recombination sites and the second and fourth recombination sites,
   the first and second recombination sites are attP or attB, the third and fourth recombination sites are attB or attP, and
   the serine recombinase is a *Streptococcus pyogenes* SF370.1 phage serine recombinase,
   provided that when the first and second recombination attachment sites are attB, the third and fourth recombination attachment sites are attP, and when the first and second recombination attachment sites are attP, the third and fourth recombination attachment sites are attB.

15. The method of claim 14, wherein the serine recombinase polypeptide is introduced into the eukaryotic cell by expression of a polynucleotide that encodes the serine recombinase polypeptide.

16. The method of claim 14, wherein the serine recombinase polypeptide is introduced into the eukaryotic cell as a polypeptide.

17. The method of claim 14, wherein the serine recombinase polypeptide is introduced into the eukaryotic cell by messenger RNA that encodes the serine recombinase polypeptide.

18. A method for site-specific recombination, the method comprising:
   providing a first recombination site and a second recombination site;
   contacting the first and second recombination sites with a prokaryotic serine recombinase polypeptide, resulting in recombination between the recombination sites,
   wherein the serine recombinase polypeptide can mediate recombination between the first and second recombination sites,
   the first recombination site is attP or attB, the second recombination site is attB or attP, and
   the serine recombinase is a *Streptococcus pyogenes* SF370.1 phage serine recombinase,
   provided that when the first recombination attachment site is attB, the second recombination attachment site is attP, and when the first recombination attachment site is attP, the second recombination attachment site is attB.

19. A method for the site-specific integration of a polynucleotide of interest into the genome of a transgenic subject,
   wherein said genome comprises a first recombination attB or attP site or pseudo attB or pseudo attP site,
   the method comprising:
   introducing a nucleic acid that comprises the polynucleotide of interest and a second recombination attP or attB site;
   contacting the first and the second recombination sites with a prokaryotic serine recombinase polypeptide,
   wherein the serine recombinase polypeptide can mediate site-specific recombination between the first and second recombination sites, and
   the serine recombinase is a *Streptococcus pyogenes* SF370.1 phage serine recombinase,
   provided that when the first recombination site is attB or pseudo attB, the second recombination site is attP and when the first recombination site is attP or pseudo attP, the second recombination site is attB.

20. The method of claim 8, wherein the first attB or attP site is located in the chromosome of the eukaryotic cell.

21. The method of claim 9, wherein the first recombination pseudo attachment site is located in the chromosome of the eukaryotic cell.

22. The method of claim 1 or claim 2, wherein the site-specific recombination is irreversible.

23. The method of any one of claims 14 and 18 wherein the site specific recombination is irreversible.

24. The method of claim 19, wherein the site-specific integration is irreversible.

* * * * *

```
                              SEQUENCE LISTING

<160> NUMBER OF SEQ ID NOS: 28

<210> SEQ ID NO 1
<211> LENGTH: 1638
<212> TYPE: DNA
<213> ORGANISM: Artificial Sequence
<220> FEATURE:
<223> OTHER INFORMATION: synthetic gene

<400> SEQUENCE: 1
atggaactga agaacatcgt gaacagctac aacatcacca acatcctggg ctacctgcgg      60
agaagcaggc aggacatgga gagagagaag cggaccggcg aggacaccct caccgagcag     120
aaggaactca tgaacaagat cctcaccgcc atcgagatcc cctacgagct gaagatggag     180
atcggcagcg gcgagagcat cgacggcaga cccgtgttca aggagtgcct gaaggatctg     240
gaggagggca agtaccaggc catcgccgtg aaggagatca ccaggctgag cagaggcagc     300
tacagcgacg ccggccagat cgtgaacctg ctgcagagca gcggctcat catcatcacc     360 ccctacaagg tgtacgaccc cagaaacccc gtcgacatgc ggcagatccg gttcgagctg     420
ttcatggcca gggaggagtt cgagatgacc cgggagagaa tgaccggcgc caagtacacc     480
tacgccgccc agggcaagtg gatcagcggc ctggccccct acggctacca gctgaacaag     540
aaaaccagca agctggaccc cgtggaggac gaggccaagg tggtgcagct catcttcaac     600
atcttcctga acgggctgaa cggcaaggac tacagctaca cagccatcgc cagccacctc     660
accaatctgc agatccctac ccccagcggc aagaagcggt ggaaccagta caccatcaag     720
gccatcctgc agaacgaggt gtacatcggc accgtgaagt acaaggtgcg ggagaaaacc     780
aaggacggca agcggaccat caggcctgag aaggagcaga tcgtggtgca ggacgcccac     840
gcccctatca tcgacaagga gcagttccag cagagccagg tgaagatcgc caacaaggtg     900
cccctgctgc ccaacaagga cgagttcgag ctgagcgagc tggccggagt gtgcacctgc     960
agcaagtgcg gcgagcctct gagcaagtac gagagcaagc gcatccggaa gaacaaggat    1020
ggcaccgaga gcgtgtacca cgtgaagtcc ctcacctgca gaagaacaa gtgcacctac    1080 gtgcggtaca acgacgtgga gaacgccatc ctggattacc tgagcagcct gaacgacctg    1140
aatgacagca ccctcacaaa gcacatcaac agcatgctct ccaagtacga ggacgacaac    1200
agcaacatga aaaccaagaa gcagatgagc gagcacctga ccagaagga aaggagctt    1260 aagaataagg agaacttcat cttcgacaag tacgagtccg gcatctactc cgacgagctg    1320
ttcctgaagc ggaaggccgc cctggacgag gagttcaagg agctgcagaa cgccaagaac    1380
gagctgaatg gcctgcagga tacccagagc gagatcgaca gcaacaccgt gcggaacaac    1440
atcaacaaga tcatcgacca gtaccacatc gagagcagca gcgagaagaa gaatgagctg    1500
ctgcggatgg tgctgaagga cgtgatcgtg aacatgaccc agaagcgcaa gggcccatc    1560 cccgcccagt tcgagatcac acccatcctg cggttcaact ttatcttcga tctcaccgcc    1620
accaacagct ccactag                                                    1638
```

```
<210> SEQ ID NO 2
<211> LENGTH: 545
<212> TYPE: PRT
<213> ORGANISM: Bacillus subtilis phage SPBc2

<400> SEQUENCE: 2

Met Glu Leu Lys Asn Ile Val Asn Ser Tyr Asn Ile Thr Asn Ile Leu
1               5                   10                  15

Gly Tyr Leu Arg Arg Ser Arg Gln Asp Met Glu Arg Glu Lys Arg Thr
            20                  25                  30

Gly Glu Asp Thr Leu Thr Glu Gln Lys Glu Leu Met Asn Lys Ile Leu
        35                  40                  45

Thr Ala Ile Glu Ile Pro Tyr Glu Leu Lys Met Glu Ile Gly Ser Gly
    50                  55                  60

Glu Ser Ile Asp Gly Arg Pro Val Phe Lys Glu Cys Leu Lys Asp Leu
65                  70                  75                  80

Glu Glu Gly Lys Tyr Gln Ala Ile Ala Val Lys Glu Ile Thr Arg Leu
                85                  90                  95

Ser Arg Gly Ser Tyr Ser Asp Ala Gly Gln Ile Val Asn Leu Leu Gln
            100                 105                 110

Ser Lys Arg Leu Ile Ile Ile Thr Pro Tyr Lys Val Tyr Asp Pro Arg
        115                 120                 125

Asn Pro Val Asp Met Arg Gln Ile Arg Phe Glu Leu Phe Met Ala Arg
    130                 135                 140

Glu Glu Phe Glu Met Thr Arg Glu Arg Met Thr Gly Ala Lys Tyr Thr
145                 150                 155                 160

Tyr Ala Ala Gln Gly Lys Trp Ile Ser Gly Leu Ala Pro Tyr Gly Tyr
                165                 170                 175

Gln Leu Asn Lys Lys Thr Ser Lys Leu Asp Pro Val Glu Asp Glu Ala
            180                 185                 190

Lys Val Val Gln Leu Ile Phe Asn Ile Phe Leu Asn Gly Leu Asn Gly
        195                 200                 205

Lys Asp Tyr Ser Tyr Thr Ala Ile Ala Ser His Leu Thr Asn Leu Gln
    210                 215                 220

Ile Pro Thr Pro Ser Gly Lys Lys Arg Trp Asn Gln Tyr Thr Ile Lys
225                 230                 235                 240

Ala Ile Leu Gln Asn Glu Val Tyr Ile Gly Thr Val Lys Tyr Lys Val
                245                 250                 255

Arg Glu Lys Thr Lys Asp Gly Lys Arg Thr Ile Arg Pro Glu Lys Glu
            260                 265                 270

Gln Ile Val Val Asp Ala His Ala Pro Ile Ile Asp Lys Glu Gln
        275                 280                 285

Phe Gln Gln Ser Gln Val Lys Ile Ala Asn Lys Val Pro Leu Leu Pro
    290                 295                 300

Asn Lys Asp Glu Phe Glu Leu Ser Glu Leu Ala Gly Val Cys Thr Cys
305                 310                 315                 320

Ser Lys Cys Gly Glu Pro Leu Ser Lys Tyr Glu Ser Lys Arg Ile Arg
                325                 330                 335

Lys Asn Lys Asp Gly Thr Glu Ser Val Tyr His Val Lys Ser Leu Thr
            340                 345                 350

Cys Lys Lys Asn Lys Cys Thr Tyr Val Arg Tyr Asn Asp Val Glu Asn
        355                 360                 365

Ala Ile Leu Asp Tyr Leu Ser Ser Leu Asn Asp Leu Asn Asp Ser Thr
    370                 375                 380
```

| | | | | | | | | | | | | | | |
|---|---|---|---|---|---|---|---|---|---|---|---|---|---|---|
|Leu|Thr|Lys|His|Ile|Asn|Ser|Met|Leu|Ser|Lys|Tyr|Glu|Asp|Asp|Asn|
|385| | | |390| | | |395| | | |400|

Ser Asn Met Lys Thr Lys Lys Gln Met Ser Glu His Leu Ser Gln Lys
               405                   410               415

Glu Lys Glu Leu Lys Asn Lys Glu Asn Phe Ile Phe Asp Lys Tyr Glu
        420                   425                 430

Ser Gly Ile Tyr Ser Asp Glu Leu Phe Leu Lys Arg Lys Ala Ala Leu
           435                 440               445

Asp Glu Glu Phe Lys Glu Leu Gln Asn Ala Lys Asn Glu Leu Asn Gly
450                 455                 460

Leu Gln Asp Thr Gln Ser Glu Ile Asp Ser Asn Thr Val Arg Asn Asn
465               470                 475               480

Ile Asn Lys Ile Ile Asp Gln Tyr His Ile Glu Ser Ser Ser Glu Lys
           485                 490               495

Lys Asn Glu Leu Leu Arg Met Val Leu Lys Asp Val Ile Val Asn Met
        500                 505                 510

Thr Gln Lys Arg Lys Gly Pro Ile Pro Ala Gln Phe Glu Ile Thr Pro
           515                 520               525

Ile Leu Arg Phe Asn Phe Ile Phe Asp Leu Thr Ala Thr Asn Ser Phe
530                 535                 540

His
545

<210> SEQ ID NO 3
<211> LENGTH: 1416
<212> TYPE: DNA
<213> ORGANISM: Artificial Sequence
<220> FEATURE:
<223> OTHER INFORMATION: Synthetic gene

<400> SEQUENCE: 3

```
atgcggaagg tggccatcta cagcagggtg agcaccatca atcaggccga ggagggctac      60
agcatccagg ccagatcga ggccctcacc aagtactgcg aggccatgga gtggaagatc     120
tacaagaact acagcgacgc cggcttcagc ggcggcaagc tggagagacc cgccatcacc     180
gagttgatcg aggacggcaa gaacaacaag ttcgacacca tcctggtgta caagctggac     240
cggctgagca gaaacgtgaa ggacacccct tacctggtga aggacgtgtt caccgccaac     300
aacatcccac tcgtgagcct gaaggagaac atcgacacca gcagcgccat gggcaatctg     360
ttcctcacac tgctgagcgc aattgccgag ttcgagcggg agcagatcaa ggaacggatg     420
cagttcggcg tgatgaacag agccaagagc ggcaagacca ccgcctggaa aacccctcca     480
tacggctacc ggtacaacaa ggacgagaaa accctgagcg tgaacgagct ggaggccgcc     540
aatgtgaggc agatgttcga catgatcatc agcggctgca gcatcatgag catcaccaac     600
tacgcccggg acaacttcgt gggcaacacc tggacccacg tgaaggtgaa gcggatcctg     660
gagaacgaga cctacaaagg cctggtgaag taccggagc agacctttag cggcgatcac     720
caggccatca tcgacgaaaa gacctacaac aaggcccaga tcgccctggc ccacagaacc     780
gacaccaaga ccaacaccag accctccag ggcaagtaca tgctgagcca catcgccaag     840
tgcggctact gtggcgcccc tctgaaggtg tgcaccggca gggccaagaa tgacggcacc     900
cggagacaga cctacgtgtg cgtgaacaag accgagagcc tggcagaag agcgtgaac     960
aactacaaca accagaagat ctgcaacacc ggccggtacg agaagaagca catcgagaag    1020
tacgtgatcg acgtgctgta taagctgcag cacgacaagg agtacctgaa gaagatcaag    1080
```

```
aaggacgaca acatcatcga tatcacccc ctgaagaagg agatcgagat catcgacaag    1140
aagattaacc ggctgaacga cctgtacatc aacgacctca tcgacctgcc caagctgaag    1200
aaagacatcg aggagctgaa ccacctgaag gacgactaca ataaggccat caagctgaac    1260
tacctggaca agaagaacga ggacagcctg ggcatgctca tggacaacct ggacatccgc    1320
aagagcagct acgacgtgca gagccggatc gtgaagcagc tcatcgacag ggtggaggtg    1380
accatggaca atatcgacat catcttcaag ttctag                              1416

<210> SEQ ID NO 4
<211> LENGTH: 471
<212> TYPE: PRT
<213> ORGANISM: Putative recombinase of bacteriophage SF370.1

<400> SEQUENCE: 4

Met Arg Lys Val Ala Ile Tyr Ser Arg Val Ser Thr Ile Asn Gln Ala
1               5                   10                  15

Glu Glu Gly Tyr Ser Ile Gln Gly Gln Ile Glu Ala Leu Thr Lys Tyr
            20                  25                  30

Cys Glu Ala Met Glu Trp Lys Ile Tyr Lys Asn Tyr Ser Asp Ala Gly
        35                  40                  45

Phe Ser Gly Gly Lys Leu Glu Arg Pro Ala Ile Thr Glu Leu Ile Glu
    50                  55                  60

Asp Gly Lys Asn Lys Phe Asp Thr Ile Leu Val Tyr Lys Leu Asp
65                  70                  75                  80

Arg Leu Ser Arg Asn Val Lys Asp Thr Leu Tyr Leu Val Lys Asp Val
                85                  90                  95

Phe Thr Ala Asn Asn Ile His Phe Val Ser Leu Lys Glu Asn Ile Asp
            100                 105                 110

Thr Ser Ser Ala Met Gly Asn Leu Phe Leu Thr Leu Ser Ala Ile
            115                 120                 125

Ala Glu Phe Glu Arg Glu Gln Ile Lys Glu Arg Met Gln Phe Gly Val
        130                 135                 140

Met Asn Arg Ala Lys Ser Gly Lys Thr Thr Ala Trp Lys Thr Pro Pro
145                 150                 155                 160

Tyr Gly Tyr Arg Tyr Asn Lys Asp Glu Lys Thr Leu Ser Val Asn Glu
                165                 170                 175

Leu Glu Ala Ala Asn Val Arg Gln Met Phe Asp Met Ile Ile Ser Gly
            180                 185                 190

Cys Ser Ile Met Ser Ile Thr Asn Tyr Ala Arg Asp Asn Phe Val Gly
        195                 200                 205

Asn Thr Trp Thr His Val Lys Val Lys Arg Ile Leu Glu Asn Glu Thr
    210                 215                 220

Tyr Lys Gly Leu Val Lys Tyr Arg Glu Gln Thr Phe Ser Gly Asp His
225                 230                 235                 240

Gln Ala Ile Ile Asp Glu Lys Thr Tyr Asn Lys Ala Gln Ile Ala Leu
                245                 250                 255

Ala His Arg Thr Asp Thr Lys Thr Asn Thr Arg Pro Phe Gln Gly Lys
            260                 265                 270

Tyr Met Leu Ser His Ile Ala Lys Cys Gly Tyr Cys Gly Ala Pro Leu
        275                 280                 285

Lys Val Cys Thr Gly Arg Ala Lys Asn Asp Gly Thr Arg Arg Gln Thr
    290                 295                 300

Tyr Val Cys Val Asn Lys Thr Glu Ser Leu Ala Arg Arg Ser Val Asn
305                 310                 315                 320
```

Asn Tyr Asn Asn Gln Lys Ile Cys Asn Thr Gly Arg Tyr Glu Lys Lys
                325                 330                 335

His Ile Glu Lys Tyr Val Ile Asp Val Leu Tyr Lys Leu Gln His Asp
            340                 345                 350

Lys Glu Tyr Leu Lys Lys Ile Lys Lys Asp Asn Ile Ile Asp Ile
        355                 360                 365

Thr Pro Leu Lys Lys Glu Ile Glu Ile Ile Asp Lys Lys Ile Asn Arg
    370                 375                 380

Leu Asn Asp Leu Tyr Ile Asn Asp Leu Ile Asp Leu Pro Lys Leu Lys
385                 390                 395                 400

Lys Asp Ile Glu Glu Leu Asn His Leu Lys Asp Tyr Asn Lys Ala
            405                 410                 415

Ile Lys Leu Asn Tyr Leu Asp Lys Lys Asn Glu Asp Ser Leu Gly Met
                420                 425                 430

Leu Met Asp Asn Leu Asp Ile Arg Lys Ser Ser Tyr Asp Val Gln Ser
        435                 440                 445

Arg Ile Val Lys Gln Leu Ile Asp Arg Val Glu Val Thr Met Asp Asn
    450                 455                 460

Ile Asp Ile Ile Phe Lys Phe
465                 470

<210> SEQ ID NO 5
<211> LENGTH: 1503
<212> TYPE: DNA
<213> ORGANISM: Artificial Sequence
<220> FEATURE:
<223> OTHER INFORMATION: Synthetic gene

<400> SEQUENCE: 5
atgcgggctc tggtggtgat caggctgagc agagtgaccg atgccaccac aagccctgag      60
agacagctgg agagctgcca gcagctgtgt gcccagagag gatgggacgt ggtgggagtg     120
gccgaggatc tggatgtgag cggagccgtg accccttcg acagaaagcg agacccaac      180 ctggccagat ggctggcctt tgaggagcag cccttcgatg tgatcgtggc ctacagagtg     240
gacaggctga cccggagcat agacacctc agcagctggt gcactgggc cgaggaccac      300 aagaaactgg tggtgagcgc cacagaggcc cacttcgata ccaccacccc ctttgctgca     360
gtggtgatcg ccctgatggg cacagtggcc cagatggagc tggaggccat caaggagagg     420
aatcggtctg ccgcccactt caatatcagg gccggcaagt acagaggaag cctgcctcct     480
tggggctacc tgcccacaag agtggatggc gagtggagac tggtgcctga ccctgtgcag     540
agggagagaa tcctggaagt gtatcaccgc gtggtggaca tcacgagcc tctgcacctg     600 gtggcccacg acctgaatag agagggcgtg ctgtcccca aggattactt cgcccagctc     660
cagggcagag agcctcaggg cagagagtgg tctgccaccg ccctgaaaag atctatgatc     720
agcgaggcca tgctgggcta cgccaccctg aatggcaaga ccgtgaggga tgatgatgga     780
gccctctggt gagagccga gccatcctg acaagggaac agctggaggc tctgagagcc      840
gaactggtga aaaccagcag agccaagcct gccgtgagca cacctagcct gctgctgaga     900
gtgctgttct gtgccgtgtg tggcgagcct gcctacaagt tgccggcgg aggcagaaag     960 caccccgggt acagatgtag gagcatgggc ttccctaagc actgcggcaa tggcaccgtg    1020
gccatggccg aatgggacgc cttttgcgag gagcaagtgc tggatctgct gggagatgcc    1080
gagaggctgg agaaagtgtg ggtggccgga tccgattctg ccgtgaact ggccgaagtg    1140

-continued

```
aatgctgaac tggtggacct gaccagcctg atcggcagcc ctgcctatag agccggaagc    1200
cctcagagag aagccctgga cgccagaatt gccgccctgg ccgccagaca ggaggaactg    1260
gagggactgg aggccagacc ttctggctgg gagtggagag agaccggcca gagattcggc    1320
gattggtgga gggagcagga taccgccgcc aagaacacct ggctgcggag catgaacgtg    1380
aggctgacct tcgacgtgag aggcggcctg accagaacca tcgacttcgg cgacctccag    1440
gagtatgagc agcacctgag actgggaagc gtggtggaga gactgcacac aggcatgtcc    1500
tag                                                                  1503
```

<210> SEQ ID NO 6
<211> LENGTH: 500
<212> TYPE: PRT
<213> ORGANISM: Putative recombinase of mycobacteriophage Bxb1

<400> SEQUENCE: 6

```
Met Arg Ala Leu Val Val Ile Arg Leu Ser Arg Val Thr Asp Ala Thr
1               5                   10                  15

Thr Ser Pro Glu Arg Gln Leu Glu Ser Cys Gln Gln Leu Cys Ala Gln
                20                  25                  30

Arg Gly Trp Asp Val Val Gly Val Ala Glu Asp Leu Asp Val Ser Gly
            35                  40                  45

Ala Val Asp Pro Phe Asp Arg Lys Arg Arg Pro Asn Leu Ala Arg Trp
        50                  55                  60

Leu Ala Phe Glu Glu Gln Pro Phe Asp Val Ile Val Ala Tyr Arg Val
65                  70                  75                  80

Asp Arg Leu Thr Arg Ser Ile Arg His Leu Gln Gln Leu Val His Trp
                85                  90                  95

Ala Glu Asp His Lys Lys Leu Val Val Ser Ala Thr Glu Ala His Phe
            100                 105                 110

Asp Thr Thr Thr Pro Phe Ala Ala Val Val Ile Ala Leu Met Gly Thr
        115                 120                 125

Val Ala Gln Met Glu Leu Glu Ala Ile Lys Glu Arg Asn Arg Ser Ala
    130                 135                 140

Ala His Phe Asn Ile Arg Ala Gly Lys Tyr Arg Gly Ser Leu Pro Pro
145                 150                 155                 160

Trp Gly Tyr Leu Pro Thr Arg Val Asp Gly Glu Trp Arg Leu Val Pro
                165                 170                 175

Asp Pro Val Gln Arg Glu Arg Ile Leu Glu Val Tyr His Arg Val Val
            180                 185                 190

Asp Asn His Glu Pro Leu His Leu Val Ala His Asp Leu Asn Arg Arg
        195                 200                 205

Gly Val Leu Ser Pro Lys Asp Tyr Phe Ala Gln Leu Gln Gly Arg Glu
    210                 215                 220

Pro Gln Gly Arg Glu Trp Ser Ala Thr Ala Leu Lys Arg Ser Met Ile
225                 230                 235                 240

Ser Glu Ala Met Leu Gly Tyr Ala Thr Leu Asn Gly Lys Thr Val Arg
                245                 250                 255

Asp Asp Asp Gly Ala Pro Leu Val Arg Ala Glu Pro Ile Leu Thr Arg
            260                 265                 270

Glu Gln Leu Glu Ala Leu Arg Ala Glu Leu Val Lys Thr Ser Arg Ala
        275                 280                 285

Lys Pro Ala Val Ser Thr Pro Ser Leu Leu Leu Arg Val Leu Phe Cys
    290                 295                 300
```

```
Ala Val Cys Gly Glu Pro Ala Tyr Lys Phe Ala Gly Gly Arg Lys
305                 310                 315                 320

His Pro Arg Tyr Arg Cys Arg Ser Met Gly Phe Pro Lys His Cys Gly
                325                 330                 335

Asn Gly Thr Val Ala Met Ala Glu Trp Asp Ala Phe Cys Glu Glu Gln
            340                 345                 350

Val Leu Asp Leu Leu Gly Asp Ala Glu Arg Leu Glu Lys Val Trp Val
        355                 360                 365

Ala Gly Ser Asp Ser Ala Val Glu Leu Ala Glu Val Asn Ala Glu Leu
    370                 375                 380

Val Asp Leu Thr Ser Leu Ile Gly Ser Pro Ala Tyr Arg Ala Gly Ser
385                 390                 395                 400

Pro Gln Arg Glu Ala Leu Asp Ala Arg Ile Ala Ala Leu Ala Ala Arg
                405                 410                 415

Gln Glu Glu Leu Glu Gly Leu Glu Ala Arg Pro Ser Gly Trp Glu Trp
            420                 425                 430

Arg Glu Thr Gly Gln Arg Phe Gly Asp Trp Trp Arg Glu Gln Asp Thr
        435                 440                 445

Ala Ala Lys Asn Thr Trp Leu Arg Ser Met Asn Val Arg Leu Thr Phe
    450                 455                 460

Asp Val Arg Gly Gly Leu Thr Arg Thr Ile Asp Phe Gly Asp Leu Gln
465                 470                 475                 480

Glu Tyr Glu Gln His Leu Arg Leu Gly Ser Val Val Glu Arg Leu His
                485                 490                 495

Thr Gly Met Ser
            500

<210> SEQ ID NO 7
<211> LENGTH: 1359
<212> TYPE: DNA
<213> ORGANISM: Artificial Sequence
<220> FEATURE:
<223> OTHER INFORMATION: Synthetic gene

<400> SEQUENCE: 7
atgaaggccg ccatctacat cagagtgagc acccaggagc aggtggagaa ctacagcatc      60
caggcccaga ccgagaagct cacccgccct gcagaagca aggactggga cgtgtacgac       120
atcttcatcg acggcggcta cagcggcagc aacatgaaca gacccgccct gaacgagatg      180
ctgagcaagc tgcacgagat cgatgccgtg gtggtgtaca ggctggacag gctgagcaga      240
agccagaggg acaccatcac cctcatcgag gagtacttcc tgaagaacaa cgtggagttc      300
gtgagcctga gcgagaccct ggacaccagc agcccttcg gcagagccat gatcggcatc       360
ctgagcgtgt tcgcccagct cgagagagag accatccggg acaggatggt gatgggcaag      420
atcaagagga tcgaggccgg cctgccctc accaccgcca agggcagaac cttcggctac       480
gacgtgatcg acaccaagct gtacatcaac gaggaggagg ccaagcagct gcagctcatc      540
tacgatatct tcgaggagga gcagagcatc accttcctgc agaagcggct gaagaagctg      600
ggcttcaagg tgcggaccta caaccggtac aacaactggc tcaccaacga cctgtactgc      660
ggctacgtga gctacaagga caaggtgcac gtgaagggga tccacgagcc atcatcagc       720 gaggagcagt tctaccgggt gcaggagatc ttcacccgca tgggcaagaa ccccaacatg      780
aaccgggaca cgccagcct gctgaacaat ctggtggtgt gcagcaagtg cggcctgggc       840
ttcgtgcaca ggagaaagga caccatgagc cggggcaaga agtaccacta ccggtactac      900
```

```
agctgcaaga cctacaagca cacccacgag ctggagaagt gcggcaacaa gatctggagg      960
gccgacaagc tggaggagtt gatcatcaac cgggtgaaca actacagctt cgccagccgg     1020
aacgtggata aggaggacga gctggacagc ctgaatgaga agcttaagat cgagcacgcc     1080
aagaagaagc gcctgttcga cctgtacatt aacggcagct acgaggtgag cgagctggac     1140
tccatgatga acgacatcga cgcccagatc aactactacg agagccagat cgaggccaac     1200
gaggagctga agaagaacaa gaagatccag gagaacctgg ccgacctggc caccgtggat     1260
ttcgacagcc tggagttcag ggagaagcag ctgtacctga agtccctcat caataagatc     1320
tacatcgacg gggagcaggt gaccatcgag tggctgtag                            1359
```

<210> SEQ ID NO 8
<211> LENGTH: 452
<212> TYPE: PRT
<213> ORGANISM: Putative recombinase of bacteriophage A118

<400> SEQUENCE: 8

```
Met Lys Ala Ala Ile Tyr Ile Arg Val Ser Thr Gln Glu Gln Val Glu
1               5                   10                  15

Asn Tyr Ser Ile Gln Ala Gln Thr Glu Lys Leu Thr Ala Leu Cys Arg
            20                  25                  30

Ser Lys Asp Trp Asp Val Tyr Asp Ile Phe Ile Asp Gly Gly Tyr Ser
        35                  40                  45

Gly Ser Asn Met Asn Arg Pro Ala Leu Asn Glu Met Leu Ser Lys Leu
    50                  55                  60

His Glu Ile Asp Ala Val Val Val Tyr Arg Leu Asp Arg Leu Ser Arg
65                  70                  75                  80

Ser Gln Arg Asp Thr Ile Thr Leu Ile Glu Glu Tyr Phe Leu Lys Asn
                85                  90                  95

Asn Val Glu Phe Val Ser Leu Ser Glu Thr Leu Asp Thr Ser Ser Pro
            100                 105                 110

Phe Gly Arg Ala Met Ile Gly Ile Leu Ser Val Phe Ala Gln Leu Glu
        115                 120                 125

Arg Glu Thr Ile Arg Asp Arg Met Val Met Gly Lys Ile Lys Arg Ile
130                 135                 140

Glu Ala Gly Leu Pro Leu Thr Thr Ala Lys Gly Arg Thr Phe Gly Tyr
145                 150                 155                 160

Asp Val Ile Asp Thr Lys Leu Tyr Ile Asn Glu Glu Glu Ala Lys Gln
                165                 170                 175

Leu Gln Leu Ile Tyr Asp Ile Phe Glu Glu Gln Ser Ile Thr Phe
            180                 185                 190

Leu Gln Lys Arg Leu Lys Lys Leu Gly Phe Lys Val Arg Thr Tyr Asn
        195                 200                 205

Arg Tyr Asn Asn Trp Leu Thr Asn Asp Leu Tyr Cys Gly Tyr Val Ser
210                 215                 220

Tyr Lys Asp Lys Val His Val Lys Gly Ile His Glu Pro Ile Ile Ser
225                 230                 235                 240

Glu Glu Gln Phe Tyr Arg Val Gln Glu Ile Phe Thr Arg Met Gly Lys
                245                 250                 255

Asn Pro Asn Met Asn Arg Asp Ser Ala Ser Leu Leu Asn Asn Leu Val
            260                 265                 270

Val Cys Ser Lys Cys Gly Leu Gly Phe Val His Arg Arg Lys Asp Thr
        275                 280                 285

Met Ser Arg Gly Lys Lys Tyr His Tyr Arg Tyr Tyr Ser Cys Lys Thr
```

| | | | | | | | | | | | | |
|---|---|---|---|---|---|---|---|---|---|---|---|---|
| | | 290 | | | | 295 | | | | 300 | | |
| Tyr | Lys | His | Thr | His | Glu | Leu | Glu | Lys | Cys | Gly | Asn | Lys | Ile | Trp | Arg |
| 305 | | | | 310 | | | | | 315 | | | | | 320 | |
| Ala | Asp | Lys | Leu | Glu | Glu | Leu | Ile | Ile | Asn | Arg | Val | Asn | Asn | Tyr | Ser |
| | | | 325 | | | | | 330 | | | | | 335 | | |
| Phe | Ala | Ser | Arg | Asn | Val | Asp | Lys | Glu | Asp | Glu | Leu | Asp | Ser | Leu | Asn |
| | | | 340 | | | | | 345 | | | | | 350 | | |
| Glu | Lys | Leu | Lys | Ile | Glu | His | Ala | Lys | Lys | Arg | Leu | Phe | Asp | Leu | |
| | | 355 | | | | | 360 | | | | | 365 | | | |
| Tyr | Ile | Asn | Gly | Ser | Tyr | Glu | Val | Ser | Glu | Leu | Asp | Ser | Met | Met | Asn |
| | 370 | | | | | 375 | | | | | 380 | | | | |
| Asp | Ile | Asp | Ala | Gln | Ile | Asn | Tyr | Tyr | Glu | Ser | Gln | Ile | Glu | Ala | Asn |
| 385 | | | | 390 | | | | | 395 | | | | | 400 | |
| Glu | Glu | Leu | Lys | Lys | Asn | Lys | Lys | Ile | Gln | Asn | Leu | Ala | Asp | Leu | |
| | | | 405 | | | | | 410 | | | | | 415 | | |
| Ala | Thr | Val | Asp | Phe | Asp | Ser | Leu | Glu | Phe | Arg | Glu | Lys | Gln | Leu | Tyr |
| | | | 420 | | | | | 425 | | | | | 430 | | |
| Leu | Lys | Ser | Leu | Ile | Asn | Lys | Ile | Tyr | Ile | Asp | Gly | Glu | Gln | Val | Thr |
| | | | 435 | | | | | 440 | | | | | 445 | | |
| Ile | Glu | Trp | Leu | | | | | | | | | | | | |
| | | 450 | | | | | | | | | | | | | |

<210> SEQ ID NO 9
<211> LENGTH: 1410
<212> TYPE: DNA
<213> ORGANISM: Artificial Sequence
<220> FEATURE:
<223> OTHER INFORMATION: Synthetic gene

<400> SEQUENCE: 9

```
atgcggtaca ccaccccgt gagagccgcc gtgtacctga aatcagcga ggacagaagc      60
ggcgagcagt gggcgtggc cagacagaga aggactgcc tgaagctgtg cggccagaga     120
aagtgggtgc ccgtggagta cctggacaac gatgtgagcg ccagcaccgg caagaggaga     180
cccgcctacg agcagatgct ggccgacatc accgccggca gatcgccgc cgtggtggcc     240
tgggacctgg ataggctgca caggagaccc atcgagctgg aggccttcat gagcctggcc     300
gatgagaaaa gactggccct ggccaccgtg gccggcgacg tggacctggc accccccag     360
ggcagactgg tggccagact taagggcagc gtggccgccc acgagaccga gcacaagaag     420
gccagacagc ggagagccgc cagacagaag gccgagagag ccacccaa ctggagcaag     480
gccttcggct acctgcctgg ccccaacggc cccgagcccg accctagaac cgccctctg     540
gtgaagcagg cctacgccga catcctggcc ggagccagcc tggcgacgt gtgcagacag     600
tggaatgacg ccggagcctt caccatcacc ggcagaccct ggaccaccac caccctgagc     660
aagttcctgc ggaagcccag aaacgccggc ctgagagcct acaagggcgc cagatacggc     720
cccgtcgaca gagatgccat cgtgggcaag gcccagtgga gccccctggt ggacgaggcc     780
accttctggg ccgctcaggc cgtgctggac gcccctggca gagccccagg cagaaagagc     840
gtgcggagac acctgctcac cggcctggcc ggctgcggca agtgcggcaa ccacctggcc     900
ggcagctaca gaaccgatgg gcaggtggtg tacgtgtgca aggcctgcca cggcgtggcc     960
attctggccg acaacatcga gcccatcctg taccacatcg tggccgagag actggccatg    1020
cccgacgccc tggatctgct gaggagggag atccacgacg ccgccgaggc cgagaccatc    1080
agactcgagc tggaaaccct gtacggcgag ctggacgac tggccgtgga gagagccgag    1140
```

```
ggcctgctca cagccagaca ggtgaagatc agcaccgaca tcgtgaacgc caagatcacc    1200
aagctgcagg ccaggcagca ggaccaggag aggctgagag tgttcgacgg catccccctg    1260
ggcacccctc aggtggccgg catgattgcc gagctgagcc ccgatagatt cagggctgtg    1320
ctggatgtgc tggccgaggt ggtggtgcag cccgtgggca gagcggcag  aatcttcaac    1380 cccgagcggg tgcaggtgaa ctggagatag                                     1410
```

<210> SEQ ID NO 10
<211> LENGTH: 469
<212> TYPE: PRT
<213> ORGANISM: Putative recombinase of bacteriophage PhiRv1

<400> SEQUENCE: 10

```
Met Arg Tyr Thr Thr Pro Val Arg Ala Ala Val Tyr Leu Arg Ile Ser
 1               5                  10                  15

Glu Asp Arg Ser Gly Glu Gln Leu Gly Val Ala Arg Gln Arg Glu Asp
            20                  25                  30

Cys Leu Lys Leu Cys Gly Gln Arg Lys Trp Val Pro Val Glu Tyr Leu
        35                  40                  45

Asp Asn Asp Val Ser Ala Ser Thr Gly Lys Arg Arg Pro Ala Tyr Glu
    50                  55                  60

Gln Met Leu Ala Asp Ile Thr Ala Gly Lys Ile Ala Ala Val Val Ala
65                  70                  75                  80

Trp Asp Leu Asp Arg Leu His Arg Arg Pro Ile Glu Leu Glu Ala Phe
                85                  90                  95

Met Ser Leu Ala Asp Glu Lys Arg Leu Ala Leu Ala Thr Val Ala Gly
            100                 105                 110

Asp Val Asp Leu Ala Thr Pro Gln Gly Arg Leu Val Ala Arg Leu Lys
        115                 120                 125

Gly Ser Val Ala Ala His Glu Thr Glu His Lys Lys Ala Arg Gln Arg
    130                 135                 140

Arg Ala Ala Arg Gln Lys Ala Glu Arg Gly His Pro Asn Trp Ser Lys
145                 150                 155                 160

Ala Phe Gly Tyr Leu Pro Gly Pro Asn Gly Pro Glu Pro Asp Pro Arg
                165                 170                 175

Thr Ala Pro Leu Val Lys Gln Ala Tyr Ala Asp Ile Leu Ala Gly Ala
            180                 185                 190

Ser Leu Gly Asp Val Cys Arg Gln Trp Asn Asp Ala Gly Ala Phe Thr
        195                 200                 205

Ile Thr Gly Arg Pro Trp Thr Thr Thr Leu Ser Lys Phe Leu Arg
    210                 215                 220

Lys Pro Arg Asn Ala Gly Leu Arg Ala Tyr Lys Gly Ala Arg Tyr Gly
225                 230                 235                 240

Pro Val Asp Arg Asp Ala Ile Val Gly Lys Ala Gln Trp Ser Pro Leu
                245                 250                 255

Val Asp Glu Ala Thr Phe Trp Ala Ala Gln Ala Val Leu Asp Ala Pro
            260                 265                 270

Gly Arg Ala Pro Gly Arg Lys Ser Val Arg Arg His Leu Leu Thr Gly
        275                 280                 285

Leu Ala Gly Cys Gly Lys Cys Gly Asn His Leu Ala Gly Ser Tyr Arg
    290                 295                 300

Thr Asp Gly Gln Val Val Tyr Val Cys Lys Ala Cys His Gly Val Ala
305                 310                 315                 320
```

```
Ile Leu Ala Asp Asn Ile Glu Pro Ile Leu Tyr His Ile Val Ala Glu
            325                 330                 335

Arg Leu Ala Met Pro Asp Ala Val Asp Leu Leu Arg Arg Glu Ile His
        340                 345                 350

Asp Ala Ala Glu Ala Glu Thr Ile Arg Leu Glu Leu Glu Thr Leu Tyr
    355                 360                 365

Gly Glu Leu Asp Arg Leu Ala Val Glu Arg Ala Glu Gly Leu Leu Thr
370                 375                 380

Ala Arg Gln Val Lys Ile Ser Thr Asp Ile Val Asn Ala Lys Ile Thr
385                 390                 395                 400

Lys Leu Gln Ala Arg Gln Gln Asp Gln Glu Arg Leu Arg Val Phe Asp
                405                 410                 415

Gly Ile Pro Leu Gly Thr Pro Gln Val Ala Gly Met Ile Ala Glu Leu
            420                 425                 430

Ser Pro Asp Arg Phe Arg Ala Val Leu Asp Val Leu Ala Glu Val Val
        435                 440                 445

Val Gln Pro Val Gly Lys Ser Gly Arg Ile Phe Asn Pro Glu Arg Val
    450                 455                 460

Gln Val Asn Trp Arg
465

<210> SEQ ID NO 11
<211> LENGTH: 99
<212> TYPE: DNA
<213> ORGANISM: Artificial Sequence
<220> FEATURE:
<223> OTHER INFORMATION: SPBc2 attP site

<400> SEQUENCE: 11
acggcagagt aagcttcttt ttttcgttag atatgtagta agtatcttaa tatacagctt     60
tatctgtttt ttaagatact tactactttt cttagtgga                            99

<210> SEQ ID NO 12
<211> LENGTH: 1315
<212> TYPE: DNA
<213> ORGANISM: Artificial Sequence
<220> FEATURE:
<223> OTHER INFORMATION: STOP sequence

<400> SEQUENCE: 12
aagcttactt accatgtcag atccagacat gataagatac attgatgagt ttggacaaac     60
cacaactaga atgcagtgaa aaaatgctt tatttgtgaa atttgtgatg ctattgcttt    120
atttgtaacc attataagct gcaataaaca gttaacaac acaattgca ttcatttat      180 gtttcaggtt caggggggagg tgtgggaggt ttttaaagc aagtaaaacc tctacaaatg    240
tggtatggct gattatgatc tctagtcaag gcactataca tcaaatattc cttattaacc    300
cctttacaaa ttaaaaagct aaaggtacac aattttgag catagttatt aatagcagac    360
actctatgcc tgtgtggagt aagaaaaaac agtatgttat gattataact gttatgccta    420
cttataaagg ttacagaata ttttccata attttcttgt atagcagtgc agcttttcc      480 tttgtggtgt aaatagcaaa gcaagcaaga gttctattac taaacacagc atgactcaaa    540
aaacttagca attctgaagg aaagtccttg ggtcttcta cctttctctt ctttttgga      600 ggagtagaat gttgagagtc agcagtagcc tcatcatcac tagatggcat ttcttctgag    660
caaaacaggt tttcctcatt aaaggcattc caccactgct cccattcatc agttccatag    720
gttggaatct aaaatacaca acaattaga atcagtagtt taacacatta tacacttaaa    780
```

```
aattttatat ttaccttaga gctttaaatc tctgtaggta gtttgtccaa ttatgtcaca    840
ccacagaagt aaggttcctt cacaaagatc cctcgagaaa aaaatataaa agagatgga     900 ggaacgggaa aaagttagtt gtggtgatag gtggcaagtg gtattccgta agaacaacaa    960
gaaaagcatt tcatattatg gctgaactga gcgaacaagt gcaaaattta agcatcaacg   1020
acaacaacga gaatggttat gttcctcctc acttaagagg aaaaccaaga agtgccagaa   1080
ataacatgag caactacaat aacaacaacg gcggctacaa cggtggccgt ggcggtggca   1140
gcttctttag caacaaccgt cgtggtggtt acggcaacgg tggtttcttc ggtggaaaca   1200
acggtggcag cagatctaac ggccgttctg gtggtagatg gatcgatggc aaacatgtcc   1260
cagctccaag aaacgaaaag gccgagatcg ccatatttgg tgtccccgag gatcc        1315
```

<210> SEQ ID NO 13
<211> LENGTH: 96
<212> TYPE: DNA
<213> ORGANISM: Artificial Sequence
<220> FEATURE:
<223> OTHER INFORMATION: SPBc2 attB site

<400> SEQUENCE: 13

```
tcagataaca gcttggtggc acccattgtg ttcacaggag atacagcttt atctgtactg    60
atattaatga catgctgcac tcggtgtgaa agggca                              96
```

<210> SEQ ID NO 14
<211> LENGTH: 99
<212> TYPE: DNA
<213> ORGANISM: Artificial Sequence
<220> FEATURE:
<223> OTHER INFORMATION: SF370.1 attP site

<400> SEQUENCE: 14

```
acgaaaggag gtcgtgaaat ggataaaaaa atacagcgtt tttcatgtac aactatacta    60
gttgtagtgc ctaaataatg cttttaaaac ttaaaaata                           99
```

<210> SEQ ID NO 15
<211> LENGTH: 96
<212> TYPE: DNA
<213> ORGANISM: Artificial Sequence
<220> FEATURE:
<223> OTHER INFORMATION: SF370.1 attB site

<400> SEQUENCE: 15

```
taaagggat aataacgttt gtaaaggaga ctgataatgg catgtacaac tatactcgtc     60
ggtaaaaagg catcttatga tggctcaacc atggtt                              96
```

<210> SEQ ID NO 16
<211> LENGTH: 52
<212> TYPE: DNA
<213> ORGANISM: Artificial Sequence
<220> FEATURE:
<223> OTHER INFORMATION: Bxb1 attP site

<400> SEQUENCE: 16

```
gtggtttgtc tggtcaacca ccgcggtctc agtggtgtac ggtacaaacc ca            52
```

<210> SEQ ID NO 17
<211> LENGTH: 46
<212> TYPE: DNA
<213> ORGANISM: Artificial Sequence
<220> FEATURE:

<223> OTHER INFORMATION: Bxb1 attB site

<400> SEQUENCE: 17
ggccggcttg tcgacgacgg cggtctccgt cgtcaggatc atccgg         46

<210> SEQ ID NO 18
<211> LENGTH: 99
<212> TYPE: DNA
<213> ORGANISM: Artificial Sequence
<220> FEATURE:
<223> OTHER INFORMATION: A118 attP site

<400> SEQUENCE: 18
acgctagtag cttgtttatt tagattgttt agttcctcgt tttctctcgt tggaagaaga     60
agaaacgaga aactaaaatt ataaataaaa agtaaccta                            99

<210> SEQ ID NO 19
<211> LENGTH: 96
<212> TYPE: DNA
<213> ORGANISM: Artificial Sequence
<220> FEATURE:
<223> OTHER INFORMATION: A118 attB site

<400> SEQUENCE: 19
ttgagctaat taaaaccagc tgtaactttt tcggatcaag ctatgaagga cgcaaagagg     60
gaactaaaca cttaattggt gttacccata agccac                              96

<210> SEQ ID NO 20
<211> LENGTH: 99
<212> TYPE: DNA
<213> ORGANISM: Artificial Sequence
<220> FEATURE:
<223> OTHER INFORMATION: PhiRv1 attP site

<400> SEQUENCE: 20
acgagacagc agcacgcaca ggtgtagtgt atctcacagg tccacggttg gccgtggact     60
gctgaagaac attccacgcc aggagatcaa ccatgacca                           99

<210> SEQ ID NO 21
<211> LENGTH: 96
<212> TYPE: DNA
<213> ORGANISM: Artificial Sequence
<220> FEATURE:
<223> OTHER INFORMATION: PhiRv1 attB site

<400> SEQUENCE: 21
tggcgtagca gcttctcgtg gtggtggaag gtgttggtgc ggggttggcc gtggtcgagg     60
tggggtggtg gtagccattc ggtgtggccg tgggtg                              96

<210> SEQ ID NO 22
<211> LENGTH: 99
<212> TYPE: DNA
<213> ORGANISM: Artificial Sequence
<220> FEATURE:
<223> OTHER INFORMATION: Pseudo attB site on human chromosome 10

<400> SEQUENCE: 22
gttttggaaa aactctaggc agtttccctg aatcccaagc aggcttgttc aggcttacta     60
tttagagaaa atgggtctga cctggagagt cagtattta                           99

<210> SEQ ID NO 23
<211> LENGTH: 99

-continued

```
<212> TYPE: DNA
<213> ORGANISM: Artificial Sequence
<220> FEATURE:
<223> OTHER INFORMATION: Pseudo attR site after integration of target
      plasmid

<400> SEQUENCE: 23
acgaaaggag gtcgtgaaat ggataaaaaa atacagcgtt tttcatgtac aactatacta    60
tttagagaaa atgggtctga cctggagagt cagtattta                          99

<210> SEQ ID NO 24
<211> LENGTH: 99
<212> TYPE: DNA
<213> ORGANISM: Artificial Sequence
<220> FEATURE:
<223> OTHER INFORMATION: Pseudo attB site on human chromosome 15

<400> SEQUENCE: 24
ataagcacag gaacaaactc ataagagcct gcaatgagat catcagtgtc aagcactcat    60
tatagtgctt ggcatacacc aaatgttcag gagagatct                          99

<210> SEQ ID NO 25
<211> LENGTH: 99
<212> TYPE: DNA
<213> ORGANISM: Artificial Sequence
<220> FEATURE:
<223> OTHER INFORMATION: Pseudo attR site after integration of target
      plasmid

<400> SEQUENCE: 25
acggcagagt aagcttcttt ttttcgttag atatgtagta agtatcttaa tatacagctt    60
tatagtgctt ggcatacacc aaatgttcag gagagatct                          99

<210> SEQ ID NO 26
<211> LENGTH: 15
<212> TYPE: DNA
<213> ORGANISM: Artificial Sequence
<220> FEATURE:
<223> OTHER INFORMATION: synthetic peptide
<220> FEATURE:
<221> NAME/KEY: misc_feature
<222> LOCATION: (4)..(4)
<223> OTHER INFORMATION: k is g or t/u
<220> FEATURE:
<221> NAME/KEY: misc_feature
<222> LOCATION: (8)..(8)
<223> OTHER INFORMATION: n is a or g or c or t/u, unknown, or other
<220> FEATURE:
<221> NAME/KEY: misc_feature
<222> LOCATION: (12)..(12)
<223> OTHER INFORMATION: m is a or c

<400> SEQUENCE: 26
rrgktcantg amcyy                                                    15

<210> SEQ ID NO 27
<211> LENGTH: 13
<212> TYPE: DNA
<213> ORGANISM: Artificial Sequence
<220> FEATURE:
<223> OTHER INFORMATION: synthetic peptide
<220> FEATURE:
<221> NAME/KEY: misc_feature
<222> LOCATION: (7)..(7)
<223> OTHER INFORMATION: n is a or g or c or t/u, unknown, or other and
      can further vary in nucleotide length

<400> SEQUENCE: 27
```

-continued

```
aggtcanagg tca                                                    13

<210> SEQ ID NO 28
<211> LENGTH: 15
<212> TYPE: DNA
<213> ORGANISM: Artificial Sequence
<220> FEATURE:
<223> OTHER INFORMATION: synthetic peptide

<400> SEQUENCE: 28
gggttgaatg aattt                                                  15
```